US012589163B2

(12) United States Patent
Hakim et al.

(10) Patent No.: US 12,589,163 B2
(45) Date of Patent: Mar. 31, 2026

(54) SHEDDING BLOCKING AGENTS WITH INCREASED STABILITY

(71) Applicant: BIOND BIOLOGICS LTD., Misgav (IL)

(72) Inventors: Motti Hakim, Kibbutz Gazit (IL); Anna Fridman-Dror, Kibbutz Dalia (IL); Ilana Mandel, Manof (IL); Tehila Ben-Moshe, Tel Aviv (IL); Yair Sapir, Manof (IL); Avidor Shulman, Rakefet (IL); Lilach Chen Zeltsburg, Nahariya (IL); Ayala Lewkowicz, Kibbutz Kfar Szold (IL)

(73) Assignee: BIOND BIOLOGICS LTD., Misgav (IL)

( * ) Notice: Subject to any disclaimer, the term of this patent is extended or adjusted under 35 U.S.C. 154(b) by 768 days.

(21) Appl. No.: 17/910,975

(22) PCT Filed: Mar. 11, 2021

(86) PCT No.: PCT/IL2021/050271
§ 371 (c)(1),
(2) Date: Sep. 12, 2022

(87) PCT Pub. No.: WO2021/181396
PCT Pub. Date: Sep. 16, 2021

(65) Prior Publication Data
US 2023/0144459 A1 May 11, 2023

Related U.S. Application Data

(60) Provisional application No. 62/988,503, filed on Mar. 12, 2020.

(51) Int. Cl.
*A61K 47/68* (2017.01)
*A61K 47/60* (2017.01)
*A61K 47/65* (2017.01)
*C07K 14/765* (2006.01)
*C07K 16/28* (2006.01)

(52) U.S. Cl.
CPC .......... *A61K 47/6849* (2017.08); *A61K 47/60* (2017.08); *A61K 47/65* (2017.08); *C07K 14/765* (2013.01); *C07K 16/2818* (2013.01); *C07K 2317/22* (2013.01); *C07K 2317/55* (2013.01); *C07K 2317/569* (2013.01); *C07K 2317/75* (2013.01); *C07K 2317/76* (2013.01); *C07K 2317/92* (2013.01); *C07K 2317/94* (2013.01); *C07K 2319/21* (2013.01); *C07K 2319/31* (2013.01)

(58) Field of Classification Search
None
See application file for complete search history.

(56) References Cited

U.S. PATENT DOCUMENTS

2008/0038273 A1 2/2008 Soulillou et al.

FOREIGN PATENT DOCUMENTS

| CN | 100509849 C | 7/2009 |
|----|----|----|
| EP | 1378520 A1 | 1/2004 |
| EP | 2221317 A2 | 8/2010 |
| JP | 2010195797 A | 9/2010 |
| WO | 2004096139 A2 | 11/2004 |
| WO | 2010009391 A1 | 1/2010 |
| WO | 2018119001 A1 | 6/2018 |
| WO | 2019175885 A1 | 9/2019 |
| WO | 2020183473 A1 | 9/2020 |

OTHER PUBLICATIONS

Hoey RJ, Eom H, Horn JR. "Structure and development of single domain antibodies as modules for therapeutics and diagnostics". Exp Biol Med (Maywood). Dec. 2019;244(17): 1568-1576. doi: 10.1177/1535370219881129. Epub Oct. 9, 2019. PMID: 31594404; PMCID: PMC6920669.

Steeland S, Vandenbroucke RE, Libert C. "Nanobodies as therapeutics: big opportunities for small antibodies". Drug Discov Today. Jul. 2016;21(7):1076-113. doi: 10.1016/j.drudis.2016.04.003. Epub Apr. 11, 2016. PMID: 27080147.

Maussang, D, et al. "Llama-derived single variable domains (nanobodies) directed against chemokine receptor CXCR7 reduce head and neck cancer cell growth in vivo". J Biol Chem. Oct. 11, 2013;288(41):29562-72. doi: 10.1074/jbc.M113.498436. Epub Aug. 26, 2013. PMID: 23979133; PMCID: PMC3795254.

Vosjan MJ, Vercammen J, Kolkman JA, Stigter-van Walsum M, Revets H, van Dongen GA. "Nanobodies targeting the hepatocyte growth factor: potential new drugs for molecular cancer therapy". Mol Cancer Ther. Apr. 2012;11(4):1017-25. doi: 10.1158/1535-7163.MCT-11-0891. Epub Feb. 7, 2012. PMID: 22319202.

Sun Z, Yi L, Tao H, Huang J, Jin Z, Xiao Y, Feng C, Sun J. "Enhancement of soluble CD28 levels in the serum of Graves' disease". Cent Eur J Immunol. 2014;39(2):216-22. doi: 10.5114/ceji.2014.43726. Epub Jun. 27, 2014. PMID: 26155127; PMCID: PMC4440026.

Daniel et al., "Costimulation with Agonistic Anti-CD28 Antibodies Prevents T Cell Apoptosis and is Required for Efficient Immunotherapy with CD3x19 Bispecific Antibodies in B Cell Lymphoma", Free communications and posters, Article 97, S42, 1997.

Hedemann et al., "ADAM17 inhibition enhances platinum efficiency in ovarian cancer", Oncotarget, vol. 9, No. 22, 16043-16058, 2018. doi: 10.18632/oncotarget.24682. PMID: 29662625; PMCID: PMC5882316.

(Continued)

*Primary Examiner* — Brian Gangle
(74) *Attorney, Agent, or Firm* — The Roy Gross Law Firm, LLC; Roy D. Gross

(57) ABSTRACT

Agents comprising at least two moieties separated by a linker, wherein a first moiety binds mCD28 on a surface of a cell and inhibits proteolytic cleavage of the mCD28 and wherein a second moiety increases stability of the first moiety are provided. Methods of treating cancer and improving immunotherapy comprising administering the agents are also provided.

20 Claims, 22 Drawing Sheets

Specification includes a Sequence Listing.

(56) References Cited

OTHER PUBLICATIONS

Huang et al., "Targeting the Sheddase Activity of ADAM17 by an Anti-ADAM17 Antibody D1(A12) Inhibits Head and Neck Squamous Cell Carcinoma Cell Proliferation and Motility via Blockage of Bradykinin Induced HERs Transactivation", International Journal of Biological Sciences, vol. 10 (7): 702-714, 2014. doi: 10.7150/ijbs.9326. PMID: 25013379; PMCID: PMC4081605.

Isitmangil et al., "Association of CTLA4 and CD28 Gene Variants and Circulating Levels of Their Proteins in Patients with Breast Cancer", in vivo, 30, 485-494, 2016. PMID: 27381613.

Murray et al., "CD28-mediated pro-survival signaling induces chemotherapeutic resistance in multiple myeloma", Blood, vol. 123, No. 24, 3770-3779, 2014. doi: 10.1182/blood-2013-10-530964. Epub Apr. 29, 2014. PMID: 24782505; PMCID: PMC4055924.

Hamzaoui et al., "Circulating soluble CD28 in patients with Behcet's disease: Relationship to clinical manifestations", Clinical and Experimental Rheumatology, 23 (Suppl. 38), S49-S52, 2005. PMID: 16273764.

Hebbar et al., "Detection of circulating soluble CD28 in patients with systemic lupus erythematosus, primary Sjögren's syndrome and systemic sclerosis", Clinical and Experimental Immunology, 136, 388-392, 2004. doi: 10.1111/i.1365-2249.2004.02427.x. PMID: 15086406; PMCID: PMC1809021.

Igawa et al., "Sweeping antibody as a novel therapeutic antibody modality capable of eliminating soluble antigens from circulation", Immunological Reviews, vol. 270, 132-151, 2016. https://doi.org/10.1111/imr.12392.

W.K. Ip, et al., "Plasma Concentrations of Soluble CTLA-4, CD28, CD80 and CD86 Costimulatory Molecules Reflect Disease Severity of Acute Asthma in Children", Pediatric Pulmonology 41, 674-682, 2006. doi: 10.1002/ppul.20432. PMID: 16703581.

Sun et al., "Enhancement of soluble CD28 levels in the serum of Graves' disease", Central European Journal of Immunology, 39 (2), 216-222, 2014. doi: 10.5114/ceji.2014.43726. Epub Jun. 27, 2014. PMID: 26155127; PMCID: PMC4440026.

Wang et al., "Plasma sCD28, sCTLA-4 levels in neuromyelitis optica and multiple sclerosis during relapse", Journal of Neuroimmunology, 243, 52-55, 2012. doi: 10.1016/j.jneuroim.2011.11.010. Epub Dec. 15, 2011. PMID: 22177277.

Wong et al., "Aberrant production of soluble costimulatory molecules CTLA-4, CD28, CD80 and CD86 in patients with systemic lupus erythematosus", Rheumatology (Oxford). Aug. 2005;44(8):989-94. doi: 10.1093/rheumatology/keh663. Epub May 3, 2005. PMID: 15870153.

Schroter et al., "A generic approach to engineer antibody pH-switches using combinatorial histidine scanning libraries and yeast display", MAbs. 2015;7(1):138-51. doi: 10.4161/19420862.2014.985993. PMID: 25523975; PMCID: PMC4622719.

Yang et al., "Maximizing in vivo target clearance by design of pH-dependent target binding antibodies with altered affinity to FcRn", MAbs. Oct. 2017;9(7):1105-1117. doi: 10.1080/19420862.2017.1359455. Epub Aug. 8, 2017. PMID: 28786732; PMCID: PMC5627591.

Kamphorst et al., "Rescue of exhausted CD8 T cells by PD-1-targeted therapies is CD28-dependent", Science, 355, 6332, 1423-1427, 2017. doi: 10.1126/science.aaf0683. Epub Mar. 9, 2017. PMID: 28280249; PMCID: PMC5595217.

Hui et al., "T cell costimulatory receptor CD28 is a primary target for PD-1-mediated inhibition", Science, 355, 6332, 1428-1433, 2017. doi: 10.1126/science.aaf1292. Epub Mar. 9, 2017. PMID: 28280247; PMCID: PMC6286077.

Magistrelli et al., "Identification of Three Alternatively Spliced Variants of Human CD28 mRNA", Biochemical and Biophysical Research Communications, 259, 34-37, 1999. https://doi.org/10.1006/bbrc.1999.0725.

Danquah W, Meyer-Schwesinger C, Rissiek B, Pinto C, Serracant-Prat A, Amadi M, Iacenda D, Knop JH, Hammel A, Bergmann P, Schwarz N, Assunção J, Rotthier W, Haag F, Tolosa E, Bannas P, Boué-Grabot E, Magnus T, Laeremans T, Stortelers C, Koch-Nolte F. "Nanobodies that block gating of the P2X7 ion channel ameliorate inflammation". Sci Transl Med. Nov. 23, 2016;8(366):366ra162. doi: 10.1126/scitranslmed.aaf8463. PMID: 27881823.

PCT International Search Report for International Application No. PCT/IL2021/050271, mailed May 25, 2021, 26pp.

PCT Written Opinion for International Application No. PCT/IL2021/050271, mailed May 25, 2021, 9pp.

PCT International Preliminary Report on Patentability for International Application No. PCT/IL2021/050271, issued Sep. 6, 2022, 10pp.

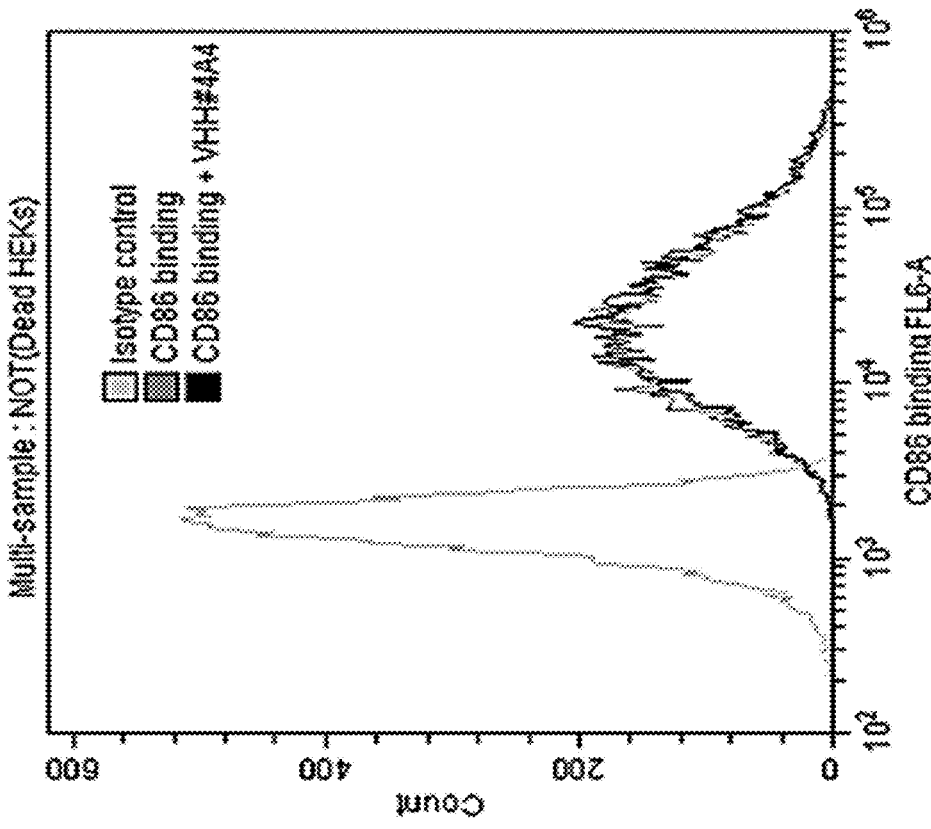
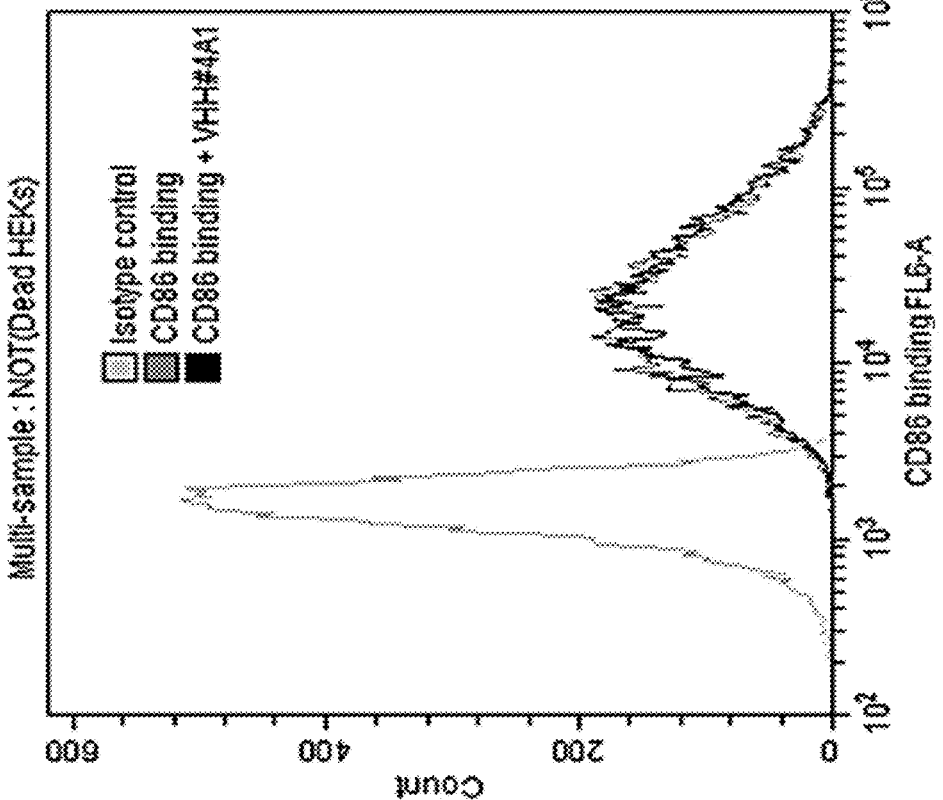
Figure 10_continued

SEQUENCE LISTING

```
<160> NUMBER OF SEQ ID NOS: 65

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Ile Asn Ala Met Gly
1               5

<210> SEQ ID NO 2
<211> LENGTH: 16
<212> TYPE: PRT
<213> ORGANISM: Artificial
<220> FEATURE:
<223> OTHER INFORMATION: Synthetic

<400> SEQUENCE: 2

Ala Ile Ser Gly Gly Gly Asp Thr Tyr Tyr Ala Asp Ser Val Lys Gly
1               5                   10                  15
```

```
<210> SEQ ID NO 3
<211> LENGTH: 9
<212> TYPE: PRT
<213> ORGANISM: Artificial
<220> FEATURE:
<223> OTHER INFORMATION: Synthetic

<400> SEQUENCE: 3

Asp Leu Tyr Gly Ser Asp Tyr Trp Asp
1               5

<210> SEQ ID NO 4
<211> LENGTH: 5
<212> TYPE: PRT
<213> ORGANISM: Artificial
<220> FEATURE:
<223> OTHER INFORMATION: Synthetic

<400> SEQUENCE: 4

Ile Asn Ala Met Ala
1               5

<210> SEQ ID NO 5
<211> LENGTH: 16
<212> TYPE: PRT
<213> ORGANISM: Artificial
<220> FEATURE:
<223> OTHER INFORMATION: Synthetic

<400> SEQUENCE: 5

Ala Ile Thr Ser Ser Gly Ser Thr Asn Tyr Ala Asn Ser Val Lys Gly
1               5                   10                  15

<210> SEQ ID NO 6
<211> LENGTH: 9
<212> TYPE: PRT
<213> ORGANISM: Artificial
<220> FEATURE:
<223> OTHER INFORMATION: Synthetic

<400> SEQUENCE: 6

Asp Glu Tyr Gly Ser Asp Tyr Trp Ile
1               5

<210> SEQ ID NO 7
<211> LENGTH: 16
<212> TYPE: PRT
<213> ORGANISM: Artificial
<220> FEATURE:
<223> OTHER INFORMATION: Synthetic

<400> SEQUENCE: 7

Ala Ile Thr Ser Gly Gly Ser Thr Asn Tyr Ala Asp Ser Val Lys Gly
1               5                   10                  15

<210> SEQ ID NO 8
<211> LENGTH: 9
<212> TYPE: PRT
<213> ORGANISM: Artificial
<220> FEATURE:
<223> OTHER INFORMATION: Synthetic

<400> SEQUENCE: 8

Asp Leu Tyr Gly Glu Asp Tyr Trp Ile
1               5
```

<210> SEQ ID NO 9
<211> LENGTH: 117
<212> TYPE: PRT
<213> ORGANISM: Artificial
<220> FEATURE:
<223> OTHER INFORMATION: Synthetic

<400> SEQUENCE: 9

```
Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Ala Ser Ile Asn
            20                  25                  30

Ala Met Gly Trp Tyr Arg Gln Ala Pro Gly Ser Gln Arg Glu Leu Val
            35                  40                  45

Ala Ala Ile Ser Gly Gly Gly Asp Thr Tyr Tyr Ala Asp Ser Val Lys
        50                  55                  60

Gly Arg Phe Thr Ile Ser Arg Asp Asn Ala Lys Thr Thr Val Tyr Leu
65                  70                  75                  80

Gln Met Asn Ser Leu Arg Pro Glu Asp Thr Ala Val Tyr Tyr Cys Val
                85                  90                  95

Val Asp Leu Tyr Gly Ser Asp Tyr Trp Asp Trp Gly Gln Gly Thr Gln
            100                 105                 110

Val Thr Val Ser Ser
        115
```

<210> SEQ ID NO 10
<211> LENGTH: 117
<212> TYPE: PRT
<213> ORGANISM: Artificial
<220> FEATURE:
<223> OTHER INFORMATION: Synthetic

<400> SEQUENCE: 10

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Leu Phe Ser Ile Asn
            20                  25                  30

Ala Met Ala Trp Tyr Arg Gln Ala Pro Gly Lys Gln Arg Glu Leu Val
            35                  40                  45

Ala Ala Ile Thr Ser Ser Gly Ser Thr Asn Tyr Ala Asn Ser Val Lys
        50                  55                  60

Gly Arg Phe Thr Val Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Val
                85                  90                  95

Val Asp Glu Tyr Gly Ser Asp Tyr Trp Ile Trp Gly Gln Gly Thr Gln
            100                 105                 110

Val Thr Val Ser Ser
        115
```

<210> SEQ ID NO 11
<211> LENGTH: 117
<212> TYPE: PRT
<213> ORGANISM: Artificial
<220> FEATURE:
<223> OTHER INFORMATION: Synthetic

<400> SEQUENCE: 11

```
Gln Val Gln Leu Val Glu Ser Gly Gly Gly Leu Val Gln Ala Gly Gly
```

-continued

```
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Arg Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Glu Pro Arg Asp Ala Gly Val Tyr Tyr Cys Val
                85                  90                  95

Val Asp Leu Tyr Gly Glu Asp Tyr Trp Ile Trp Gly Gln Gly Thr Gln
            100                 105                 110

Val Thr Val Ser Ser
        115

<210> SEQ ID NO 12
<211> LENGTH: 10
<212> TYPE: PRT
<213> ORGANISM: Artificial
<220> FEATURE:
<223> OTHER INFORMATION: Synthetic

<400> SEQUENCE: 12

Gly Phe Thr Phe Ser Ser Tyr Tyr Met Ser
1               5                   10

<210> SEQ ID NO 13
<211> LENGTH: 17
<212> TYPE: PRT
<213> ORGANISM: Artificial
<220> FEATURE:
<223> OTHER INFORMATION: Synthetic

<400> SEQUENCE: 13

Thr Ile Ser Asp Gly Gly Asp Asn Thr Tyr Tyr Ala Gly Thr Val Thr
1               5                   10                  15

Gly

<210> SEQ ID NO 14
<211> LENGTH: 9
<212> TYPE: PRT
<213> ORGANISM: Artificial
<220> FEATURE:
<223> OTHER INFORMATION: Synthetic

<400> SEQUENCE: 14

Ile His Trp Pro Tyr Tyr Phe Asp Ser
1               5

<210> SEQ ID NO 15
<211> LENGTH: 10
<212> TYPE: PRT
<213> ORGANISM: Artificial
<220> FEATURE:
<223> OTHER INFORMATION: Synthetic

<400> SEQUENCE: 15

Arg Ala Ser Ser Ser Val Ser Tyr Met Asn
1               5                   10

<210> SEQ ID NO 16
```

```
<211> LENGTH: 7
<212> TYPE: PRT
<213> ORGANISM: Artificial
<220> FEATURE:
<223> OTHER INFORMATION: Synthetic

<400> SEQUENCE: 16

Ala Thr Ser Asp Leu Ala Ser
1               5

<210> SEQ ID NO 17
<211> LENGTH: 9
<212> TYPE: PRT
<213> ORGANISM: Artificial
<220> FEATURE:
<223> OTHER INFORMATION: Synthetic

<400> SEQUENCE: 17

Gln Gln Trp Ser Ser His Pro Pro Thr
1               5

<210> SEQ ID NO 18
<211> LENGTH: 5
<212> TYPE: PRT
<213> ORGANISM: Artificial
<220> FEATURE:
<223> OTHER INFORMATION: Synthetic

<400> SEQUENCE: 18

Gly Gly Gly Gly Ser
1               5

<210> SEQ ID NO 19
<211> LENGTH: 118
<212> TYPE: PRT
<213> ORGANISM: Artificial
<220> FEATURE:
<223> OTHER INFORMATION: Synthetic

<400> SEQUENCE: 19

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala
        115

<210> SEQ ID NO 20
<211> LENGTH: 220
<212> TYPE: PRT
<213> ORGANISM: Homo sapiens

<400> SEQUENCE: 20
```

-continued

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Tyr Leu Asp Asn Glu Lys Ser
            115                 120                 125

Asn Gly Thr Ile Ile His Val Lys Gly Lys His Leu Cys Pro Ser Pro
        130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
        210                 215                 220

<210> SEQ ID NO 21
<211> LENGTH: 202
<212> TYPE: PRT
<213> ORGANISM: Homo sapiens

<400> SEQUENCE: 21

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro Phe Trp Val Leu Val Val Val Gly Gly Val
        130                 135                 140

Leu Ala Cys Tyr Ser Leu Leu Val Thr Val Ala Phe Ile Ile Phe Trp
145                 150                 155                 160
```

Val Arg Ser Lys Arg Ser Arg Leu Leu His Ser Asp Tyr Met Asn Met
              165                170             175

Thr Pro Arg Arg Pro Gly Pro Thr Arg Lys His Tyr Gln Pro Tyr Ala
              180                185             190

Pro Pro Arg Asp Phe Ala Ala Tyr Arg Ser
       195              200

<210> SEQ ID NO 22
<211> LENGTH: 663
<212> TYPE: DNA
<213> ORGANISM: Homo sapiens

<400> SEQUENCE: 22
atgctcaggc tgctcttggc tctcaactta ttcccttcaa ttcaagtaac aggaaacaag    60
attttggtga agcagtcgcc catgcttgta gcgtacgaca atgcggtcaa ccttagctgc   120
aagtattcct acaatctctt ctcaagggag ttccgggcat cccttcacaa aggactggat   180
agtgctgtgg aagtctgtgt tgtatatggg aattactccc agcagcttca ggtttactca   240
aaaacggggt tcaactgtga tgggaaattg ggcaatgaat cagtgacatt ctacctccag   300
aatttgtatg ttaaccaaac agatatttac ttctgcaaaa ttgaagttat gtatcctcct   360
ccttacctag acaatgagaa gagcaatgga accattatcc atgtgaaagg gaaacacctt   420
tgtccaagtc ccctatttcc cggaccttct aagcccttt gggtgctggt ggtggttggt   480
ggagtcctgg cttgctatag cttgctagta acagtggcct ttattatttt ctgggtgagg   540
agtaagagga gcaggctcct gcacagtgac tacatgaaca tgactccccg ccgcccgggg   600
cccacccgca agcattacca gccctatgcc ccaccacgcg acttcgcagc ctatcgctcc   660
tga    663

<210> SEQ ID NO 23
<211> LENGTH: 27
<212> TYPE: PRT
<213> ORGANISM: Homo sapiens

<400> SEQUENCE: 23

Phe Trp Val Leu Val Val Val Gly Gly Val Leu Ala Cys Tyr Ser Leu
1               5                10               15

Leu Val Thr Val Ala Phe Ile Ile Phe Trp Val
             20               25

<210> SEQ ID NO 24
<211> LENGTH: 139
<212> TYPE: PRT
<213> ORGANISM: Homo sapiens

<400> SEQUENCE: 24

Met Leu Arg Leu Leu Leu Ala Leu Asn Leu Phe Pro Ser Ile Gln Val
1               5                10               15

Thr Gly Asn Lys Ile Leu Val Lys Gln Ser Pro Met Leu Val Ala Tyr
             20               25             30

Asp Asn Ala Val Asn Leu Ser Cys Lys Tyr Ser Tyr Asn Leu Phe Ser
        35              40             45

Arg Glu Phe Arg Ala Ser Leu His Lys Gly Leu Asp Ser Ala Val Glu
     50              55             60

Val Cys Val Val Tyr Gly Asn Tyr Ser Gln Gln Leu Gln Val Tyr Ser
65              70              75             80

```
Lys Thr Gly Phe Asn Cys Asp Gly Lys Leu Gly Asn Glu Ser Val Thr
            85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Tyr Leu Asp Asn Glu Lys Ser
        115                 120                 125

Asn Gly Thr Ile Ile His Val Lys Gly Glu Glu
        130                 135

<210> SEQ ID NO 25
<211> LENGTH: 121
<212> TYPE: PRT
<213> ORGANISM: Homo sapiens

<400> SEQUENCE: 25

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Glu Glu
        115                 120

<210> SEQ ID NO 26
<211> LENGTH: 144
<212> TYPE: PRT
<213> ORGANISM: Homo sapiens

<400> SEQUENCE: 26

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
        130                 135                 140
```

-continued

```
<210> SEQ ID NO 27
<211> LENGTH: 126
<212> TYPE: PRT
<213> ORGANISM: Homo sapiens

<400> SEQUENCE: 27

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
            85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro
        115                 120                 125

<210> SEQ ID NO 28
<211> LENGTH: 538
<212> TYPE: DNA
<213> ORGANISM: Homo sapiens

<400> SEQUENCE: 28
atgctcaggc tgctcttggc tctcaactta ttcccttcaa ttcaagtaac aggaaacaag      60
attttggtga agcagtcgcc catgcttgta gcgtacgaca atgcggtcaa ccttagctgc     120
aagtattcct acaatctctt ctcaagggag ttccgggcat cccttcacaa aggactggat     180
agtgctgtgg aagtctgtgt tgtatatggg aattactccc agcagcttca ggtttactca     240
aaaacggggt caactgtgat gggaaattg ggcaatgaat cagtgacatt ctacctccag      300
aatttgtatg ttaaccaaac agatatttac ttctgcaaaa ttgaagttat gtatcctcct     360
ccttacctag acaatgagaa gagcaatgga accattatcc atgtgaaagg tgaggagtaa     420
gaggagcagg ctcctgcaca gtgactacat gaacatgact ccccgccgcc ccgggcccac     480
ccgcaagcat taccagccct atgccccacc acgcgacttc gcagcctatc gctcctga      538

<210> SEQ ID NO 29
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (5)..(5)
<223> OTHER INFORMATION: X is G or A

<400> SEQUENCE: 29

Ile Asn Ala Met Xaa
1               5

<210> SEQ ID NO 30
<211> LENGTH: 16
<212> TYPE: PRT
```

```
<213> ORGANISM: Artificial
<220> FEATURE:
<223> OTHER INFORMATION: Synthetic
<220> FEATURE:
<221> NAME/KEY: X
<222> LOCATION: (3)..(3)
<223> OTHER INFORMATION: X is S or T
<220> FEATURE:
<221> NAME/KEY: X
<222> LOCATION: (4)..(4)
<223> OTHER INFORMATION: X is G or S
<220> FEATURE:
<221> NAME/KEY: X
<222> LOCATION: (5)..(5)
<223> OTHER INFORMATION: X is G or S
<220> FEATURE:
<221> NAME/KEY: X
<222> LOCATION: (7)..(7)
<223> OTHER INFORMATION: X is D or S
<220> FEATURE:
<221> NAME/KEY: X
<222> LOCATION: (9)..(9)
<223> OTHER INFORMATION: X is Y or N
<220> FEATURE:
<221> NAME/KEY: X
<222> LOCATION: (12)..(12)
<223> OTHER INFORMATION: X is D or N

<400> SEQUENCE: 30

Ala Ile Xaa Xaa Xaa Gly Xaa Thr Xaa Tyr Ala Xaa Ser Val Lys Gly
1               5                   10                  15

<210> SEQ ID NO 31
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (2)..(2)
<223> OTHER INFORMATION: X is E or L
<220> FEATURE:
<221> NAME/KEY: X
<222> LOCATION: (5)..(5)
<223> OTHER INFORMATION: X is E or S
<220> FEATURE:
<221> NAME/KEY: X
<222> LOCATION: (9)..(9)
<223> OTHER INFORMATION: X is D or I

<400> SEQUENCE: 31

Asp Xaa Tyr Gly Xaa Asp Tyr Trp Xaa
1               5

<210> SEQ ID NO 32
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (2)..(2)
<223> OTHER INFORMATION: X is E or L
<220> FEATURE:
<221> NAME/KEY: X
<222> LOCATION: (9)..(9)
<223> OTHER INFORMATION: X is D or I

<400> SEQUENCE: 32

Asp Xaa Tyr Gly Ser Asp Tyr Trp Xaa
1               5
```

-continued

<210> SEQ ID NO 33
<211> LENGTH: 126
<212> TYPE: PRT
<213> ORGANISM: Artificial
<220> FEATURE:
<223> OTHER INFORMATION: Synthetic

<400> SEQUENCE: 33

```
Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Ala Ser Ile Asn
            20                  25                  30

Ala Met Gly Trp Tyr Arg Gln Ala Pro Gly Ser Gln Arg Glu Leu Val
            35                  40                  45

Ala Ala Ile Ser Gly Gly Gly Asp Thr Tyr Tyr Ala Asp Ser Val Lys
        50                  55                  60

Gly Arg Phe Thr Ile Ser Arg Asp Asn Ala Lys Thr Thr Val Tyr Leu
65                  70                  75                  80

Gln Met Asn Ser Leu Arg Pro Glu Asp Thr Ala Val Tyr Tyr Cys Val
                85                  90                  95

Val Asp Leu Tyr Gly Ser Asp Tyr Trp Asp Trp Gly Gln Gly Thr Gln
            100                 105                 110

Val Thr Val Ser Ser Ala Ala Ala His His His His His His
        115                 120                 125
```

<210> SEQ ID NO 34
<211> LENGTH: 126
<212> TYPE: PRT
<213> ORGANISM: Artificial
<220> FEATURE:
<223> OTHER INFORMATION: Synthetic

<400> SEQUENCE: 34

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Leu Phe Ser Ile Asn
            20                  25                  30

Ala Met Ala Trp Tyr Arg Gln Ala Pro Gly Lys Gln Arg Glu Leu Val
            35                  40                  45

Ala Ala Ile Thr Ser Ser Gly Ser Thr Asn Tyr Ala Asn Ser Val Lys
        50                  55                  60

Gly Arg Phe Thr Val Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Val
                85                  90                  95

Val Asp Glu Tyr Gly Ser Asp Tyr Trp Ile Trp Gly Gln Gly Thr Gln
            100                 105                 110

Val Thr Val Ser Ser Ala Ala Ala His His His His His His
        115                 120                 125
```

<210> SEQ ID NO 35
<211> LENGTH: 126
<212> TYPE: PRT
<213> ORGANISM: Artificial
<220> FEATURE:
<223> OTHER INFORMATION: Synthetic

<400> SEQUENCE: 35

```
Gln Val Gln Leu Val Glu Ser Gly Gly Gly Leu Val Gln Ala Gly Gly
```

-continued

```
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Arg Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Glu Pro Arg Asp Ala Gly Val Tyr Tyr Cys Val
                85                  90                  95

Val Asp Leu Tyr Gly Glu Asp Tyr Trp Ile Trp Gly Gln Gly Thr Gln
            100                 105                 110

Val Thr Val Ser Ser Ala Ala Ala His His His His His His
            115                 120                 125
```

<210> SEQ ID NO 36
<211> LENGTH: 128
<212> TYPE: PRT
<213> ORGANISM: Artificial
<220> FEATURE:
<223> OTHER INFORMATION: Synthetic

<400> SEQUENCE: 36

```
Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Ala Ser Ile Asn
            20                  25                  30

Ala Met Gly Trp Tyr Arg Gln Ala Pro Gly Ser Gln Arg Glu Leu Val
        35                  40                  45

Ala Ala Ile Ser Gly Gly Gly Asp Thr Tyr Tyr Ala Asp Ser Val Lys
    50                  55                  60

Gly Arg Phe Thr Ile Ser Arg Asp Asn Ala Lys Thr Thr Val Tyr Leu
65                  70                  75                  80

Gln Met Asn Ser Leu Arg Pro Glu Asp Thr Ala Val Tyr Tyr Cys Val
                85                  90                  95

Val Asp Leu Tyr Gly Ser Asp Tyr Trp Asp Trp Gly Gln Gly Thr Gln
            100                 105                 110

Val Thr Val Ser Ser Ala Ala Ala His His His His His His Gly Cys
            115                 120                 125
```

<210> SEQ ID NO 37
<211> LENGTH: 128
<212> TYPE: PRT
<213> ORGANISM: Artificial
<220> FEATURE:
<223> OTHER INFORMATION: Synthetic

<400> SEQUENCE: 37

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Leu Phe Ser Ile Asn
            20                  25                  30

Ala Met Ala Trp Tyr Arg Gln Ala Pro Gly Lys Gln Arg Glu Leu Val
        35                  40                  45

Ala Ala Ile Thr Ser Ser Gly Ser Thr Asn Tyr Ala Asn Ser Val Lys
    50                  55                  60
```

-continued

```
Gly Arg Phe Thr Val Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Val
                85                  90                  95

Val Asp Glu Tyr Gly Ser Asp Tyr Trp Ile Trp Gly Gln Gly Thr Gln
                100                 105                 110

Val Thr Val Ser Ser Ala Ala Ala His His His His His His Gly Cys
        115                 120                 125

<210> SEQ ID NO 38
<211> LENGTH: 128
<212> TYPE: PRT
<213> ORGANISM: Artificial
<220> FEATURE:
<223> OTHER INFORMATION: Synthetic

<400> SEQUENCE: 38

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
                20                  25                  30

Ala Met Gly Trp Tyr Arg Gln Ala Pro Gly Lys Gln Arg Glu Arg Val
            35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Glu Pro Arg Asp Ala Gly Val Tyr Tyr Cys Val
                85                  90                  95

Val Asp Leu Tyr Gly Glu Asp Tyr Trp Ile Trp Gly Gln Gly Thr Gln
                100                 105                 110

Val Thr Val Ser Ser Ala Ala Ala His His His His His His Gly Cys
        115                 120                 125

<210> SEQ ID NO 39
<211> LENGTH: 7
<212> TYPE: PRT
<213> ORGANISM: Artificial
<220> FEATURE:
<223> OTHER INFORMATION: Synthetic

<400> SEQUENCE: 39

Gly Tyr Thr Leu Thr Asn Tyr
1               5

<210> SEQ ID NO 40
<211> LENGTH: 6
<212> TYPE: PRT
<213> ORGANISM: Artificial
<220> FEATURE:
<223> OTHER INFORMATION: Synthetic

<400> SEQUENCE: 40

Asn Thr Tyr Thr Gly Lys
1               5

<210> SEQ ID NO 41
<211> LENGTH: 9
<212> TYPE: PRT
<213> ORGANISM: Artificial
<220> FEATURE:
<223> OTHER INFORMATION: Synthetic
```

<400> SEQUENCE: 41

Gly Asp Ala Asn Gln Gln Phe Ala Tyr
1               5

<210> SEQ ID NO 42
<211> LENGTH: 11
<212> TYPE: PRT
<213> ORGANISM: Artificial
<220> FEATURE:
<223> OTHER INFORMATION: Synthetic

<400> SEQUENCE: 42

Lys Ala Ser Gln Asp Ile Asn Ser Tyr Leu Ser
1               5                   10

<210> SEQ ID NO 43
<211> LENGTH: 7
<212> TYPE: PRT
<213> ORGANISM: Artificial
<220> FEATURE:
<223> OTHER INFORMATION: Synthetic

<400> SEQUENCE: 43

Arg Ala Asn Arg Leu Val Asp
1               5

<210> SEQ ID NO 44
<211> LENGTH: 9
<212> TYPE: PRT
<213> ORGANISM: Artificial
<220> FEATURE:
<223> OTHER INFORMATION: Synthetic

<400> SEQUENCE: 44

Leu Gln Tyr Asp Glu Phe Pro Pro Thr
1               5

<210> SEQ ID NO 45
<211> LENGTH: 118
<212> TYPE: PRT
<213> ORGANISM: Artificial
<220> FEATURE:
<223> OTHER INFORMATION: Synthetic

<400> SEQUENCE: 45

Asp Val Lys Leu Val Glu Ser Gly Gly Gly Leu Val Lys Leu Gly Gly
1               5                   10                  15

Ser Leu Lys Leu Ser Cys Val Ala Ser Gly Phe Thr Phe Ser Ser Tyr
            20                  25                  30

Tyr Met Ser Trp Val Arg Gln Thr Pro Glu Lys Arg Leu Glu Trp Val
        35                  40                  45

Ala Thr Ile Ser Asp Gly Gly Asp Asn Thr Tyr Tyr Ala Gly Thr Val
    50                  55                  60

Thr Gly Arg Phe Thr Ile Ser Arg Asp Phe Ala Lys Asn Thr Leu Tyr
65                  70                  75                  80

Leu Gln Met Asn Ser Leu Thr Ser Glu Asp Thr Ala Val Tyr Tyr Cys
                85                  90                  95

Ala Arg Ile His Trp Pro Tyr Tyr Phe Asp Ser Trp Gly Gln Gly Thr
            100                 105                 110

Thr Leu Thr Val Ser Ser
        115

<210> SEQ ID NO 46
<211> LENGTH: 354
<212> TYPE: DNA
<213> ORGANISM: Artificial
<220> FEATURE:
<223> OTHER INFORMATION: Synthetic

<400> SEQUENCE: 46
gacgtgaagc tcgtggagtc tggggggaggc ttagtgaagc ttggagggtc cctgaaactc      60
tcctgtgtag cctctggatt cactttcagt agctattaca tgtcttgggt tcgccagact     120
ccggagaaga ggctggagtg ggtcgcgacc ataagtgatg gtggtgataa cacctactac     180
gcaggcactg tgacgggccg attcaccatc tccagagact ttgccaagaa cacccctgtac    240 ctgcaaatga acagtctgac ctctgaggac acagccgtgt attactgtgc aagaattcat     300
tggccttact attttgactc ctggggccaa ggcaccactc tcacagtctc ctca           354

<210> SEQ ID NO 47
<211> LENGTH: 106
<212> TYPE: PRT
<213> ORGANISM: Artificial
<220> FEATURE:
<223> OTHER INFORMATION: Synthetic

<400> SEQUENCE: 47

Gln Phe Val Leu Ser Gln Ser Pro Ala Ile Leu Ser Ala Ser Pro Gly
1               5                   10                  15

Glu Met Leu Thr Met Thr Cys Arg Ala Ser Ser Ser Val Ser Tyr Met
            20                  25                  30

Asn Trp Tyr Gln Gln Lys Pro Gly Ser Ser Pro Lys Pro Trp Ile Tyr
        35                  40                  45

Ala Thr Ser Asp Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser His Pro Pro Thr
                85                  90                  95

Phe Gly Gly Gly Thr Lys Leu Glu Ile Arg
            100                 105

<210> SEQ ID NO 48
<211> LENGTH: 318
<212> TYPE: DNA
<213> ORGANISM: Artificial
<220> FEATURE:
<223> OTHER INFORMATION: Synthetic

<400> SEQUENCE: 48
caatttgttc tctcccagtc tccagcaatc ctgtctgcat ctcccgggga gatgctcaca      60
atgacttgca gggccagctc aagtgtaagt tatatgaact ggtatcagca gaagccagga     120
tcttccccca aaccctggat ttatgccaca tccgacctgg cttctggagt ccctgctcgc     180
ttcagtggca gtgggtctgg gacctcttat tctctcacaa tcagcagagt ggaggctgaa     240
gatgctgcca cttattactg ccagcagtgg agtagtcacc cacccacgtt cggagggggg     300
accaagctgg aaataaga                                                    318

<210> SEQ ID NO 49
<211> LENGTH: 110
<212> TYPE: PRT

```
<213> ORGANISM: Homo sapiens

<400> SEQUENCE: 49

Met Leu Val Ala Tyr Asp Asn Ala Val Asn Leu Ser Cys Lys Tyr Ser
1               5                   10                  15

Tyr Asn Leu Phe Ser Arg Glu Phe Arg Ala Ser Leu His Lys Gly Leu
            20                  25                  30

Asp Ser Ala Val Glu Val Cys Val Val Tyr Gly Asn Tyr Ser Gln Gln
        35                  40                  45

Leu Gln Val Tyr Ser Lys Thr Gly Phe Asn Cys Asp Gly Lys Leu Gly
    50                  55                  60

Asn Glu Ser Val Thr Phe Tyr Leu Gln Asn Leu Tyr Val Asn Gln Thr
65                  70                  75                  80

Asp Ile Tyr Phe Cys Lys Ile Glu Val Met Tyr Pro Pro Pro Tyr Leu
                85                  90                  95

Asp Asn Glu Lys Ser Asn Gly Thr Ile Ile His Val Lys Gly
            100                 105                 110

<210> SEQ ID NO 50
<211> LENGTH: 16
<212> TYPE: PRT
<213> ORGANISM: Homo sapiens

<400> SEQUENCE: 50

Gly Lys His Leu Cys Pro Ser Pro Leu Phe Pro Gly Pro Ser Lys Pro
1               5                   10                  15

<210> SEQ ID NO 51
<211> LENGTH: 15
<212> TYPE: PRT
<213> ORGANISM: Homo sapiens

<400> SEQUENCE: 51

Lys Gly Lys His Leu Cys Pro Ser Pro Leu Phe Pro Gly Pro Ser
1               5                   10                  15

<210> SEQ ID NO 52
<211> LENGTH: 19
<212> TYPE: PRT
<213> ORGANISM: Homo sapiens

<400> SEQUENCE: 52

His Val Lys Gly Lys His Leu Cys Pro Ser Pro Leu Phe Pro Gly Pro
1               5                   10                  15

Ser Lys Pro

<210> SEQ ID NO 53
<211> LENGTH: 134
<212> TYPE: PRT
<213> ORGANISM: Homo sapiens

<400> SEQUENCE: 53

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60
```

```
Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro
    130

<210> SEQ ID NO 54
<211> LENGTH: 32
<212> TYPE: PRT
<213> ORGANISM: Artificial
<220> FEATURE:
<223> OTHER INFORMATION: Synthetic

<400> SEQUENCE: 54

Asp Tyr Lys Asp Asp Asp Asp Lys Gly Gly Gly Gly Gly His Val Lys
1               5                   10                  15

Gly Lys His Leu Cys Pro Ser Pro Leu Phe Pro Gly Pro Ser Lys Pro
            20                  25                  30

<210> SEQ ID NO 55
<211> LENGTH: 32
<212> TYPE: PRT
<213> ORGANISM: Artificial
<220> FEATURE:
<223> OTHER INFORMATION: Synthetic

<400> SEQUENCE: 55

Asp Tyr Lys Asp Asp Asp Asp Lys Gly Gly Gly Gly Gly His Val Lys
1               5                   10                  15

Gly Lys His Leu Cys Pro Ser Pro Lys Phe Pro Gly Pro Ser Lys Pro
            20                  25                  30

<210> SEQ ID NO 56
<211> LENGTH: 17
<212> TYPE: PRT
<213> ORGANISM: Artificial
<220> FEATURE:
<223> OTHER INFORMATION: Synthetic

<400> SEQUENCE: 56

Gly Lys His Leu Cys Pro Ser Pro Leu Phe Pro Gly Pro Ser Lys Pro
1               5                   10                  15

Lys

<210> SEQ ID NO 57
<211> LENGTH: 716
<212> TYPE: PRT
<213> ORGANISM: Artificial
<220> FEATURE:
<223> OTHER INFORMATION: Synthetic

<400> SEQUENCE: 57

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Ala Ser Ile Asn
            20                  25                  30
```

-continued

```
Ala Met Gly Trp Tyr Arg Gln Ala Pro Gly Ser Gln Arg Glu Leu Val
    35                  40                  45

Ala Ala Ile Ser Gly Gly Gly Asp Thr Tyr Tyr Ala Asp Ser Val Lys
    50                  55                  60

Gly Arg Phe Thr Ile Ser Arg Asp Asn Ala Lys Thr Thr Val Tyr Leu
65                  70                  75                  80

Gln Met Asn Ser Leu Arg Pro Glu Asp Thr Ala Val Tyr Tyr Cys Val
                85                  90                  95

Val Asp Leu Tyr Gly Ser Asp Tyr Trp Asp Trp Gly Gln Gly Thr Gln
            100                 105                 110

Val Thr Val Ser Ser Ala Ala Ala Gly Gly Gly Gly Ser Asp Ala His
        115                 120                 125

Lys Ser Glu Val Ala His Arg Phe Lys Asp Leu Gly Glu Glu Asn Phe
    130                 135                 140

Lys Ala Leu Val Leu Ile Ala Phe Ala Gln Tyr Leu Gln Gln Cys Pro
145                 150                 155                 160

Phe Glu Asp His Val Lys Leu Val Asn Glu Val Thr Glu Phe Ala Lys
                165                 170                 175

Thr Cys Val Ala Asp Glu Ser Ala Glu Asn Cys Asp Lys Ser Leu His
            180                 185                 190

Thr Leu Phe Gly Asp Lys Leu Cys Thr Val Ala Thr Leu Arg Glu Thr
        195                 200                 205

Tyr Gly Glu Met Ala Asp Cys Cys Ala Lys Gln Glu Pro Glu Arg Asn
    210                 215                 220

Glu Cys Phe Leu Gln His Lys Asp Asp Asn Pro Asn Leu Pro Arg Leu
225                 230                 235                 240

Val Arg Pro Glu Val Asp Val Met Cys Thr Ala Phe His Asp Asn Glu
                245                 250                 255

Glu Thr Phe Leu Lys Lys Tyr Leu Tyr Glu Ile Ala Arg Arg His Pro
            260                 265                 270

Tyr Phe Tyr Ala Pro Glu Leu Leu Phe Phe Ala Lys Arg Tyr Lys Ala
        275                 280                 285

Ala Phe Thr Glu Cys Cys Gln Ala Ala Asp Lys Ala Ala Cys Leu Leu
    290                 295                 300

Pro Lys Leu Asp Glu Leu Arg Asp Glu Gly Lys Ala Ser Ser Ala Lys
305                 310                 315                 320

Gln Arg Leu Lys Cys Ala Ser Leu Gln Lys Phe Gly Glu Arg Ala Phe
                325                 330                 335

Lys Ala Trp Ala Val Ala Arg Leu Ser Gln Arg Phe Pro Lys Ala Glu
            340                 345                 350

Phe Ala Glu Val Ser Lys Leu Val Thr Asp Leu Thr Lys Val His Thr
        355                 360                 365

Glu Cys Cys His Gly Asp Leu Leu Glu Cys Ala Asp Asp Arg Ala Asp
    370                 375                 380

Leu Ala Lys Tyr Ile Cys Glu Asn Gln Asp Ser Ile Ser Ser Lys Leu
385                 390                 395                 400

Lys Glu Cys Cys Glu Lys Pro Leu Leu Glu Lys Ser His Cys Ile Ala
                405                 410                 415

Glu Val Glu Asn Asp Glu Met Pro Ala Asp Leu Pro Ser Leu Ala Ala
            420                 425                 430

Asp Phe Val Glu Ser Lys Asp Val Cys Lys Asn Tyr Ala Glu Ala Lys
        435                 440                 445

Asp Val Phe Leu Gly Met Phe Leu Tyr Glu Tyr Ala Arg Arg His Pro
```

-continued

```
            450                 455                 460
Asp Tyr Ser Val Val Leu Leu Leu Arg Leu Ala Lys Thr Tyr Glu Thr
465                 470                 475                 480

Thr Leu Glu Lys Cys Cys Ala Ala Ala Asp Pro His Glu Cys Tyr Ala
                485                 490                 495

Lys Val Phe Asp Glu Phe Lys Pro Leu Val Glu Glu Pro Gln Asn Leu
                500                 505                 510

Ile Lys Gln Asn Cys Glu Leu Phe Glu Gln Leu Gly Glu Tyr Lys Phe
                515                 520                 525

Gln Asn Ala Leu Leu Val Arg Tyr Thr Lys Lys Val Pro Gln Val Ser
                530                 535                 540

Thr Pro Thr Leu Val Glu Val Ser Arg Asn Leu Gly Lys Val Gly Ser
545                 550                 555                 560

Lys Cys Cys Lys His Pro Glu Ala Lys Arg Met Pro Cys Ala Glu Asp
                565                 570                 575

Tyr Leu Ser Val Val Leu Asn Gln Leu Cys Val Leu His Glu Lys Thr
                580                 585                 590

Pro Val Ser Asp Arg Val Thr Lys Cys Cys Thr Glu Ser Leu Val Asn
                595                 600                 605

Arg Arg Pro Cys Phe Ser Ala Leu Glu Val Asp Glu Thr Tyr Val Pro
                610                 615                 620

Lys Glu Phe Asn Ala Glu Thr Phe Thr Phe His Ala Asp Ile Cys Thr
625                 630                 635                 640

Leu Ser Glu Lys Glu Arg Gln Ile Lys Lys Gln Thr Ala Leu Val Glu
                645                 650                 655

Leu Val Lys His Lys Pro Lys Ala Thr Lys Glu Gln Leu Lys Ala Val
                660                 665                 670

Met Asp Asp Phe Ala Ala Phe Val Glu Lys Cys Cys Lys Ala Asp Asp
                675                 680                 685

Lys Glu Thr Cys Phe Ala Glu Glu Gly Lys Lys Leu Val Ala Ala Ser
                690                 695                 700

Gln Ala Ala Leu Gly Leu His His His His His
705                 710                 715

<210> SEQ ID NO 58
<211> LENGTH: 726
<212> TYPE: PRT
<213> ORGANISM: Artificial
<220> FEATURE:
<223> OTHER INFORMATION: Synthetic

<400> SEQUENCE: 58

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Ala Ser Ile Asn
                20                  25                  30

Ala Met Gly Trp Tyr Arg Gln Ala Pro Gly Ser Gln Arg Glu Leu Val
                35                  40                  45

Ala Ala Ile Ser Gly Gly Gly Asp Thr Tyr Tyr Ala Asp Ser Val Lys
                50                  55                  60

Gly Arg Phe Thr Ile Ser Arg Asp Asn Ala Lys Thr Thr Val Tyr Leu
65                  70                  75                  80

Gln Met Asn Ser Leu Arg Pro Glu Asp Thr Ala Val Tyr Tyr Cys Val
                85                  90                  95

Val Asp Leu Tyr Gly Ser Asp Tyr Trp Asp Trp Gly Gln Gly Thr Gln
```

```
            100              105              110
Val Thr Val Ser Ser Ala Ala Ala Gly Gly Gly Gly Ser Gly Gly Gly
            115              120              125

Gly Ser Gly Gly Gly Gly Ser Asp Ala His Lys Ser Glu Val Ala His
        130              135              140

Arg Phe Lys Asp Leu Gly Glu Glu Asn Phe Lys Ala Leu Val Leu Ile
145              150              155              160

Ala Phe Ala Gln Tyr Leu Gln Gln Cys Pro Phe Glu Asp His Val Lys
            165              170              175

Leu Val Asn Glu Val Thr Glu Phe Ala Lys Thr Cys Val Ala Asp Glu
            180              185              190

Ser Ala Glu Asn Cys Asp Lys Ser Leu His Thr Leu Phe Gly Asp Lys
            195              200              205

Leu Cys Thr Val Ala Thr Leu Arg Glu Thr Tyr Gly Glu Met Ala Asp
        210              215              220

Cys Cys Ala Lys Gln Glu Pro Glu Arg Asn Glu Cys Phe Leu Gln His
225              230              235              240

Lys Asp Asp Asn Pro Asn Leu Pro Arg Leu Val Arg Pro Glu Val Asp
            245              250              255

Val Met Cys Thr Ala Phe His Asp Asn Glu Glu Thr Phe Leu Lys Lys
            260              265              270

Tyr Leu Tyr Glu Ile Ala Arg Arg His Pro Tyr Phe Tyr Ala Pro Glu
            275              280              285

Leu Leu Phe Phe Ala Lys Arg Tyr Lys Ala Ala Phe Thr Glu Cys Cys
        290              295              300

Gln Ala Ala Asp Lys Ala Ala Cys Leu Leu Pro Lys Leu Asp Glu Leu
305              310              315              320

Arg Asp Glu Gly Lys Ala Ser Ser Ala Lys Gln Arg Leu Lys Cys Ala
            325              330              335

Ser Leu Gln Lys Phe Gly Glu Arg Ala Phe Lys Ala Trp Ala Val Ala
            340              345              350

Arg Leu Ser Gln Arg Phe Pro Lys Ala Glu Phe Ala Glu Val Ser Lys
            355              360              365

Leu Val Thr Asp Leu Thr Lys Val His Thr Glu Cys Cys His Gly Asp
        370              375              380

Leu Leu Glu Cys Ala Asp Asp Arg Ala Asp Leu Ala Lys Tyr Ile Cys
385              390              395              400

Glu Asn Gln Asp Ser Ile Ser Ser Lys Leu Lys Glu Cys Cys Glu Lys
            405              410              415

Pro Leu Leu Glu Lys Ser His Cys Ile Ala Glu Val Glu Asn Asp Glu
            420              425              430

Met Pro Ala Asp Leu Pro Ser Leu Ala Ala Asp Phe Val Glu Ser Lys
            435              440              445

Asp Val Cys Lys Asn Tyr Ala Glu Ala Lys Asp Val Phe Leu Gly Met
        450              455              460

Phe Leu Tyr Glu Tyr Ala Arg Arg His Pro Asp Tyr Ser Val Val Leu
465              470              475              480

Leu Leu Arg Leu Ala Lys Thr Tyr Glu Thr Thr Leu Glu Lys Cys Cys
            485              490              495

Ala Ala Ala Asp Pro His Glu Cys Tyr Ala Lys Val Phe Asp Glu Phe
            500              505              510

Lys Pro Leu Val Glu Glu Pro Gln Asn Leu Ile Lys Gln Asn Cys Glu
            515              520              525
```

-continued

```
Leu Phe Glu Gln Leu Gly Glu Tyr Lys Phe Gln Asn Ala Leu Leu Val
    530             535             540

Arg Tyr Thr Lys Lys Val Pro Gln Val Ser Thr Pro Thr Leu Val Glu
545             550             555             560

Val Ser Arg Asn Leu Gly Lys Val Gly Ser Lys Cys Cys Lys His Pro
            565             570             575

Glu Ala Lys Arg Met Pro Cys Ala Glu Asp Tyr Leu Ser Val Val Leu
            580             585             590

Asn Gln Leu Cys Val Leu His Glu Lys Thr Pro Val Ser Asp Arg Val
            595             600             605

Thr Lys Cys Cys Thr Glu Ser Leu Val Asn Arg Arg Pro Cys Phe Ser
    610             615             620

Ala Leu Glu Val Asp Glu Thr Tyr Val Pro Lys Glu Phe Asn Ala Glu
625             630             635             640

Thr Phe Thr Phe His Ala Asp Ile Cys Thr Leu Ser Glu Lys Glu Arg
            645             650             655

Gln Ile Lys Lys Gln Thr Ala Leu Val Glu Leu Val Lys His Lys Pro
            660             665             670

Lys Ala Thr Lys Glu Gln Leu Lys Ala Val Met Asp Asp Phe Ala Ala
            675             680             685

Phe Val Glu Lys Cys Cys Lys Ala Asp Asp Lys Glu Thr Cys Phe Ala
    690             695             700

Glu Glu Gly Lys Lys Leu Val Ala Ala Ser Gln Ala Ala Leu Gly Leu
705             710             715             720

His His His His His His
            725
```

```
<210> SEQ ID NO 59
<211> LENGTH: 746
<212> TYPE: PRT
<213> ORGANISM: Artificial
<220> FEATURE:
<223> OTHER INFORMATION: Synthetic

<400> SEQUENCE: 59

Glu Val Gln Leu Val Glu Ser Gly Gly Gly Leu Val Gln Ala Gly Glu
1               5               10              15

Ser Leu Arg Leu Ser Cys Ala Ala Ser Gly Ser Ile Ala Ser Ile Asn
            20              25              30

Ala Met Gly Trp Tyr Arg Gln Ala Pro Gly Ser Gln Arg Glu Leu Val
            35              40              45

Ala Ala Ile Ser Gly Gly Gly Asp Thr Tyr Tyr Ala Asp Ser Val Lys
    50              55              60

Gly Arg Phe Thr Ile Ser Arg Asp Asn Ala Lys Thr Thr Val Tyr Leu
65              70              75              80

Gln Met Asn Ser Leu Arg Pro Glu Asp Thr Ala Val Tyr Tyr Cys Val
            85              90              95

Val Asp Leu Tyr Gly Ser Asp Tyr Trp Asp Trp Gly Gln Gly Thr Gln
            100             105             110

Val Thr Val Ser Ser Ala Ala Ala Gly Gly Gly Gly Ser Gly Gly Gly
            115             120             125

Gly Ser Gly Gly Gly Gly Ser Gly Gly Gly Gly Ser Gly Gly Gly Gly
    130             135             140

Ser Gly Gly Gly Gly Ser Gly Gly Gly Gly Ser Asp Ala His Lys Ser
145             150             155             160
```

-continued

```
Glu Val Ala His Arg Phe Lys Asp Leu Gly Glu Glu Asn Phe Lys Ala
                165                 170                 175

Leu Val Leu Ile Ala Phe Ala Gln Tyr Leu Gln Gln Cys Pro Phe Glu
                180                 185                 190

Asp His Val Lys Leu Val Asn Glu Val Thr Glu Phe Ala Lys Thr Cys
                195                 200                 205

Val Ala Asp Glu Ser Ala Glu Asn Cys Asp Lys Ser Leu His Thr Leu
        210                 215                 220

Phe Gly Asp Lys Leu Cys Thr Val Ala Thr Leu Arg Glu Thr Tyr Gly
225                 230                 235                 240

Glu Met Ala Asp Cys Cys Ala Lys Gln Glu Pro Glu Arg Asn Glu Cys
                245                 250                 255

Phe Leu Gln His Lys Asp Asp Asn Pro Asn Leu Pro Arg Leu Val Arg
                260                 265                 270

Pro Glu Val Asp Val Met Cys Thr Ala Phe His Asp Asn Glu Glu Thr
                275                 280                 285

Phe Leu Lys Lys Tyr Leu Tyr Glu Ile Ala Arg Arg His Pro Tyr Phe
        290                 295                 300

Tyr Ala Pro Glu Leu Leu Phe Phe Ala Lys Arg Tyr Lys Ala Ala Phe
305                 310                 315                 320

Thr Glu Cys Cys Gln Ala Ala Asp Lys Ala Ala Cys Leu Leu Pro Lys
                325                 330                 335

Leu Asp Glu Leu Arg Asp Glu Gly Lys Ala Ser Ser Ala Lys Gln Arg
                340                 345                 350

Leu Lys Cys Ala Ser Leu Gln Lys Phe Gly Glu Arg Ala Phe Lys Ala
                355                 360                 365

Trp Ala Val Ala Arg Leu Ser Gln Arg Phe Pro Lys Ala Glu Phe Ala
        370                 375                 380

Glu Val Ser Lys Leu Val Thr Asp Leu Thr Lys Val His Thr Glu Cys
385                 390                 395                 400

Cys His Gly Asp Leu Leu Glu Cys Ala Asp Asp Arg Ala Asp Leu Ala
                405                 410                 415

Lys Tyr Ile Cys Glu Asn Gln Asp Ser Ile Ser Ser Lys Leu Lys Glu
                420                 425                 430

Cys Cys Glu Lys Pro Leu Leu Glu Lys Ser His Cys Ile Ala Glu Val
                435                 440                 445

Glu Asn Asp Glu Met Pro Ala Asp Leu Pro Ser Leu Ala Ala Asp Phe
        450                 455                 460

Val Glu Ser Lys Asp Val Cys Lys Asn Tyr Ala Glu Ala Lys Asp Val
465                 470                 475                 480

Phe Leu Gly Met Phe Leu Tyr Glu Tyr Ala Arg Arg His Pro Asp Tyr
                485                 490                 495

Ser Val Val Leu Leu Leu Arg Leu Ala Lys Thr Tyr Glu Thr Thr Leu
                500                 505                 510

Glu Lys Cys Cys Ala Ala Ala Asp Pro His Glu Cys Tyr Ala Lys Val
                515                 520                 525

Phe Asp Glu Phe Lys Pro Leu Val Glu Glu Pro Gln Asn Leu Ile Lys
        530                 535                 540

Gln Asn Cys Glu Leu Phe Glu Gln Leu Gly Glu Tyr Lys Phe Gln Asn
545                 550                 555                 560

Ala Leu Leu Val Arg Tyr Thr Lys Lys Val Pro Gln Val Ser Thr Pro
                565                 570                 575
```

```
Thr Leu Val Glu Val Ser Arg Asn Leu Gly Lys Val Gly Ser Lys Cys
             580                 585                 590

Cys Lys His Pro Glu Ala Lys Arg Met Pro Cys Ala Glu Asp Tyr Leu
             595                 600             605

Ser Val Val Leu Asn Gln Leu Cys Val Leu His Glu Lys Thr Pro Val
             610                 615             620

Ser Asp Arg Val Thr Lys Cys Cys Thr Glu Ser Leu Val Asn Arg Arg
625                         630             635                 640

Pro Cys Phe Ser Ala Leu Glu Val Asp Glu Thr Tyr Val Pro Lys Glu
                 645                 650             655

Phe Asn Ala Glu Thr Phe Thr Phe His Ala Asp Ile Cys Thr Leu Ser
             660                 665             670

Glu Lys Glu Arg Gln Ile Lys Lys Gln Thr Ala Leu Val Glu Leu Val
             675                 680             685

Lys His Lys Pro Lys Ala Thr Lys Glu Gln Leu Lys Ala Val Met Asp
         690                 695             700

Asp Phe Ala Ala Phe Val Glu Lys Cys Cys Lys Ala Asp Asp Lys Glu
705                 710                 715                 720

Thr Cys Phe Ala Glu Glu Gly Lys Lys Leu Val Ala Ala Ser Gln Ala
                 725                 730             735

Ala Leu Gly Leu His His His His His His
             740                 745

<210> SEQ ID NO 60
<211> LENGTH: 249
<212> TYPE: PRT
<213> ORGANISM: Artificial
<220> FEATURE:
<223> OTHER INFORMATION: Synthetic

<400> SEQUENCE: 60

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Ala Ser Ile Asn
             20                  25                  30

Ala Met Gly Trp Tyr Arg Gln Ala Pro Gly Ser Gln Arg Glu Leu Val
             35                  40                  45

Ala Ala Ile Ser Gly Gly Gly Asp Thr Tyr Tyr Ala Asp Ser Val Lys
         50                  55                  60

Gly Arg Phe Thr Ile Ser Arg Asp Asn Ala Lys Thr Thr Val Tyr Leu
65                  70                  75                  80

Gln Met Asn Ser Leu Arg Pro Glu Asp Thr Ala Val Tyr Tyr Cys Val
                 85                  90                  95

Val Asp Leu Tyr Gly Ser Asp Tyr Trp Asp Trp Gly Gln Gly Thr Gln
             100                 105                 110

Val Thr Val Ser Ser Ala Ala Ala Gly Gly Gly Gly Ser Glu Val Gln
             115                 120                 125

Leu Val Glu Ser Gly Gly Gly Leu Val Gln Pro Gly Asn Ser Leu Arg
         130                 135                 140

Leu Ser Cys Ala Ala Ser Gly Phe Thr Phe Ser Ser Phe Gly Met Ser
145                 150                 155                 160

Trp Val Arg Gln Ala Pro Gly Lys Gly Leu Glu Trp Val Ser Ser Ile
                 165                 170                 175

Ser Gly Ser Gly Ser Asp Thr Leu Tyr Ala Asp Ser Val Lys Gly Arg
             180                 185                 190
```

```
Phe Thr Ile Ser Arg Asp Asn Ala Lys Thr Thr Leu Tyr Leu Gln Met
        195                 200                 205

Asn Ser Leu Arg Pro Glu Asp Thr Ala Val Tyr Tyr Cys Thr Ile Gly
    210                 215                 220

Gly Ser Leu Ser Arg Ser Ser Gln Gly Thr Leu Val Thr Val Ser Ser
225                 230                 235                 240

Ala Ala Ala His His His His His His
                245
```

```
<210> SEQ ID NO 61
<211> LENGTH: 259
<212> TYPE: PRT
<213> ORGANISM: Artificial
<220> FEATURE:
<223> OTHER INFORMATION: Synthetic

<400> SEQUENCE: 61

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Ala Ser Ile Asn
            20                  25                  30

Ala Met Gly Trp Tyr Arg Gln Ala Pro Gly Ser Gln Arg Glu Leu Val
        35                  40                  45

Ala Ala Ile Ser Gly Gly Gly Asp Thr Tyr Tyr Ala Asp Ser Val Lys
    50                  55                  60

Gly Arg Phe Thr Ile Ser Arg Asp Asn Ala Lys Thr Thr Val Tyr Leu
65                  70                  75                  80

Gln Met Asn Ser Leu Arg Pro Glu Asp Thr Ala Val Tyr Tyr Cys Val
            85                  90                  95

Val Asp Leu Tyr Gly Ser Asp Tyr Trp Asp Trp Gly Gln Gly Thr Gln
            100                 105                 110

Val Thr Val Ser Ser Ala Ala Ala Gly Gly Gly Gly Ser Gly Gly Gly
        115                 120                 125

Gly Ser Gly Gly Gly Gly Ser Glu Val Gln Leu Val Glu Ser Gly Gly
    130                 135                 140

Gly Leu Val Gln Pro Gly Asn Ser Leu Arg Leu Ser Cys Ala Ala Ser
145                 150                 155                 160

Gly Phe Thr Phe Ser Ser Phe Gly Met Ser Trp Val Arg Gln Ala Pro
            165                 170                 175

Gly Lys Gly Leu Glu Trp Val Ser Ser Ile Ser Gly Ser Gly Ser Asp
            180                 185                 190

Thr Leu Tyr Ala Asp Ser Val Lys Gly Arg Phe Thr Ile Ser Arg Asp
        195                 200                 205

Asn Ala Lys Thr Thr Leu Tyr Leu Gln Met Asn Ser Leu Arg Pro Glu
    210                 215                 220

Asp Thr Ala Val Tyr Tyr Cys Thr Ile Gly Gly Ser Leu Ser Arg Ser
225                 230                 235                 240

Ser Gln Gly Thr Leu Val Thr Val Ser Ser Ala Ala Ala His His His
            245                 250                 255

His His His
```

```
<210> SEQ ID NO 62
<211> LENGTH: 279
<212> TYPE: PRT
<213> ORGANISM: Artificial
<220> FEATURE:
<223> OTHER INFORMATION: Synthetic
```

```
<400> SEQUENCE: 62

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Ala Ser Ile Asn
            20                  25                  30

Ala Met Gly Trp Tyr Arg Gln Ala Pro Gly Ser Gln Arg Glu Leu Val
        35                  40                  45

Ala Ala Ile Ser Gly Gly Gly Asp Thr Tyr Tyr Ala Asp Ser Val Lys
    50                  55                  60

Gly Arg Phe Thr Ile Ser Arg Asp Asn Ala Lys Thr Thr Val Tyr Leu
65                  70                  75                  80

Gln Met Asn Ser Leu Arg Pro Glu Asp Thr Ala Val Tyr Tyr Cys Val
            85                  90                  95

Val Asp Leu Tyr Gly Ser Asp Tyr Trp Asp Trp Gly Gln Gly Thr Gln
            100                 105                 110

Val Thr Val Ser Ser Ala Ala Ala Gly Gly Gly Gly Ser Gly Gly Gly
            115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Pro Gly Asn Ser Leu Arg Leu Ser
                165                 170                 175

Cys Ala Ala Ser Gly Phe Thr Phe Ser Ser Phe Gly Met Ser Trp Val
                180                 185                 190

Arg Gln Ala Pro Gly Lys Gly Leu Glu Trp Val Ser Ser Ile Ser Gly
            195                 200                 205

Ser Gly Ser Asp Thr Leu Tyr Ala Asp Ser Val Lys Gly Arg Phe Thr
    210                 215                 220

Ile Ser Arg Asp Asn Ala Lys Thr Thr Leu Tyr Leu Gln Met Asn Ser
225                 230                 235                 240

Leu Arg Pro Glu Asp Thr Ala Val Tyr Tyr Cys Thr Ile Gly Gly Ser
                245                 250                 255

Leu Ser Arg Ser Ser Gln Gly Thr Leu Val Thr Val Ser Ser Ala Ala
                260                 265                 270

Ala His His His His His His
        275

<210> SEQ ID NO 63
<211> LENGTH: 727
<212> TYPE: PRT
<213> ORGANISM: Artificial
<220> FEATURE:
<223> OTHER INFORMATION: Synthetic

<400> SEQUENCE: 63

Glu Val Gln Leu Val Glu Ser Gly Gly Gly Leu Val Gln Ala Gly Glu
1               5                   10                  15

Ser Leu Arg Leu Ser Cys Ala Ala Ser Gly Ser Ile Ala Ser Ile Asn
            20                  25                  30

Ala Met Gly Trp Tyr Arg Gln Ala Pro Gly Ser Gln Arg Glu Leu Val
        35                  40                  45

Ala Ala Ile Ser Gly Gly Gly Asp Thr Tyr Tyr Ala Asp Ser Val Lys
    50                  55                  60
```

```
Gly Arg Phe Thr Ile Ser Arg Asp Asn Ala Lys Thr Thr Val Tyr Leu
65              70                  75                  80

Gln Met Asn Ser Leu Arg Pro Glu Asp Thr Ala Val Tyr Tyr Cys Val
                85                  90                  95

Val Asp Leu Tyr Gly Ser Asp Tyr Trp Asp Trp Gly Gln Gly Thr Gln
            100                 105                 110

Val Thr Val Ser Ser Ala Ala Ala Ser Ala Glu Ala Ala Ala Lys Glu
            115                 120                 125

Ala Ala Ala Lys Glu Ala Ala Ala Lys Ala Ala Ala Gly Ser Asp Ala
        130                 135                 140

His Lys Ser Glu Val Ala His Arg Phe Lys Asp Leu Gly Glu Glu Asn
145                 150                 155                 160

Phe Lys Ala Leu Val Leu Ile Ala Phe Ala Gln Tyr Leu Gln Gln Cys
                165                 170                 175

Pro Phe Glu Asp His Val Lys Leu Val Asn Glu Val Thr Glu Phe Ala
                180                 185                 190

Lys Thr Cys Val Ala Asp Glu Ser Ala Glu Asn Cys Asp Lys Ser Leu
                195                 200                 205

His Thr Leu Phe Gly Asp Lys Leu Cys Thr Val Ala Thr Leu Arg Glu
        210                 215                 220

Thr Tyr Gly Glu Met Ala Asp Cys Cys Ala Lys Gln Glu Pro Glu Arg
225                 230                 235                 240

Asn Glu Cys Phe Leu Gln His Lys Asp Asp Asn Pro Asn Leu Pro Arg
                245                 250                 255

Leu Val Arg Pro Glu Val Asp Val Met Cys Thr Ala Phe His Asp Asn
                260                 265                 270

Glu Glu Thr Phe Leu Lys Lys Tyr Leu Tyr Glu Ile Ala Arg Arg His
        275                 280                 285

Pro Tyr Phe Tyr Ala Pro Glu Leu Leu Phe Phe Ala Lys Arg Tyr Lys
        290                 295                 300

Ala Ala Phe Thr Glu Cys Cys Gln Ala Ala Asp Lys Ala Ala Cys Leu
305                 310                 315                 320

Leu Pro Lys Leu Asp Glu Leu Arg Asp Glu Gly Lys Ala Ser Ser Ala
                325                 330                 335

Lys Gln Arg Leu Lys Cys Ala Ser Leu Gln Lys Phe Gly Glu Arg Ala
                340                 345                 350

Phe Lys Ala Trp Ala Val Ala Arg Leu Ser Gln Arg Phe Pro Lys Ala
                355                 360                 365

Glu Phe Ala Glu Val Ser Lys Leu Val Thr Asp Leu Thr Lys Val His
        370                 375                 380

Thr Glu Cys Cys His Gly Asp Leu Leu Glu Cys Ala Asp Asp Arg Ala
385                 390                 395                 400

Asp Leu Ala Lys Tyr Ile Cys Glu Asn Gln Asp Ser Ile Ser Ser Lys
                405                 410                 415

Leu Lys Glu Cys Cys Glu Lys Pro Leu Leu Glu Lys Ser His Cys Ile
                420                 425                 430

Ala Glu Val Glu Asn Asp Glu Met Pro Ala Asp Leu Pro Ser Leu Ala
                435                 440                 445

Ala Asp Phe Val Glu Ser Lys Asp Val Cys Lys Asn Tyr Ala Glu Ala
        450                 455                 460

Lys Asp Val Phe Leu Gly Met Phe Leu Tyr Glu Tyr Ala Arg Arg His
465                 470                 475                 480

Pro Asp Tyr Ser Val Val Leu Leu Leu Arg Leu Ala Lys Thr Tyr Glu
```

-continued

```
                 485              490              495
Thr Thr Leu Glu Lys Cys Cys Ala Ala Ala Asp Pro His Glu Cys Tyr
            500              505              510

Ala Lys Val Phe Asp Glu Phe Lys Pro Leu Val Glu Glu Pro Gln Asn
            515              520              525

Leu Ile Lys Gln Asn Cys Glu Leu Phe Glu Gln Leu Gly Glu Tyr Lys
            530              535              540

Phe Gln Asn Ala Leu Leu Val Arg Tyr Thr Lys Lys Val Pro Gln Val
545              550              555              560

Ser Thr Pro Thr Leu Val Glu Val Ser Arg Asn Leu Gly Lys Val Gly
            565              570              575

Ser Lys Cys Cys Lys His Pro Glu Ala Lys Arg Met Pro Cys Ala Glu
            580              585              590

Asp Tyr Leu Ser Val Val Leu Asn Gln Leu Cys Val Leu His Glu Lys
            595              600              605

Thr Pro Val Ser Asp Arg Val Thr Lys Cys Cys Thr Glu Ser Leu Val
            610              615              620

Asn Arg Arg Pro Cys Phe Ser Ala Leu Glu Val Asp Glu Thr Tyr Val
625              630              635              640

Pro Lys Glu Phe Asn Ala Glu Thr Phe Thr Phe His Ala Asp Ile Cys
            645              650              655

Thr Leu Ser Glu Lys Glu Arg Gln Ile Lys Lys Gln Thr Ala Leu Val
            660              665              670

Glu Leu Val Lys His Lys Pro Lys Ala Thr Lys Glu Gln Leu Lys Ala
            675              680              685

Val Met Asp Asp Phe Ala Ala Phe Val Glu Lys Cys Cys Lys Ala Asp
            690              695              700

Asp Lys Glu Thr Cys Phe Ala Glu Glu Gly Lys Lys Leu Val Ala Ala
705              710              715              720

Ser Gln Ala Ala Leu Gly Leu
                725
```

```
<210> SEQ ID NO 64
<211> LENGTH: 737
<212> TYPE: PRT
<213> ORGANISM: Artificial
<220> FEATURE:
<223> OTHER INFORMATION: Synthetic

<400> SEQUENCE: 64

Glu Val Gln Leu Val Glu Ser Gly Gly Gly Leu Val Gln Ala Gly Glu
1               5               10              15

Ser Leu Arg Leu Ser Cys Ala Ala Ser Gly Ser Ile Ala Ser Ile Asn
            20              25              30

Ala Met Gly Trp Tyr Arg Gln Ala Pro Gly Ser Gln Arg Glu Leu Val
            35              40              45

Ala Ala Ile Ser Gly Gly Gly Asp Thr Tyr Tyr Ala Asp Ser Val Lys
            50              55              60

Gly Arg Phe Thr Ile Ser Arg Asp Asn Ala Lys Thr Thr Val Tyr Leu
65              70              75              80

Gln Met Asn Ser Leu Arg Pro Glu Asp Thr Ala Val Tyr Tyr Cys Val
            85              90              95

Val Asp Leu Tyr Gly Ser Asp Tyr Trp Asp Trp Gly Gln Gly Thr Gln
            100             105             110

Val Thr Val Ser Ser Ala Ala Ala Ser Ala Glu Ala Ala Ala Lys Glu
```

-continued

```
            115              120              125

Ala Ala Ala Lys Glu Ala Ala Ala Lys Glu Ala Ala Ala Lys Glu Ala
    130              135              140

Ala Ala Lys Ala Ala Ala Gly Ser Asp Ala His Lys Ser Glu Val Ala
145              150              155              160

His Arg Phe Lys Asp Leu Gly Glu Glu Asn Phe Lys Ala Leu Val Leu
                165              170              175

Ile Ala Phe Ala Gln Tyr Leu Gln Gln Cys Pro Phe Glu Asp His Val
            180              185              190

Lys Leu Val Asn Glu Val Thr Glu Phe Ala Lys Thr Cys Val Ala Asp
            195              200              205

Glu Ser Ala Glu Asn Cys Asp Lys Ser Leu His Thr Leu Phe Gly Asp
    210              215              220

Lys Leu Cys Thr Val Ala Thr Leu Arg Glu Thr Tyr Gly Glu Met Ala
225              230              235              240

Asp Cys Cys Ala Lys Gln Glu Pro Glu Arg Asn Glu Cys Phe Leu Gln
            245              250              255

His Lys Asp Asp Asn Pro Asn Leu Pro Arg Leu Val Arg Pro Glu Val
            260              265              270

Asp Val Met Cys Thr Ala Phe His Asp Asn Glu Glu Thr Phe Leu Lys
            275              280              285

Lys Tyr Leu Tyr Glu Ile Ala Arg Arg His Pro Tyr Phe Tyr Ala Pro
    290              295              300

Glu Leu Leu Phe Phe Ala Lys Arg Tyr Lys Ala Ala Phe Thr Glu Cys
305              310              315              320

Cys Gln Ala Ala Asp Lys Ala Ala Cys Leu Leu Pro Lys Leu Asp Glu
            325              330              335

Leu Arg Asp Glu Gly Lys Ala Ser Ser Ala Lys Gln Arg Leu Lys Cys
            340              345              350

Ala Ser Leu Gln Lys Phe Gly Glu Arg Ala Phe Lys Ala Trp Ala Val
            355              360              365

Ala Arg Leu Ser Gln Arg Phe Pro Lys Ala Glu Phe Ala Glu Val Ser
    370              375              380

Lys Leu Val Thr Asp Leu Thr Lys Val His Thr Glu Cys Cys His Gly
385              390              395              400

Asp Leu Leu Glu Cys Ala Asp Asp Arg Ala Asp Leu Ala Lys Tyr Ile
            405              410              415

Cys Glu Asn Gln Asp Ser Ile Ser Ser Lys Leu Lys Glu Cys Cys Glu
            420              425              430

Lys Pro Leu Leu Glu Lys Ser His Cys Ile Ala Glu Val Glu Asn Asp
            435              440              445

Glu Met Pro Ala Asp Leu Pro Ser Leu Ala Ala Asp Phe Val Glu Ser
    450              455              460

Lys Asp Val Cys Lys Asn Tyr Ala Glu Ala Lys Asp Val Phe Leu Gly
465              470              475              480

Met Phe Leu Tyr Glu Tyr Ala Arg Arg His Pro Asp Tyr Ser Val Val
            485              490              495

Leu Leu Leu Arg Leu Ala Lys Thr Tyr Glu Thr Thr Leu Glu Lys Cys
            500              505              510

Cys Ala Ala Ala Asp Pro His Glu Cys Tyr Ala Lys Val Phe Asp Glu
            515              520              525

Phe Lys Pro Leu Val Glu Glu Pro Gln Asn Leu Ile Lys Gln Asn Cys
    530              535              540
```

-continued

```
Glu Leu Phe Glu Gln Leu Gly Glu Tyr Lys Phe Gln Asn Ala Leu Leu
545             550             555             560

Val Arg Tyr Thr Lys Lys Val Pro Gln Val Ser Thr Pro Thr Leu Val
                565             570             575

Glu Val Ser Arg Asn Leu Gly Lys Val Gly Ser Lys Cys Cys Lys His
            580             585             590

Pro Glu Ala Lys Arg Met Pro Cys Ala Glu Asp Tyr Leu Ser Val Val
        595             600             605

Leu Asn Gln Leu Cys Val Leu His Glu Lys Thr Pro Val Ser Asp Arg
        610             615             620

Val Thr Lys Cys Cys Thr Glu Ser Leu Val Asn Arg Arg Pro Cys Phe
625             630             635             640

Ser Ala Leu Glu Val Asp Glu Thr Tyr Val Pro Lys Glu Phe Asn Ala
            645             650             655

Glu Thr Phe Thr Phe His Ala Asp Ile Cys Thr Leu Ser Glu Lys Glu
            660             665             670

Arg Gln Ile Lys Lys Gln Thr Ala Leu Val Glu Leu Val Lys His Lys
        675             680             685

Pro Lys Ala Thr Lys Glu Gln Leu Lys Ala Val Met Asp Asp Phe Ala
        690             695             700

Ala Phe Val Glu Lys Cys Cys Lys Ala Asp Asp Lys Glu Thr Cys Phe
705             710             715             720

Ala Glu Glu Gly Lys Lys Leu Val Ala Ala Ser Gln Ala Ala Leu Gly
            725             730             735

Leu
```

```
<210> SEQ ID NO 65
<211> LENGTH: 585
<212> TYPE: PRT
<213> ORGANISM: Homo sapiens

<400> SEQUENCE: 65
```

```
Asp Ala His Lys Ser Glu Val Ala His Arg Phe Lys Asp Leu Gly Glu
1               5               10              15

Glu Asn Phe Lys Ala Leu Val Leu Ile Ala Phe Ala Gln Tyr Leu Gln
                20              25              30

Gln Cys Pro Phe Glu Asp His Val Lys Leu Val Asn Glu Val Thr Glu
            35              40              45

Phe Ala Lys Thr Cys Val Ala Asp Glu Ser Ala Glu Asn Cys Asp Lys
        50              55              60

Ser Leu His Thr Leu Phe Gly Asp Lys Leu Cys Thr Val Ala Thr Leu
65              70              75              80

Arg Glu Thr Tyr Gly Glu Met Ala Asp Cys Cys Ala Lys Gln Glu Pro
                85              90              95

Glu Arg Asn Glu Cys Phe Leu Gln His Lys Asp Asp Asn Pro Asn Leu
            100             105             110

Pro Arg Leu Val Arg Pro Glu Val Asp Val Met Cys Thr Ala Phe His
        115             120             125

Asp Asn Glu Glu Thr Phe Leu Lys Lys Tyr Leu Tyr Glu Ile Ala Arg
        130             135             140

Arg His Pro Tyr Phe Tyr Ala Pro Glu Leu Leu Phe Phe Ala Lys Arg
145             150             155             160

Tyr Lys Ala Ala Phe Thr Glu Cys Cys Gln Ala Ala Asp Lys Ala Ala
                165             170             175
```

-continued

```
Cys Leu Leu Pro Lys Leu Asp Glu Leu Arg Asp Glu Gly Lys Ala Ser
            180             185             190

Ser Ala Lys Gln Arg Leu Lys Cys Ala Ser Leu Gln Lys Phe Gly Glu
            195             200             205

Arg Ala Phe Lys Ala Trp Ala Val Ala Arg Leu Ser Gln Arg Phe Pro
            210             215             220

Lys Ala Glu Phe Ala Glu Val Ser Lys Leu Val Thr Asp Leu Thr Lys
225             230             235             240

Val His Thr Glu Cys Cys His Gly Asp Leu Leu Glu Cys Ala Asp Asp
                245             250             255

Arg Ala Asp Leu Ala Lys Tyr Ile Cys Glu Asn Gln Asp Ser Ile Ser
            260             265             270

Ser Lys Leu Lys Glu Cys Cys Glu Lys Pro Leu Leu Glu Lys Ser His
            275             280             285

Cys Ile Ala Glu Val Glu Asn Asp Glu Met Pro Ala Asp Leu Pro Ser
    290             295             300

Leu Ala Ala Asp Phe Val Glu Ser Lys Asp Val Cys Lys Asn Tyr Ala
305             310             315             320

Glu Ala Lys Asp Val Phe Leu Gly Met Phe Leu Tyr Glu Tyr Ala Arg
                325             330             335

Arg His Pro Asp Tyr Ser Val Val Leu Leu Leu Arg Leu Ala Lys Thr
            340             345             350

Tyr Glu Thr Thr Leu Glu Lys Cys Cys Ala Ala Ala Asp Pro His Glu
            355             360             365

Cys Tyr Ala Lys Val Phe Asp Glu Phe Lys Pro Leu Val Glu Glu Pro
    370             375             380

Gln Asn Leu Ile Lys Gln Asn Cys Glu Leu Phe Glu Gln Leu Gly Glu
385             390             395             400

Tyr Lys Phe Gln Asn Ala Leu Leu Val Arg Tyr Thr Lys Lys Val Pro
            405             410             415

Gln Val Ser Thr Pro Thr Leu Val Glu Val Ser Arg Asn Leu Gly Lys
            420             425             430

Val Gly Ser Lys Cys Cys Lys His Pro Glu Ala Lys Arg Met Pro Cys
            435             440             445

Ala Glu Asp Tyr Leu Ser Val Val Leu Asn Gln Leu Cys Val Leu His
    450             455             460

Glu Lys Thr Pro Val Ser Asp Arg Val Thr Lys Cys Cys Thr Glu Ser
465             470             475             480

Leu Val Asn Arg Arg Pro Cys Phe Ser Ala Leu Glu Val Asp Glu Thr
            485             490             495

Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
            515             520             525

Leu Val Glu Leu Val Lys His Lys Pro Lys Ala Thr Lys Glu Gln Leu
    530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
                565             570             575

Ala Ala Ser Gln Ala Ala Leu Gly Leu
            580             585
```

SHEDDING BLOCKING AGENTS WITH INCREASED STABILITY

CROSS REFERENCE TO RELATED APPLICATIONS

This application is a National Phase of PCT Patent Application No. PCT/IL2021/050271 having International filing date of Mar. 11, 2021, which claims the benefit of priority of U.S. Provisional Patent Application No. 62/988, 503, filed Mar. 12, 2020, the contents of which are all incorporated herein by reference in their entirety.

FIELD OF INVENTION

The present invention is in the field of immune regulation and immunotherapy.

BACKGROUND OF THE INVENTION

The adaptive immune system plays a critical role in the regulation and protection against pathogens and cancer cells, mainly by orchestrating the stimulation of antigen specific helper CD4+ and cytotoxic CD8+ T cells. Durable and persistent activation of T cells by antigen presenting cells (APC), involves i) engagement of the T cell receptor (TCR) with peptides presented by major histocompatibility complexes (MHCs) on APC; and ii) co-stimulatory CD28 receptors on T cells binding B7-1 (CD80) and B7-2 (CD86) ligands expressed also by the APC. The biological consequences of CD28 co-stimulation are numerous and include control of the T cell cycle, expansion, differentiation, as well as amplification of TCR stimulation by lowering the threshold needed for achieving immune effector function.

In contrast to the activating co-stimulatory molecule CD28, the structurally homolog, cytotoxic T lymphocyte associated 4 (CTLA-4), is an inhibitory co-stimulatory receptor, with membrane expression driven by the triggering of CD28. Both, CTLA-4 and CD28 are type I trans-membrane proteins. Their extracellular portion is composed with one V-set immunoglobulin super family (Ig-V) domain, which is homo-covalently linked by a cysteine residue located outside the IgV domain in proximity to the trans-membrane region. Despite the resemblance, CTLA-4 and CD28 differ in terms of affinities and quaternary structural arrangements. CTLA-4 was found to have higher binding affinities to B7 molecules, and a different dimerization mode from CD28 resulting in dissimilar stoichiometric binding with the shared ligands. CD28 exhibits a mono-valent binding stoichiometry, while CTLA-4 interacts in a bivalent fashion. Hence, CTLA-4 binds B7 molecules with a much higher affinity and avidity than CD28 and consequently downregulates T cell responses and favors the onset of antigen specific tolerance.

It has been indicated that some co-stimulatory molecules have several physiological forms. Alongside membrane-bound forms, soluble forms have been described that are expressed in naive immune cells, increasing the complexity of T cell biology. The soluble form of CD28 (sCD28) has been ascribed to alternatively spliced gene product as well as active shedding. Active shedding during T cell activation was described in the past as a regulatory mechanism to counteract persistent activation by the proteolysis of adhesion molecules and has now been shown for CD28 as well.

Membrane CD28 (mCD28) has been shown to be proteolytically cleaved to produce sCD28. Inhibition of this cleavage has been proposed as a method of inhibiting sCD28 and thereby inhibiting sCD28-mediated immune suppression. There is therefore a great need for agents that are pharmaceutically viable with long serum half-lives that can block proteolytic cleavage of mCD28.

SUMMARY OF THE INVENTION

The present invention provides agents comprising at least two moieties separated by a linker, wherein a first moiety binds membranal CD28 (mCD28) on the surface of a cell and inhibit proteolytic cleavage of the mCD28 and wherein a second moiety increases stability of the first moiety. Methods of treating and preventing cancer and improving PD-1/PD-L1 based immunotherapy comprising administering the agents are also provided.

According to a first aspect, there is provide an agent comprising at least two moieties separated by a linker, wherein a first moiety binds membranal CD28 (mCD28) on a surface of a cell and inhibits proteolytic cleavage of the mCD28 and wherein a second moiety increases stability of the first moiety.

According to some embodiments, the first moiety, the second moiety, or both are smaller than 100 kilodaltons (kDa).

According to some embodiments, the agent is smaller than 100 kDa.

According to some embodiments, the first moiety, is selected from an antigen binding fragment of an antibody, a Fab fragment, a single chain antibody, a single domain antibody, a small molecule and a peptide that specifically binds to CD28.

According to some embodiments, the first moiety comprises or consists of a single domain antibody.

According to some embodiments, the single domain antibody is a camelid or shark antibody.

According to some embodiments, the first moiety comprises three CDRs wherein:

CDR1 comprises the amino acid sequence set forth in SEQ ID NO: 1 (INAMG),

CDR2 comprises the amino acid sequence as set forth in SEQ ID NO: 2 (AISGGGDTYYADSVKG), CDR3 comprises the amino acid sequence as set forth in SEQ ID NO: 3 (DLYGSDYWD);

CDR1 comprises the amino acid sequence set forth in SEQ ID NO: 4 (INAMA),

CDR2 comprises the amino acid sequence as set forth in SEQ ID NO: 5 (AITSSGSTNYANSVKG), CDR3 comprises the amino acid sequence as set forth in SEQ ID NO: 6 (DEYGSDYWI); or CDR1 comprises the amino acid sequence set forth in SEQ ID NO: 1 (INAMG), CDR2 comprises the amino acid sequence as set forth in SEQ ID NO: 7 (AITSGGSTNYADSVKG), CDR3 comprises the amino acid sequence as set forth in SEQ ID NO: 8 (DLYGEDYWI).

According to some embodiments, the first moiety comprises a sequence selected from a group consisting of:

a.

```
                                    (SEQ ID NO: 9)
EVQLVESGGGLVQAGESLRLSCAASGSIASINAMG

WYRQAPGSQRELVAAISGGGDTYYADSVKGRFTIS

RDNAKTTVYLQMNSLRPEDTAVYYCVVDLYGSDYW

DWGQGTQVTVSS;
```

-continued

```
b.
                                  (SEQ ID NO: 10)
EVQLVESGGGLVQAGGSLRLSCAASGSLFSINAMA

WYRQAPGKQRELVAAITSSGSTNYANSVKGRFTVS

RDNAKNTMYLQMNSLKPEDTAVYYCVVDEYGSDYW

IWGQGTQVTVSS;
and c.
                                  (SEQ ID NO: 11)
QVQLVESGGGLVQAGGSLRLSCAASGSIFSINAMG

WYRQAPGKQRERVAAITSGGSTNYADSVKGRFTIS

RDNAKNTVYLQMNNLEPRDAGVYYCVVDLYGEDYW

IWGQGTQVTVSS.
```

According to some embodiments, the first moiety comprises three heavy chain CDRs (CDR-H) and three light chain CDRs (CDR-L), wherein: CDR-H1 comprises the amino acid sequence set forth in SEQ ID NO: 12 (GFTFSSYYMS), CDR-H2 comprises the amino acid sequence as set forth in SEQ ID NO: 13 (TISDGGDNTYY-AGTVTG), CDR-H3 comprises the amino acid sequence as set forth in SEQ ID NO: 14 (IHWPYYFDS), CDR-L1 comprises the amino acid sequence as set forth in SEQ ID NO: 15 (RASSSVSYMN), CDR-L2 comprises the amino acid sequence as set forth in SEQ ID NO: 16 (ATSDLAS), and CDR-L3 comprises the amino acid sequence as set forth in SEQ ID NO: 17 (QQWSSHPPT).

According to some embodiments, the agent is not a CD28 agonist.

According to some embodiments, the agent is not a CD28 antagonist.

According to some embodiments, the increased stability of the first moiety comprises increasing stability in blood.

According to some embodiments, increasing stability in blood comprises reducing clearance of the first moiety from blood.

According to some embodiments, reducing clearance from blood comprises reducing renal filtration, reducing lysosomal degradation or both.

According to some embodiments, the linker is a rigid peptide linker.

According to some embodiments, the rigid peptide linker comprises a helix motif.

According to some embodiments, the rigid peptide linker comprises at least 15 amino acids.

According to some embodiments, the rigid peptide linker comprises at most 30 amino acids.

According to some embodiments, the linker comprises at least one cysteine residue.

According to some embodiments, the at least one cysteine is a C-terminal cysteine.

According to some embodiments, the second moiety is polyethylene glycol (PEG) and is attached to the cysteine via a thiol linkage.

According to some embodiments, the second moiety is PEG and the PEG is conjugated within 10 amino acids of a C-terminus of the first moiety.

According to some embodiments, the linker is a peptide linker and PEG is conjugated to an amino acid of the peptide linker.

According to some embodiments, the PEG is linear or branched PEG comprising a size from 2000-40,000 Daltons (Da).

According to some embodiments, the second moiety comprises or consists of a human serum albumin (HSA) polypeptide.

According to some embodiments, the second moiety comprises or consists of an HSA binding polypeptide.

According to some embodiments, the HSA binding polypeptide is a single domain antibody.

According to some embodiments, the single domain antibody comprises or consists of the sequence:

```
                                  (SEQ ID NO: 19)
EVQLVESGGGLVQPGNSLRLSCAASGFTFSSFGMSWVRQAPGKGLEWVSS

ISGSGSDTLYADSVKGRFTISRDNAKTTLYLQMNSLRPEDTAVYYCTIGG

SLSRSSQGTLVTVSSAAA.
```

According to some embodiments, a C-terminus of the first moiety is linked to the linker and an N-terminus of the second moiety is linked to the linker.

According to some embodiments, a C-terminus of the first moiety is linked to an N-terminus of the linker and an N-terminus of the second moiety is linked to a C-terminus of the linker.

According to some embodiments, the agent comprises or consist of an amino acid sequence selected from SEQ ID NO: 63 and 64.

According to some embodiments, the agent comprises an amino acid sequence of SEQ ID NO: 36 and comprises irreversible conjugating a PEG moiety to an amino acid residue within 10 amino acids of a C-terminus of the first moiety.

According to some embodiments, the agent comprises an amino acid sequence of SEQ ID NO: 36 and comprises reversible conjugating a PEG moiety to an amino acid residue within 10 amino acids of a C-terminus of the first moiety.

According to some embodiments, the PEG is linear or branched PEG comprising a size from 2000-40,000 Daltons (Da).

According to another aspect, there is provided a nucleic acid molecule encoding an agent of the invention.

According to another aspect, there is provided an expression vector comprising a nucleic acid molecule of the invention.

According to another aspect, there is provided a method of generating an agent of the invention, the method comprising at least one of:

a. obtaining a first moiety that binds mCD28 on a cell surface and inhibits proteolytic cleavage of the mCD28;

b. linking the first moiety to a second moiety by a linker to produce a linked agent and testing binding of the linked agent to mCD28 on a surface of a cell and inhibition of proteolytic cleavage of the mCD28; and c. selecting a linked agent that binds mCD28 on a cell surface and inhibits proteolytic cleavage of the mCD28; and d. culturing a host cell comprising one or more vectors comprising a nucleic acid sequence encoding an agent, wherein the nucleic acid sequence is that of an agent that was selected by:

i. obtaining a first moiety that binds mCD28 on a cell surface and inhibits proteolytic cleavage of the mCD28;

ii. linking the first moiety to a second moiety by a linker to produce a linked agent and testing binding of the linked agent to mCD28 on a surface of a cell and inhibition of proteolytic cleavage of the mCD28; and iii. selecting a linked agent that binds mCD28 on a cell surface and inhibits proteolytic cleavage of the mCD28;

thereby generating an agent of the invention.

According to some embodiments, the method further comprises assaying mCD28 downstream signaling in the presence of the linked agent and selecting at least one linked agent that neither substantially agonizes nor substantially antagonizes mCD28 signaling.

According to some embodiments, the method further comprises assaying stability of the linked agent in blood and selecting at least one linked agent comprising an increased stability as compared to the first moiety in blood.

According to another aspect, there is provided an agent produced by a method of the invention.

According to another aspect, there is provided a pharmaceutical composition comprising an agent of the invention, and a pharmaceutically acceptable carrier, excipient or adjuvant.

According to another aspect, there is provided a method of decreasing soluble CD28 (sCD28) levels in a subject in need thereof, the method comprising administering an agent of the invention or a pharmaceutical composition of the invention, thereby decreasing sCD28 in a subject.

According to another aspect, there is provided a method of treating and/or preventing cancer in a subject in need thereof, the method comprising administering an agent of the invention or a pharmaceutical composition of the invention, thereby treating and/or preventing cancer in a subject.

According to another aspect, there is provided a method of improving PD-1 and/or PD-L1 based immunotherapy in a subject in need thereof, the method comprising administering an agent of the invention or a pharmaceutical composition of the invention, thereby improving PD-1 and/or PD-L1 based immunotherapy in a subject.

According to some embodiments, the subject suffers from cancer.

According to some embodiments, the method does not degrade mCD28, decrease mCD28-mediated immune cell activation, or activate mCD28-mediated immune cell activation.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A-1C. (1A) Line graphs showing antigen binding by serial dilution of clone M9 to the BSA conjugated CD28 stalk region dimeric peptide (right) and recombinant human CD28 protein (left). Antigens were immobilized on maxisorp ELISA plates. Serial dilution of clone M9 was performed and detection of bound antibody was done with donkey anti mouse IgG (H&L)-HRP and development with

6

TMB. (1B) Bar graphs of ELISA detection of recombinant human sCD28 (left) and sCD28 shed from human PBMCs activated with SEB (right). The ELISA used antibody #3 as a positive control (2 μg/mL, grey bars), irrelevant antibody M39 as a negative control (10 μg/mL, dark grey bars) and anti-cleavage antibody M9 (10 μg/mL, black bar). Detection of recombinant CD28 or shed CD28 was done by using ELISA kit detection antibody conjugated to HRP (0.5 μg/mL). (1C) Histograms showing binding of antibody M9 (upper) and control antibody CD28.2 (lower) at fixed concentration of 10 μg/mL (black histograms) to human CD28 expressed in mouse HEK293 cells. Polyclonal mouse IgG was used as negative control (10 μg/mL) and is depict in grey histograms. Detection was done by incubation with a secondary Alexa Fluor 647-conjugated goat anti-mouse.

Figures 2, 3:
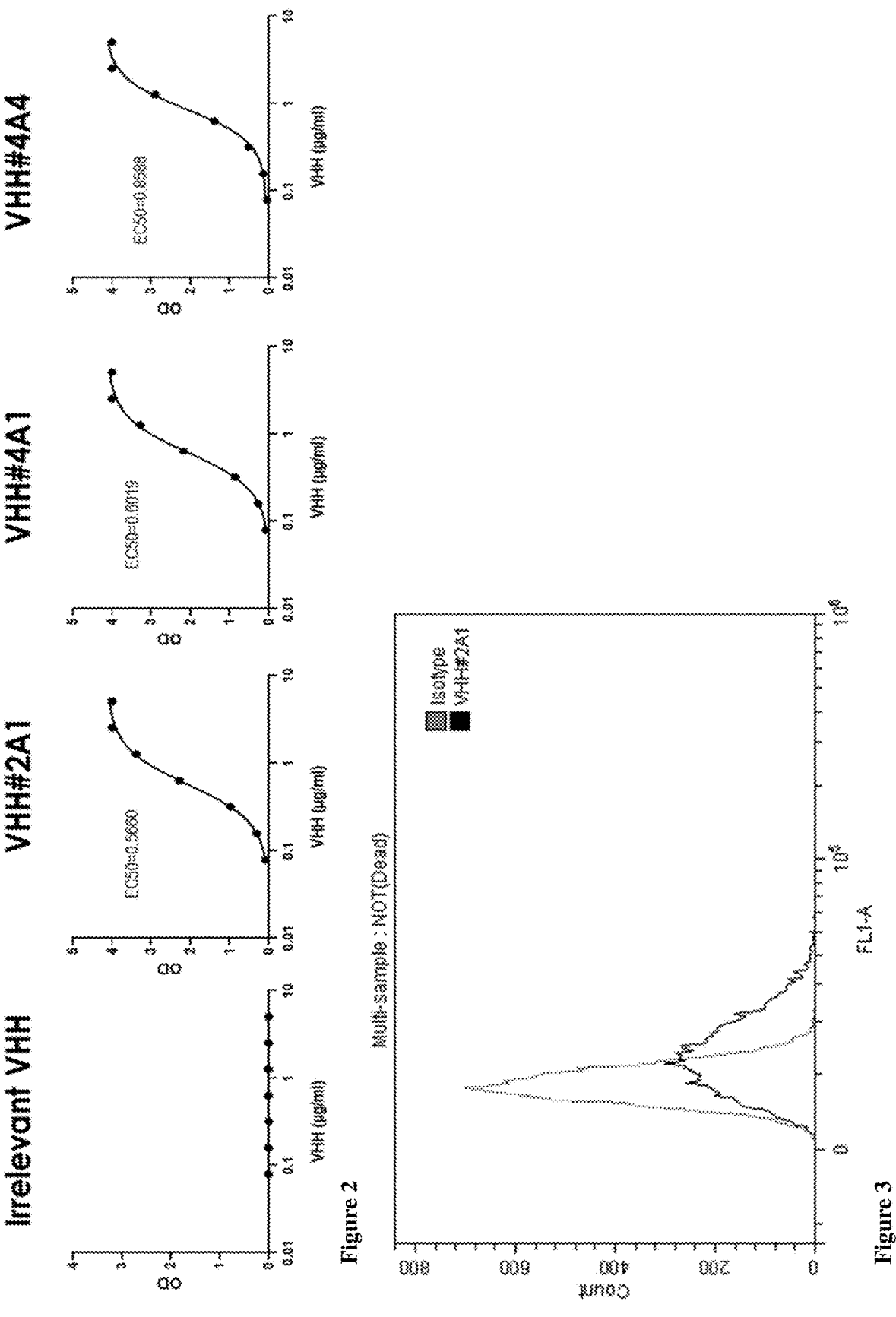

FIG. 2. Binding to Human CD28 stalk region sequence by ELISA. Analysis of antigen binding by serial dilution of different VHH clones. Biotin conjugated CD28 stalk region dimeric peptide serving as antigen was immobilized on neutravidin coated ELISA maxi-sorb plates. Serial dilution of VHH clones was performed and detection of bound VHH was done with anti His tag-HRP conjugated antibody and development was done with TMB.

FIG. 3. Binding of VHH #2A1 to membranal human CD28. FITC conjugated VHH clone 2A1 (50 μg/mL, black histogram) and FITC conjugated isotype control (mIgG, 50 μg/mL, grey histogram) were incubated with HEK cells overexpressing human CD28. Binding was evaluated by FACS analysis.

Figure 4:
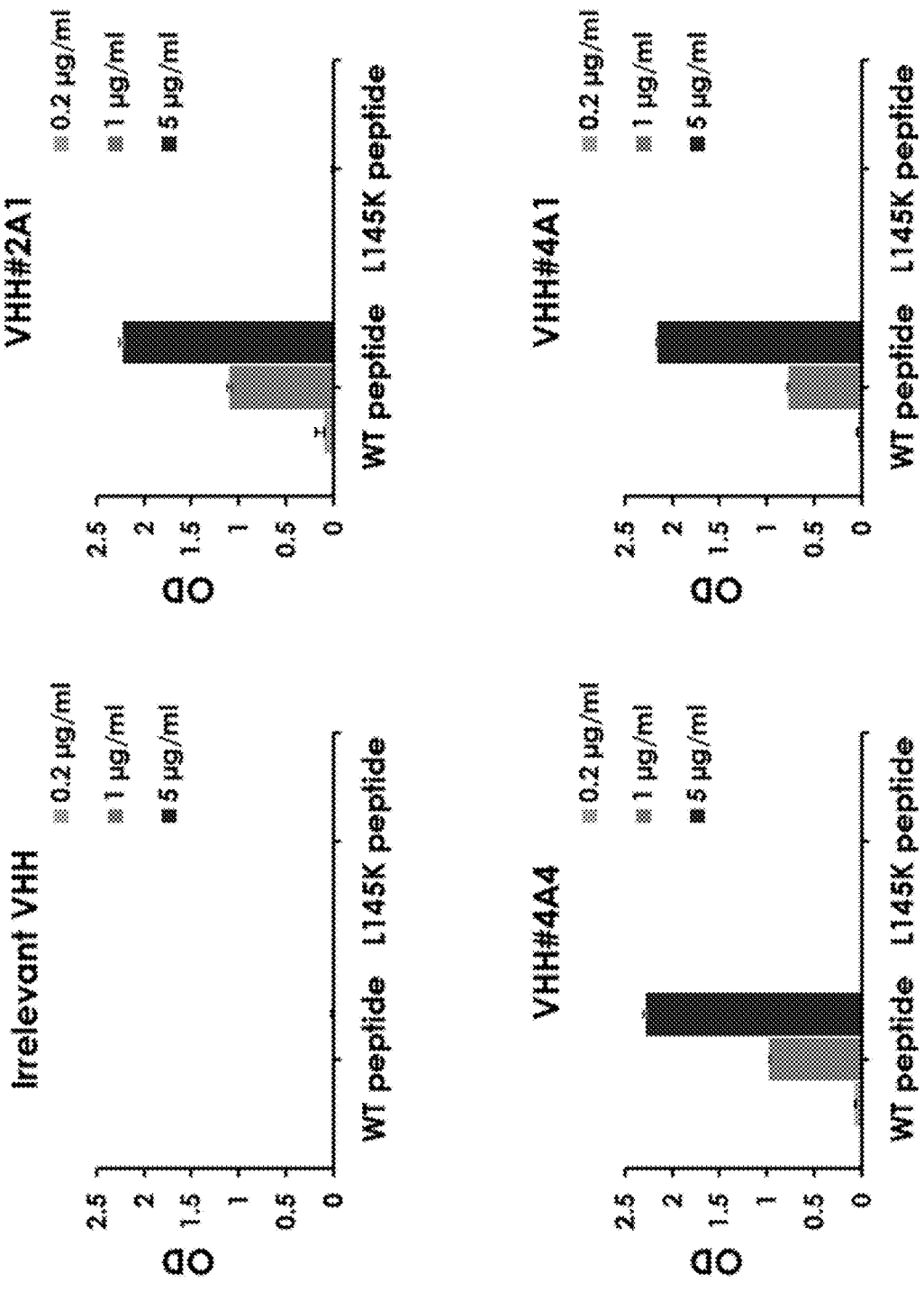

FIG. 4. Anti CD28 stalk region VHH clones 2A1, 4A1 and 4A4 bind specifically to MMP cleavage site of human CD28. Comparison of the specific binding of VHH clones either to human CD28 stalk region WT sequence or to L145K mutated sequence by direct ELISA. Biotin conjugated wild-type or L145K CD28 stalk region dimeric peptides were immobilized on neutravidin coated ELISA maxi-sorb plates. A dilution series of VHH clones (0.2-5 μg/mL) and an irrelevant VHH clone (top left chart) was performed and detection of bound VHH was done with anti His tag-HRP conjugated antibody and development was done with TMB.

Figure 5:
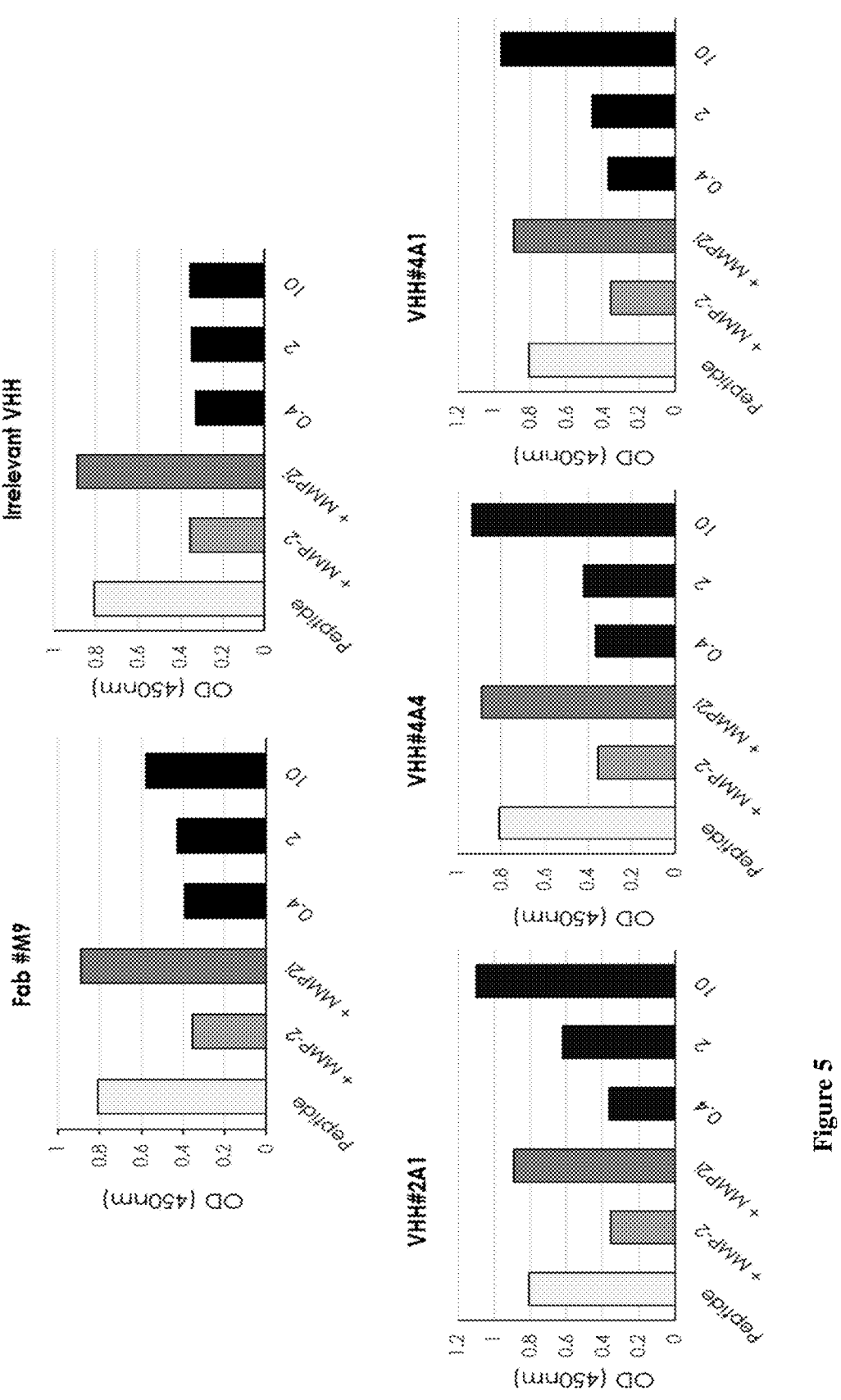

FIG. 5. In-vitro blocking of the MMP-2-mediated cleavage of human CD28 stalk region by VHH clones. A c-Myc conjugated and biotinylated human CD28 stalk region dimeric peptide (1 μM) was incubated with 50 ng rhMMP-2 in the presence of an MMP-2 inhibitor (TMI-1, 50 nM), M9 Fab or indicated VHH clones at various concentrations (0.4-10 μg/mL) for 5 hours. The mixtures were loaded on neutravidin coated ELISA maxi-sorb plates followed by extensive wash and detection of intact peptide by anti-cMyc HRP-conjugated antibody and development was carried out with TMB.

Figure 6:
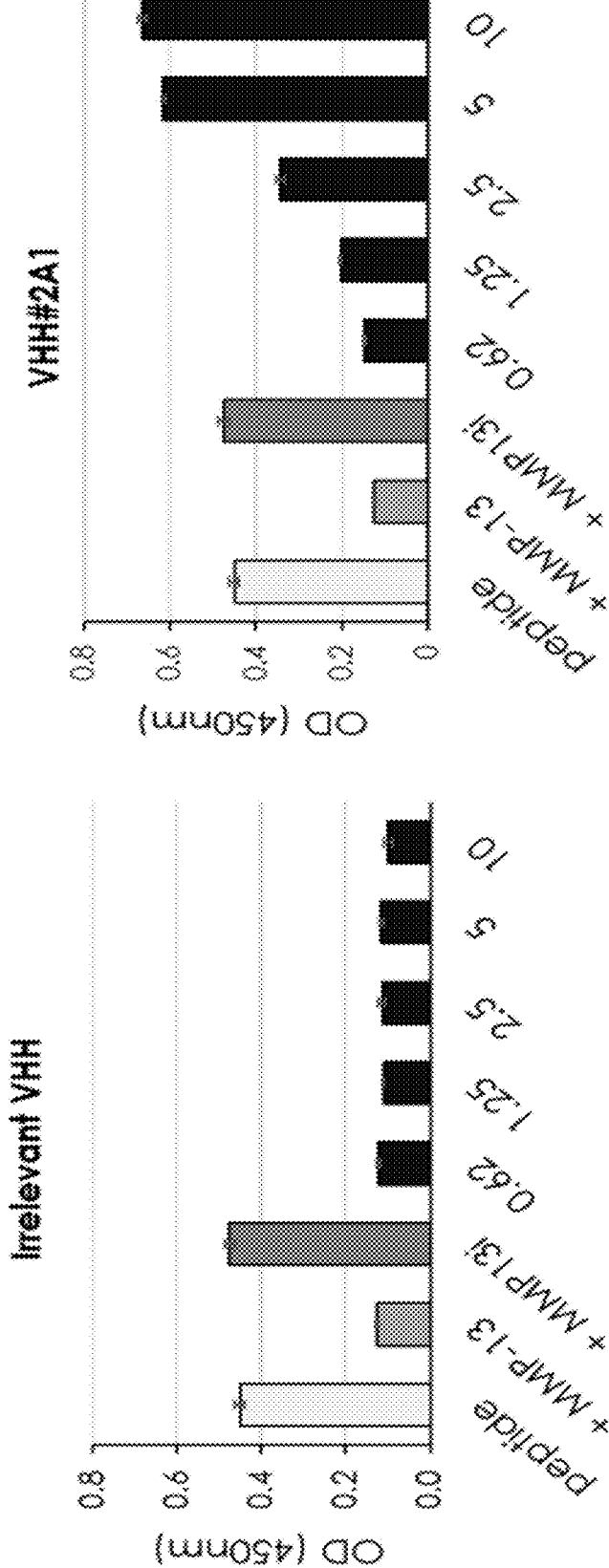

FIG. 6. In-vitro blocking activity of VHH clone 2A1 for the cleavage of human CD28 stalk region by MMP-13. A c-Myc and a biotinylated human CD28 stalk region dimeric peptide (1 μM) was incubated with 50 ng rhMMP-13 (light grey bar) in the presence of MMPi (TMI-1, 50 nM, dark grey bars), an irrelevant VHH clone (black bars in left chart), or VHH clone 2A1 (black bars in right chart) at various concentrations (0.62-10 μg/mL) for 5 hours. The mixtures were loaded on neutravidin coated ELISA maxi-sorb plates followed by extensive wash and detection of intact peptide by anti cMyc-HRP conjugated antibody and development was carried out with TMB.

Figure 7:
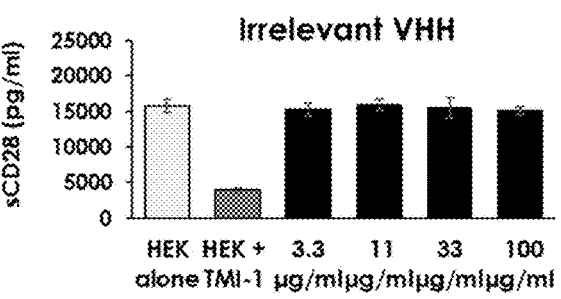
Figure 7:
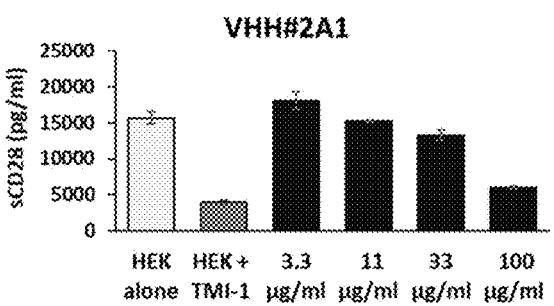
Figure 7:
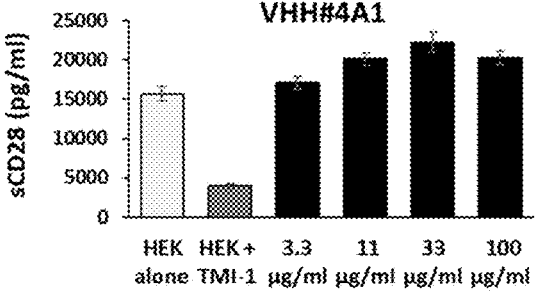
Figure 7:
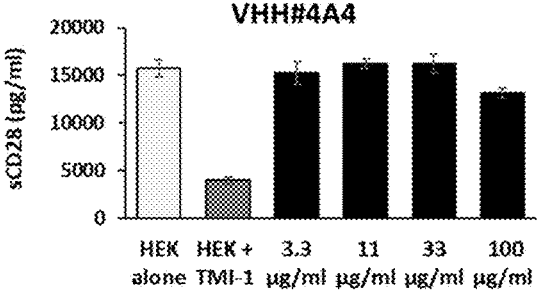

FIG. 7. Anti-CD28 stalk region VHH clones 2A1 and 4A4 inhibit CD28 shedding in HEK cells overexpressing human CD28. Levels of soluble CD28 were measured in culture media of HEK cells stably expressing human CD28 after 48 hr incubation. The effect of different treatments of MMP inhibitor (TMI-1, 1 dark grey bars), negative control of irrelevant VHH (top left chart, black bars) or anti-CD28 stalk region VHH clones (black bars) at various concentrations (3.3-100 µg/mL) on the level of soluble CD28 is depicted. The levels of soluble human CD28 in the supernatant were quantified with standardized sandwich ELISA (R&D system).

Figure 8:
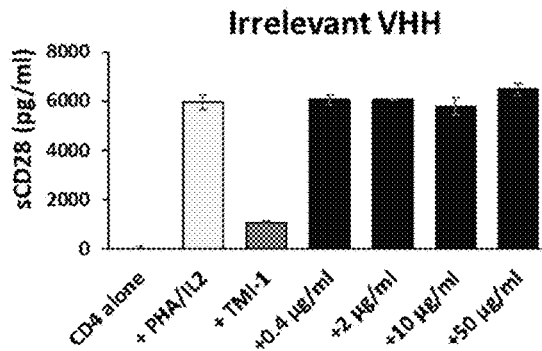
Figure 8:
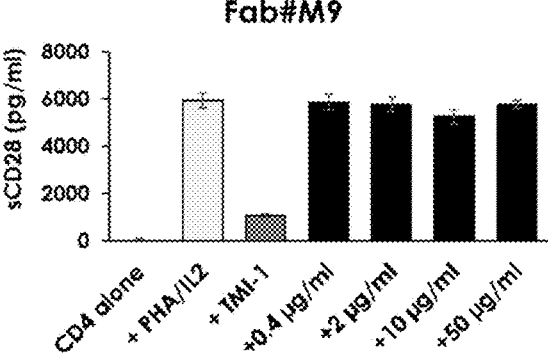
Figure 8:
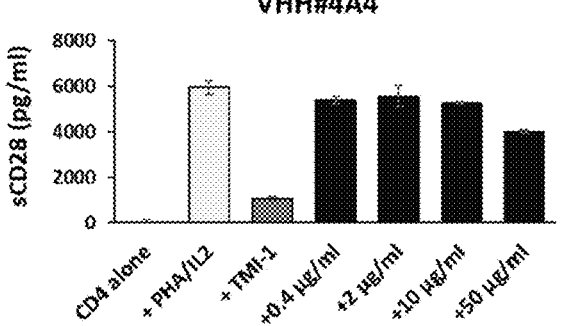
Figure 8:
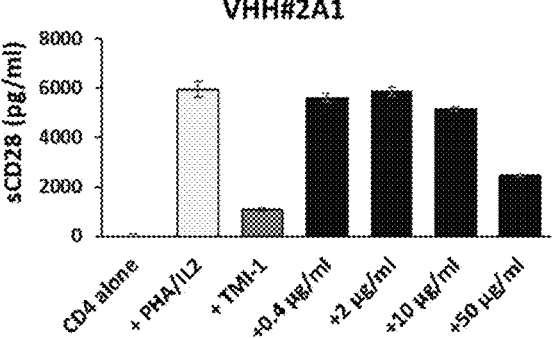

FIG. 8. Anti-CD28 stalk region VHH clones 2A1 and 4A4 inhibit CD28 shedding in isolated CD4 T cells activated by PHA and IL2. Levels of soluble CD28 were measured in culture media of isolated human CD4 T cells stimulated with 5 µg/mL PHA and 200 IU/mL IL-2 (light grey bar). The effect of different treatments of MMP inhibitor (TMI-1, 1 dark grey bars), negative control of irrelevant VHH (top left chart, black bars), anti-CD28 stalk region VHH clones or Fab format of antibody M9 clone (black bars) at various concentrations (0.4-50 µg/mL) on amount of soluble CD28 is depicted. The levels of soluble human CD28 in the supernatant were quantified with standardized sandwich ELISA (R&D system).

Figure 9:
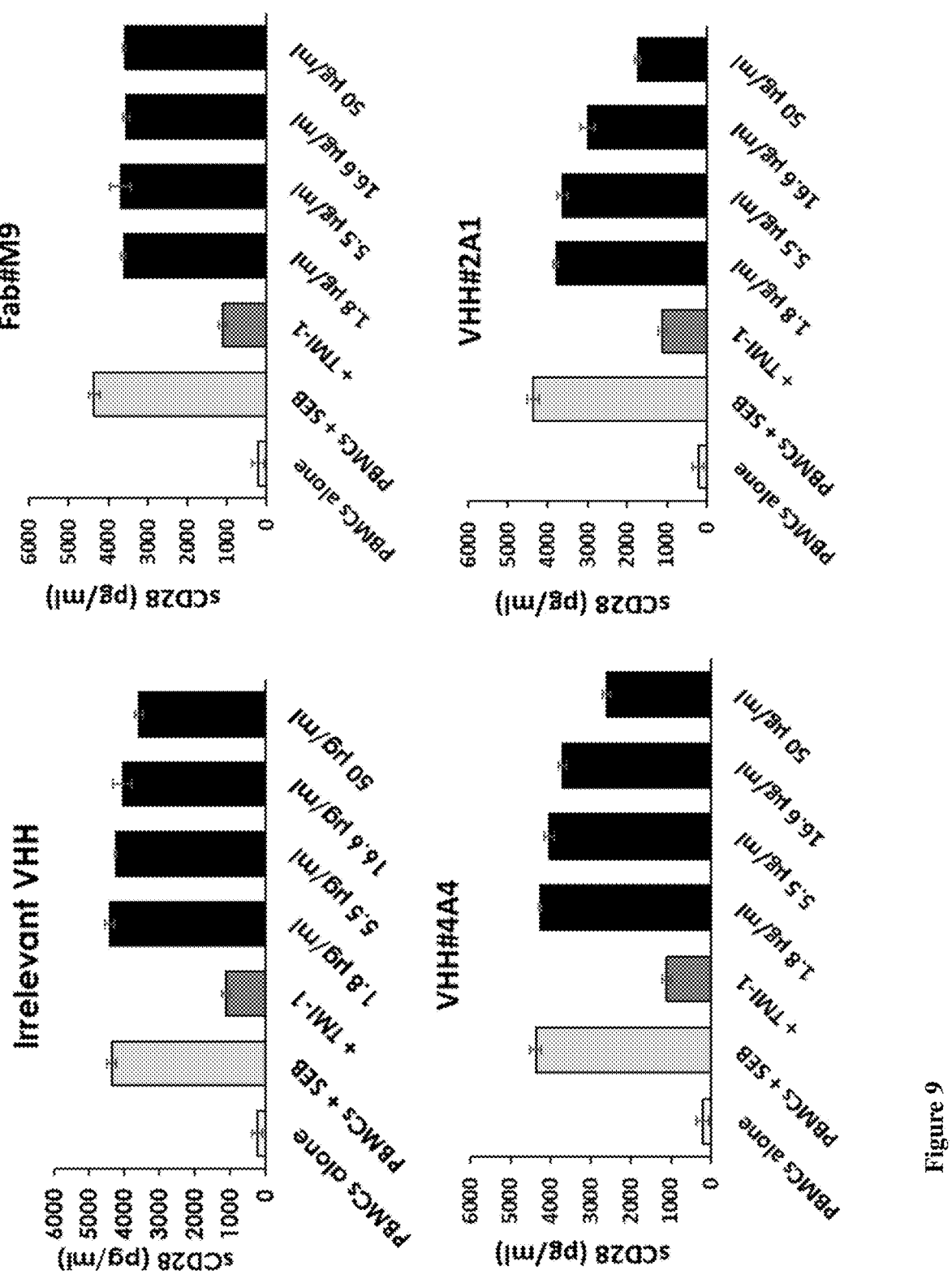

FIG. 9. Anti-CD28 stalk region VHH clones 2A1 and 4A4 inhibit CD28 shedding in PBMC activated by superantigen. Levels of soluble CD28 were measured in culture media of isolated PBMC stimulated with 1 ng/mL SEB (light grey bar). The effect of different treatments of MMP inhibitor (TMI-1, 1 dark grey bars), negative control of irrelevant VHH (top left chart, black bars), anti-CD28 stalk region VHH clones or Fab format of M9 clone (black bars) at various concentrations (0.4-50 µg/mL) on amount of soluble CD28 is depicted. The levels of soluble human CD28 in the supernatant were quantified with standardized sandwich ELISA (R&D system).

Figure 10:
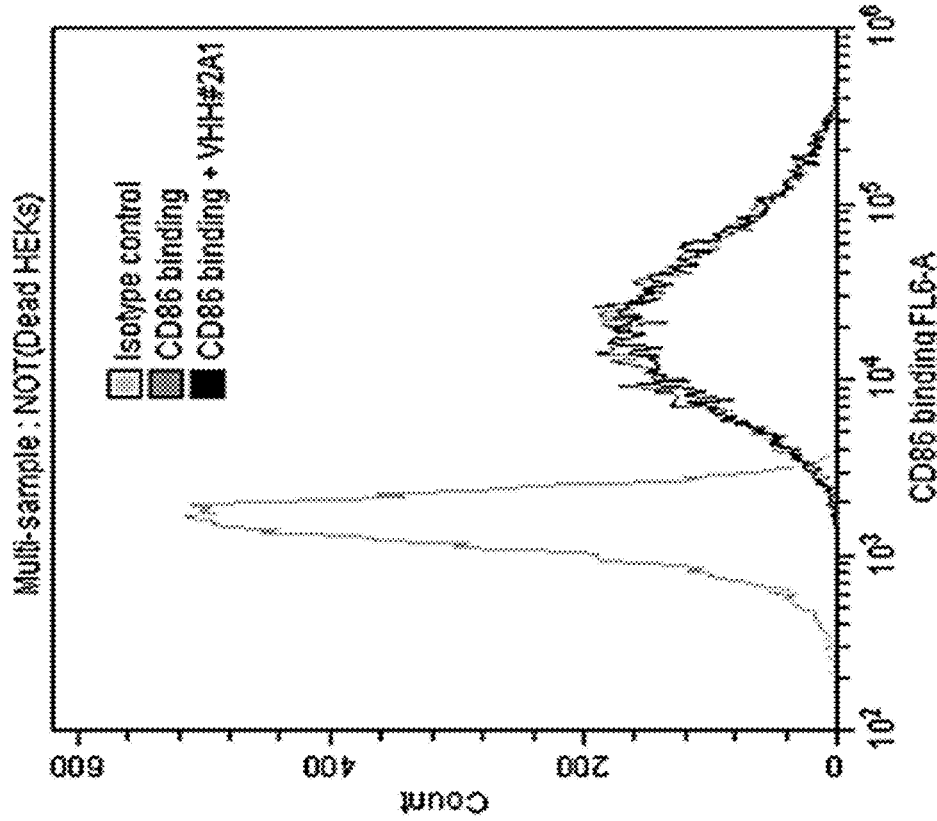
Figure 10:
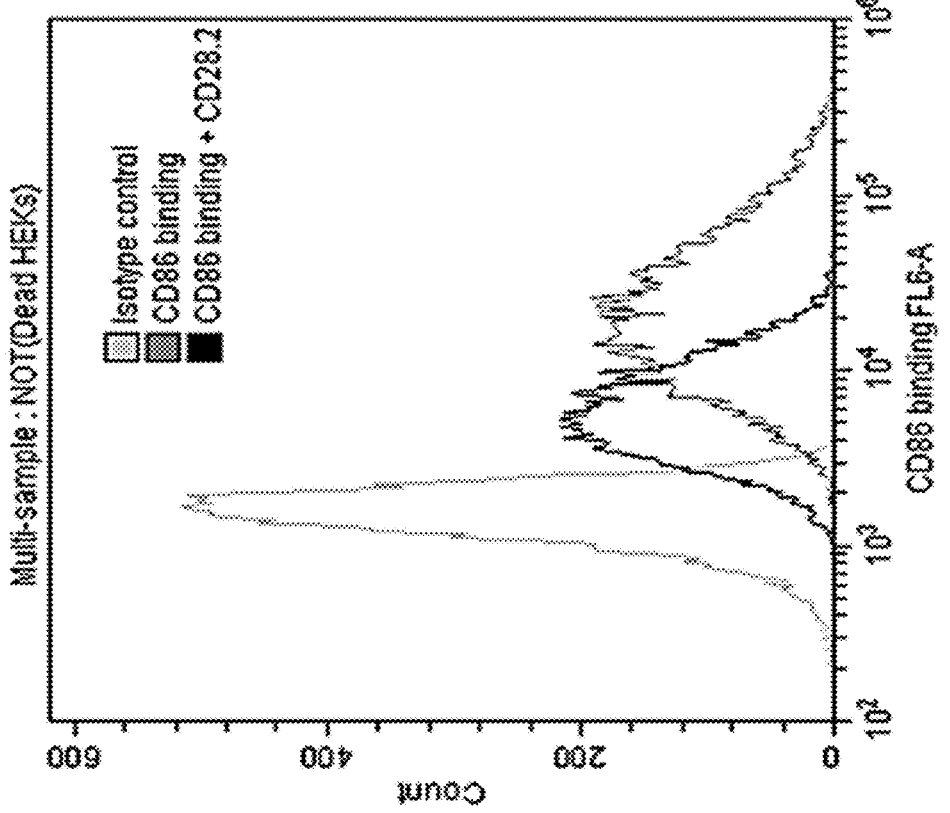

FIG. 10. Anti-CD28 stalk region VHH clones do not block ligand binding to membranal CD28. HEK293 cells over expressing human CD28 were monitored by flow-cytometry for CD86-Fc (2 µg/mL) binding using secondary anti human Fc antibody conjugated to Alexa Fluor 647. Addition of anti CD28 VHH clones to CD86-Fc (30 µg/mL, black histogram) did not change the magnitude of CD86 binding while addition of commercial antibody clone CD28.2 (10 µg/mL, upper left chart, black histogram) diminished binding significantly.

Figure 11:
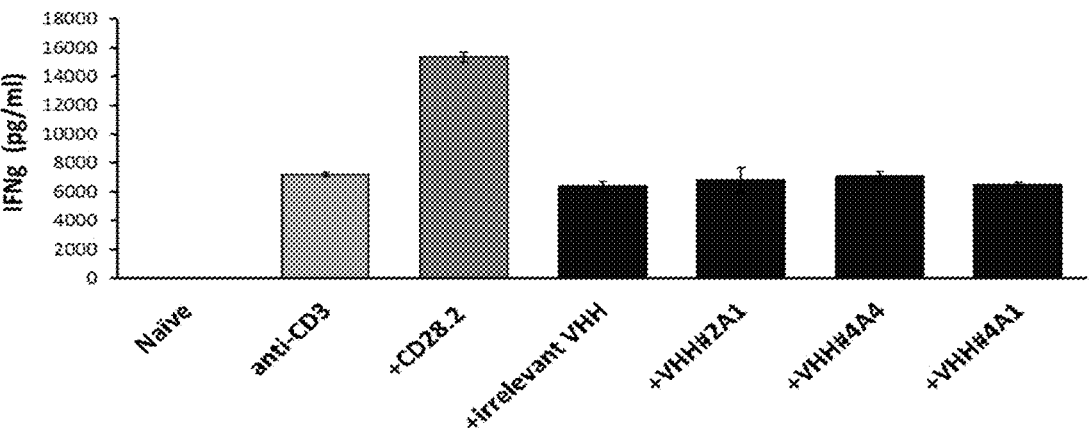

FIG. 11. Agonist effect evaluation of anti-CD28 stalk VHH clones. Human isolated CD3 cells were stimulated for 2 days with plate bound anti-CD3 (OKT3, 2 µg/mL, light grey bar) in the presence of anti-CD28 agonist antibody clone 28.2 (2 µg/mL, dark grey bar) serving as positive control, anti-CD28 stalk region VHHs or an irrelevant VHH clone (20 µg/mL, black bars). The concentration of human IFN gamma secreted into the supernatant was quantified with standardized sandwich ELISA (Biolegend).

Figure 12:
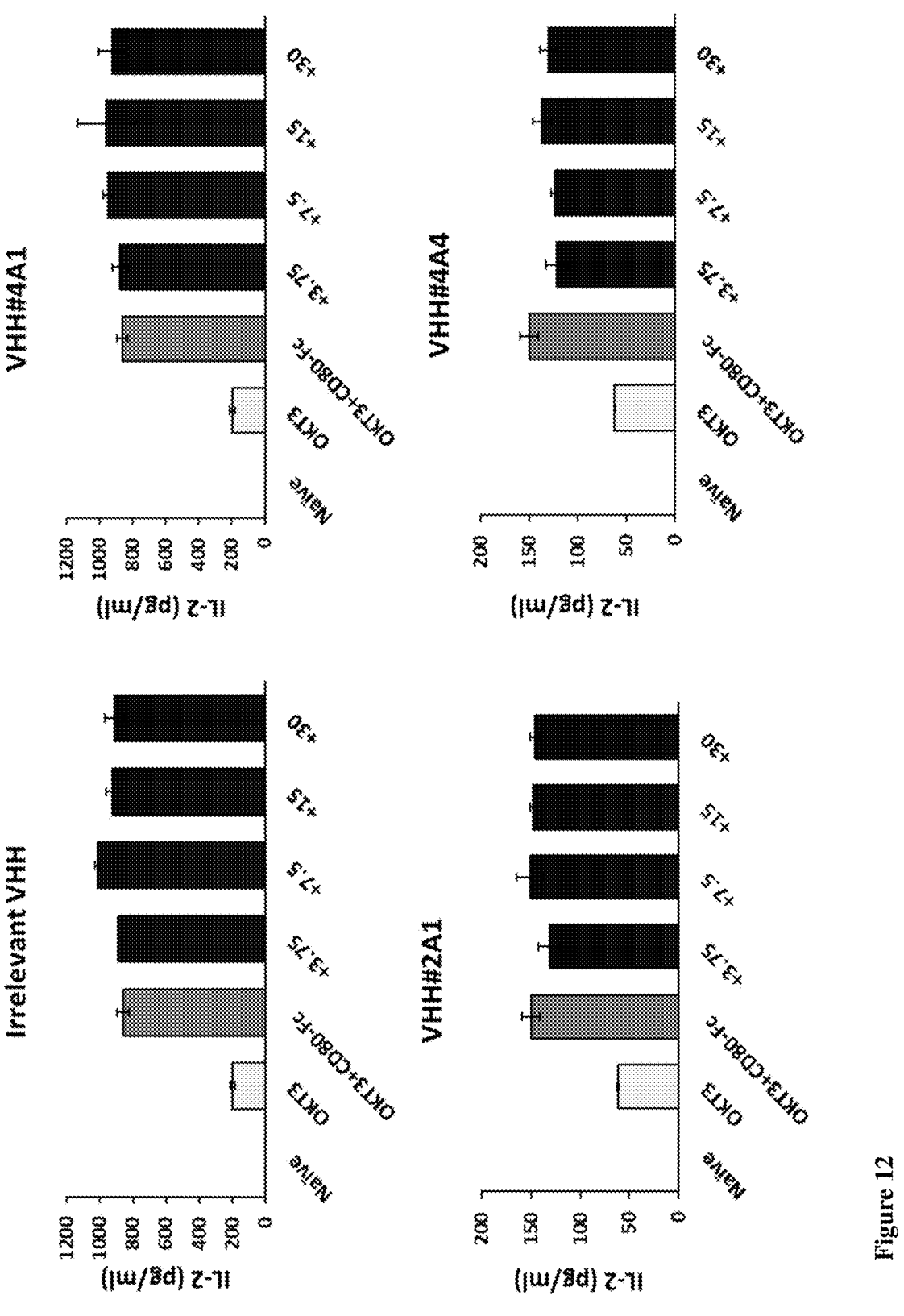

FIG. 12. Antagonist effect evaluation of anti-CD28 stalk VHH clones. Human isolated CD3 cells were stimulated for 24 hours with plate bound anti-CD3 (OKT3, 2 µg/mL, light grey bar) in the presence of recombinant CD80-Fc protein (5 µg/mL, dark grey bar) serving as ligand for CD28 co-stimulation. An irrelevant VHH clone (top left chart) or the anti-CD28 stalk region VHHs were added at various concentrations (3.75-30 µg/mL, black bars). The concentration of human IL-2 in the supernatant was quantified with standardized sandwich ELISA (Biolegend).

Figure 13:
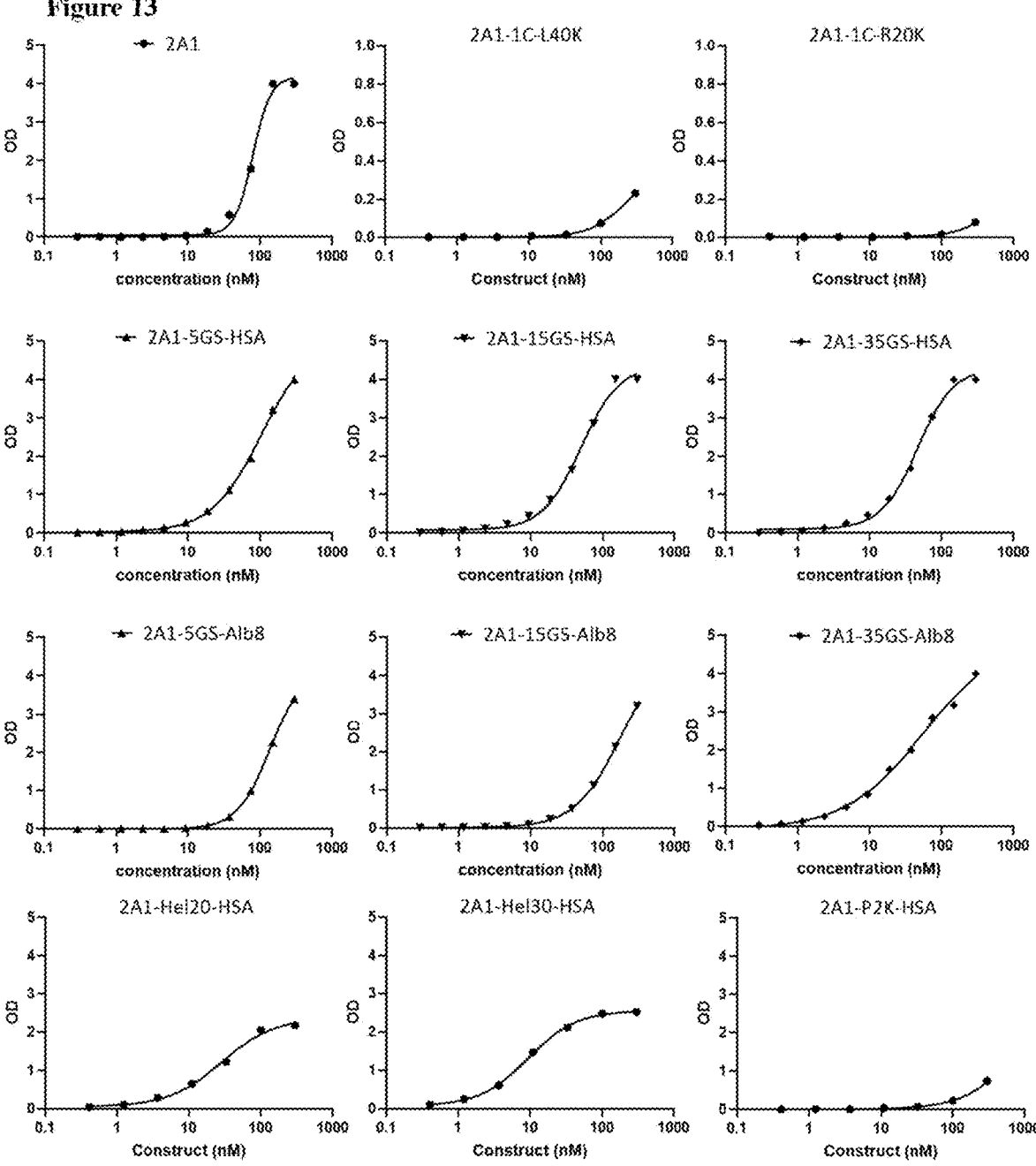

FIG. 13: Binding to Human CD28 stalk region sequence by different 2A1 half-life extending constructs. Analysis of antigen binding by serial dilution of parental 2A1 VHH and the 11 half-life extending constructs. CD28-Fc recombinant peptide was used as bait.

Figure 14:
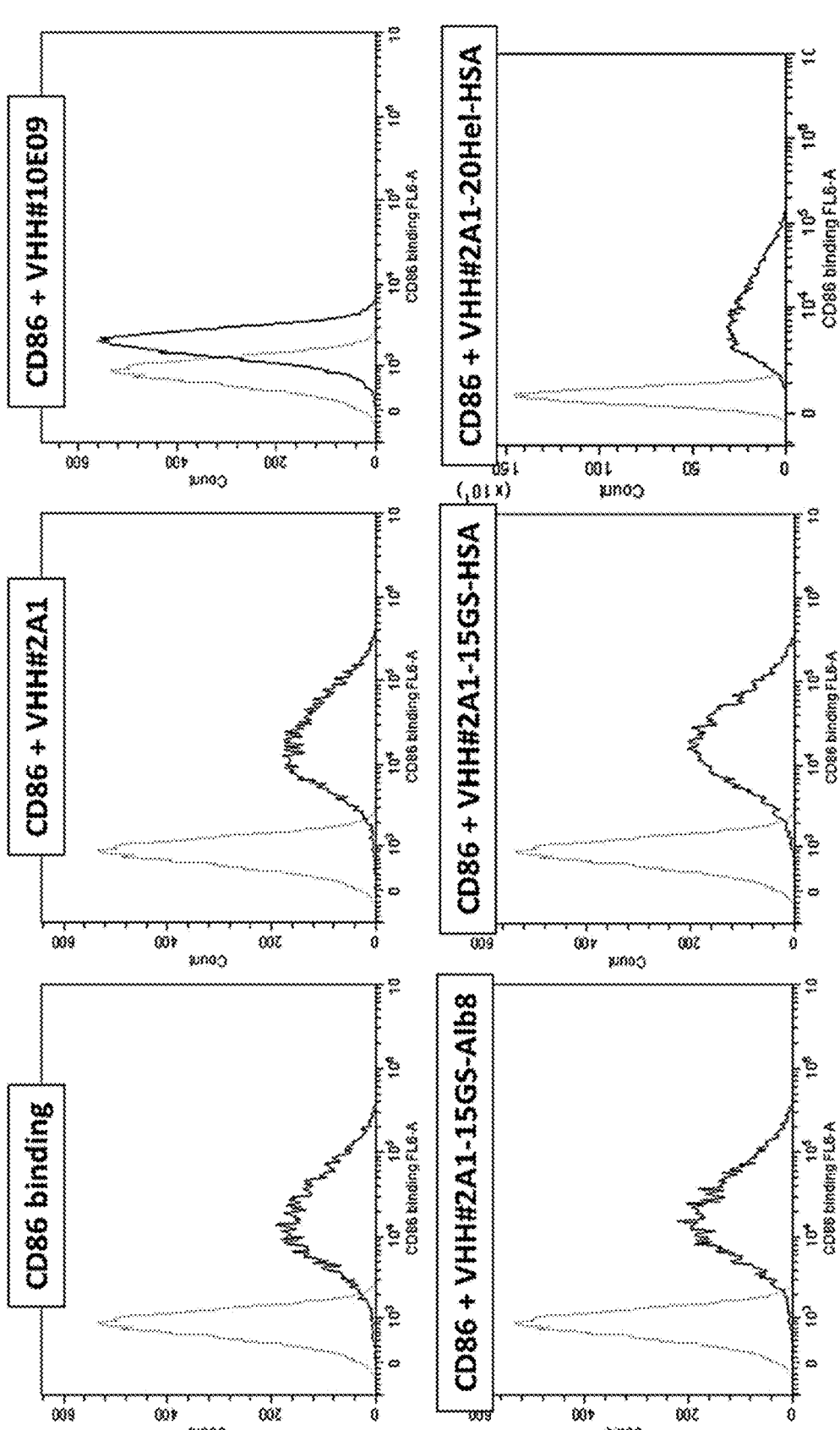
Figure 14:
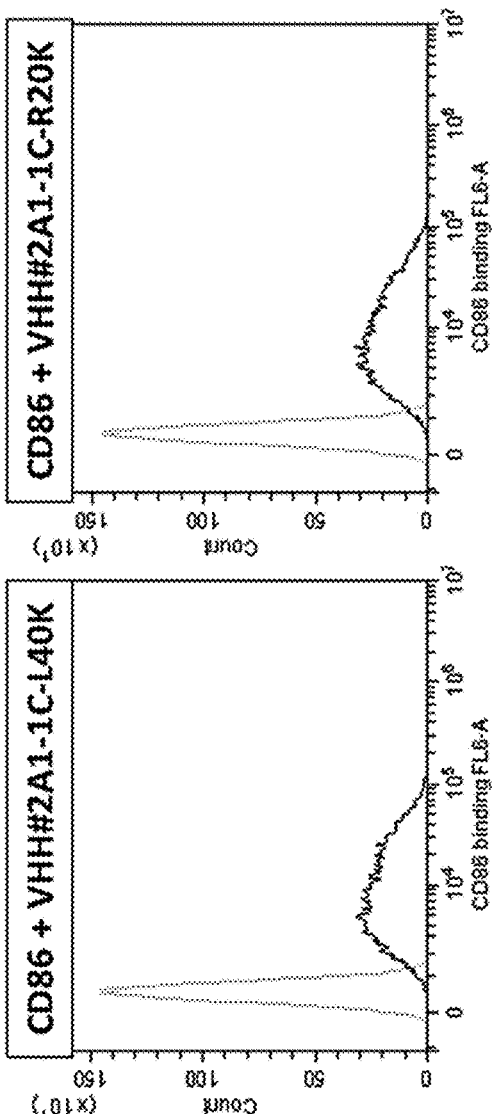

FIG. 14: Ligand blocking activity by different 2A1 half-life extending constructs to membrane CD28. Histograms showing CD86 binding to HEK293 cells expressing human CD28 (Top row/left), in the presence of parental 2A1 VHH (Top row/middle), positive control antagonistic antibody (Top row/right) as well as the various half-life extending constructs. Constructs with the 15 amino acid long flexible linkers are shown, though similar results were observed with the 5 amino acid and 35 amino acid flexible linkers. The 20 amino acid long rigid linker is shown, though similar results were observed with the 30 amino acid rigid linker.

Figures 15A, 15B:
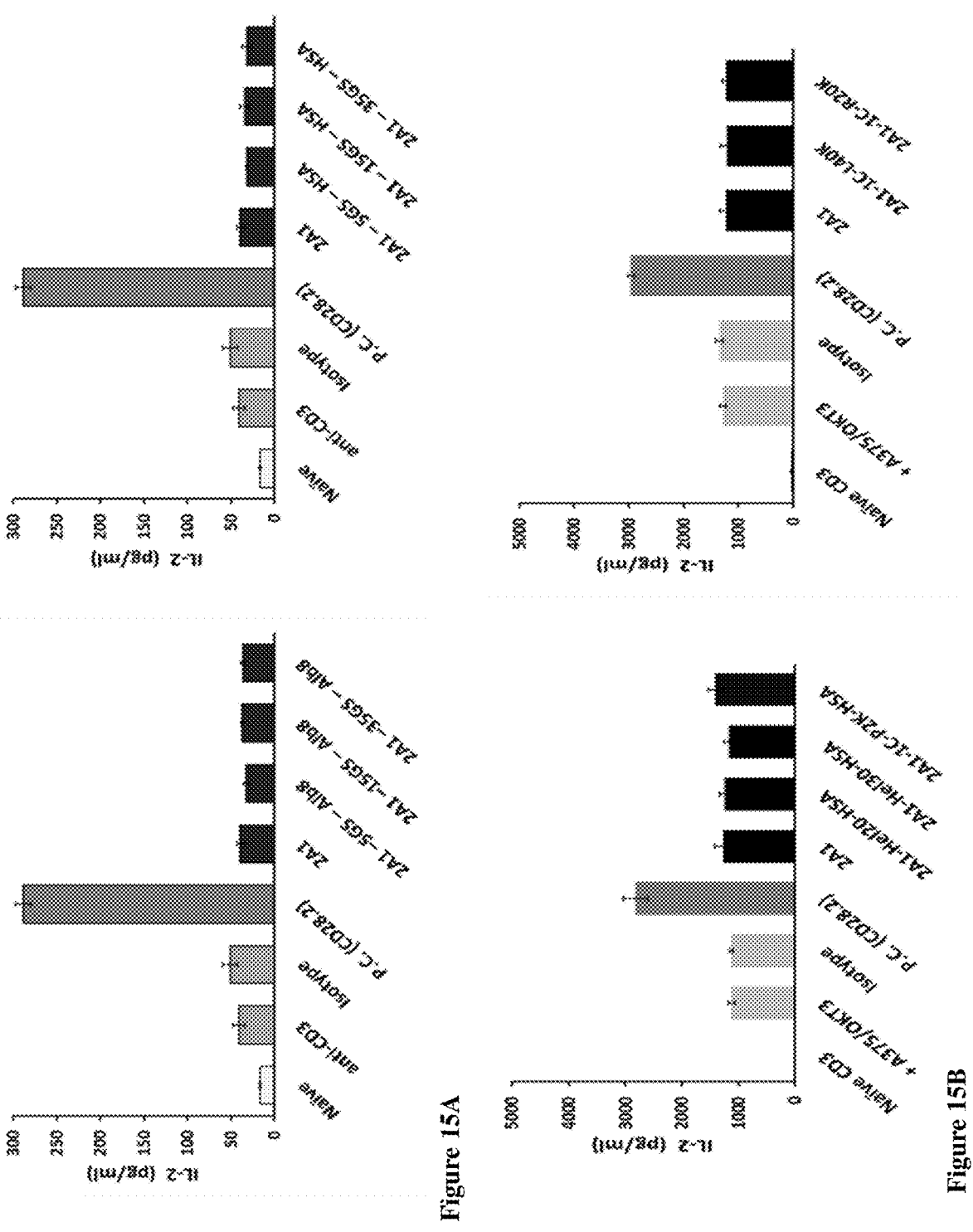

FIGS. 15A-15B: Agonist effect evaluation of different 2A1 half-life extending constructs. Bar charts of IL2 secretion from isolated human CD3 T cells that were stimulated for 24 hours with (15A) plate bound anti-CD3 (OKT3, 2 µg/mL, light grey bar) or (15B) A375 cells transfected with scOKT3 plasmid (artificial APC, grey bar), in the presence of an irrelevant VHH clone #3C04 (1.2 dark grey bars), a positive control anti-CD28 agonist antibody clone 28.2 (2 µg/mL, dark grey bars), or different 2A1 constructs (1.2 black bars).

Figure 16:
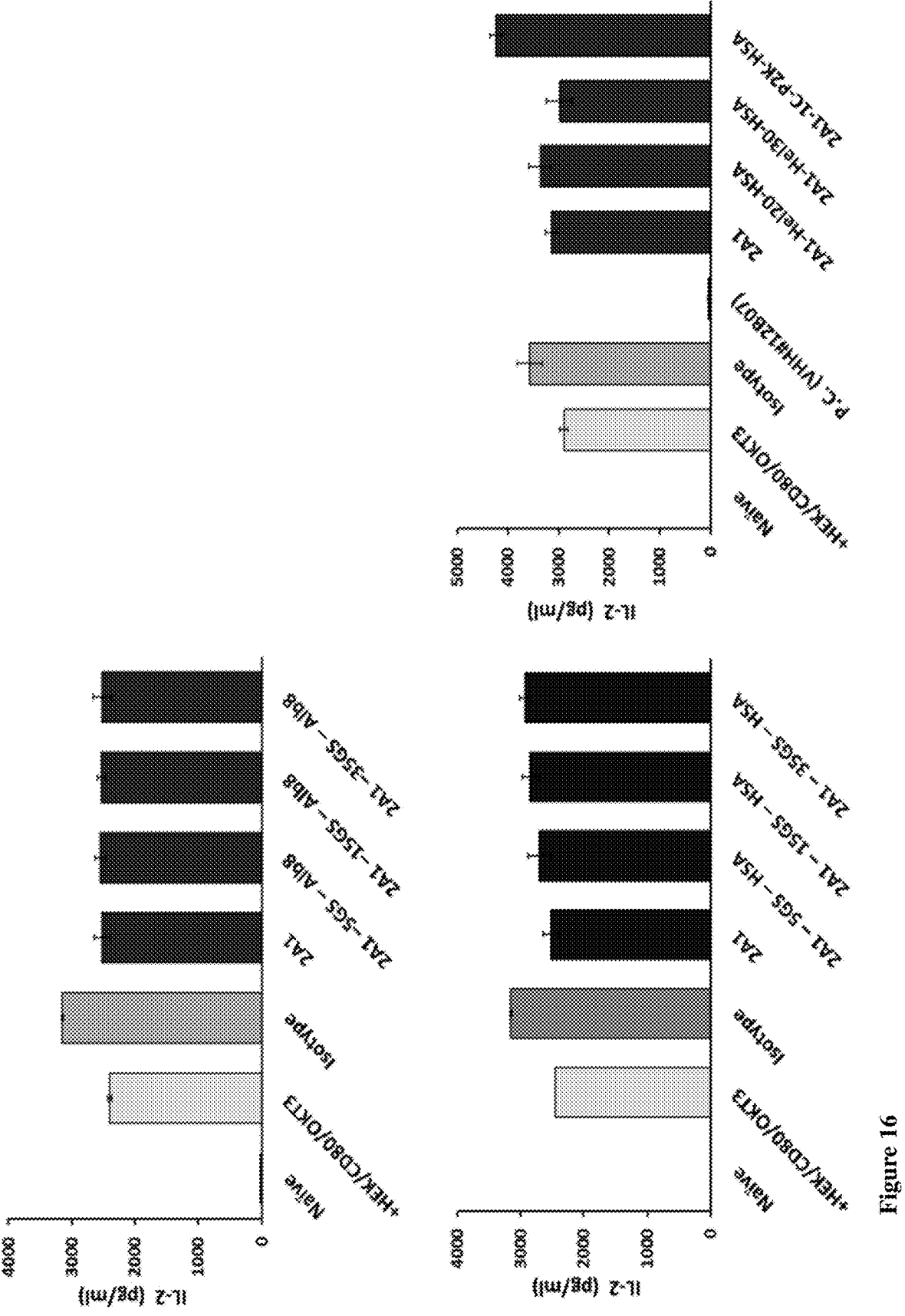
Figure 16:
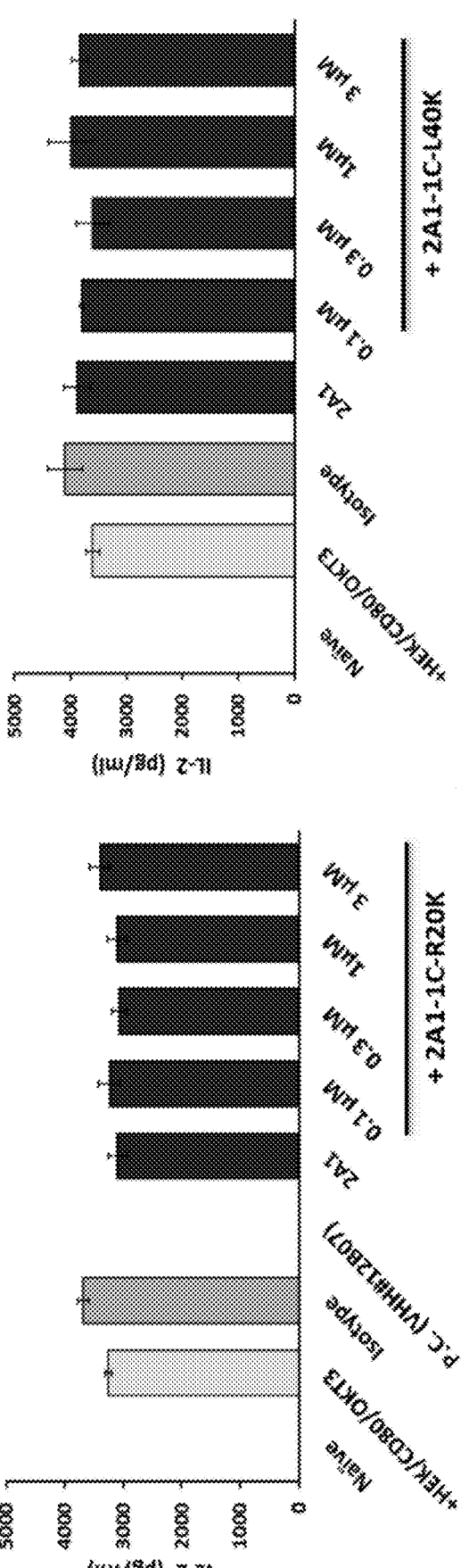

FIG. 16: Antagonist effect evaluation of different 2A1 half-life extending constructs. Bar charts of IL2 secretion from isolated human CD3 T cells that were stimulated for 24 hours with both human CD80 and scOKT3 plasmids (artificial APC-CD80, light grey bars) in the presence of an irrelevant VHH clone #3C04 (2 Isotype control, dark grey bars), positive control anti-CD28 antagonist clone VHH #12B07 (1 µM) or the various 2A1 constructs. Constructs with flexible and rigid linkers were used as 2 µM. PEGylated constructs were used at various concentrations (0.1-3 µM).

Figure 17:
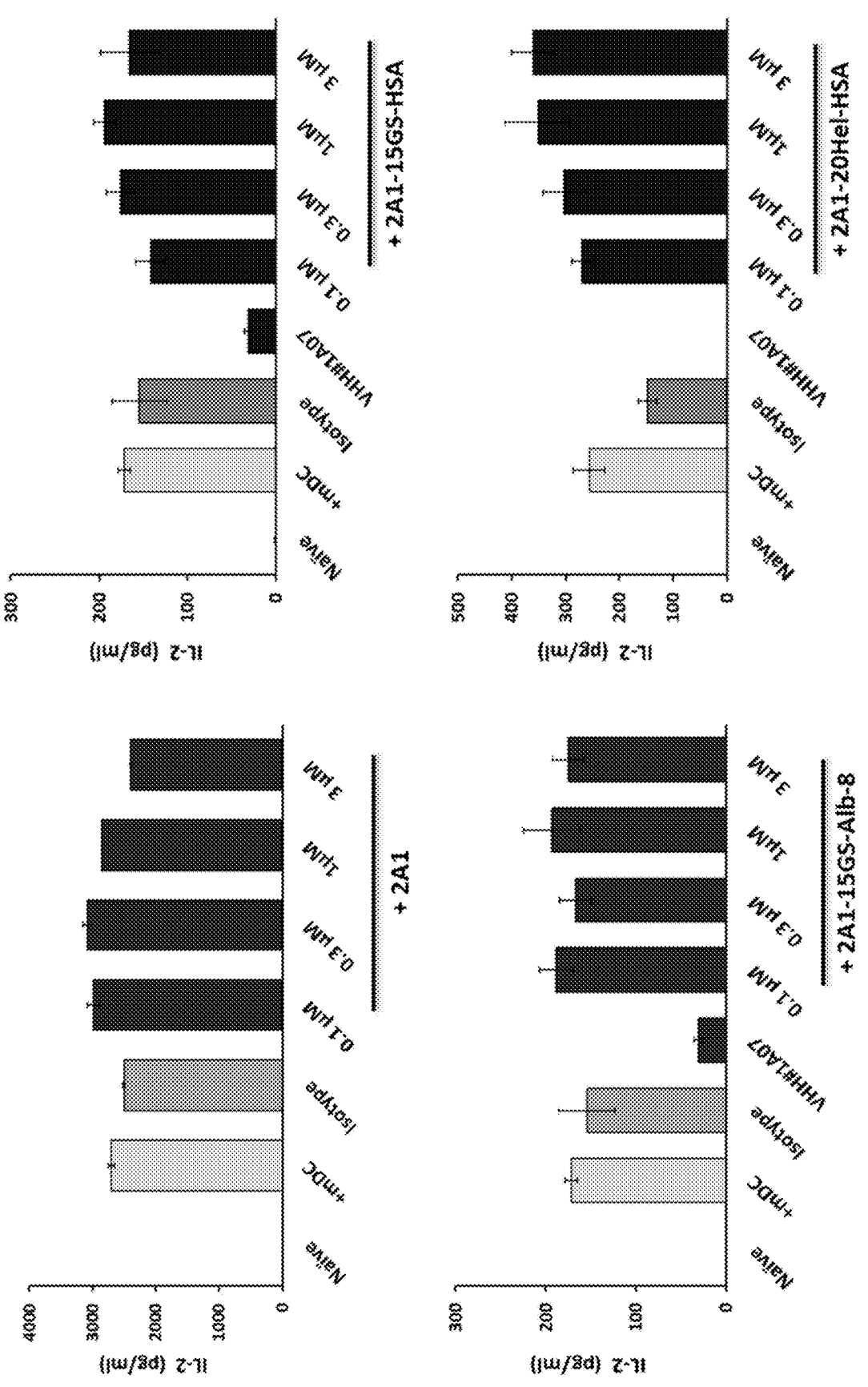
Figure 17:
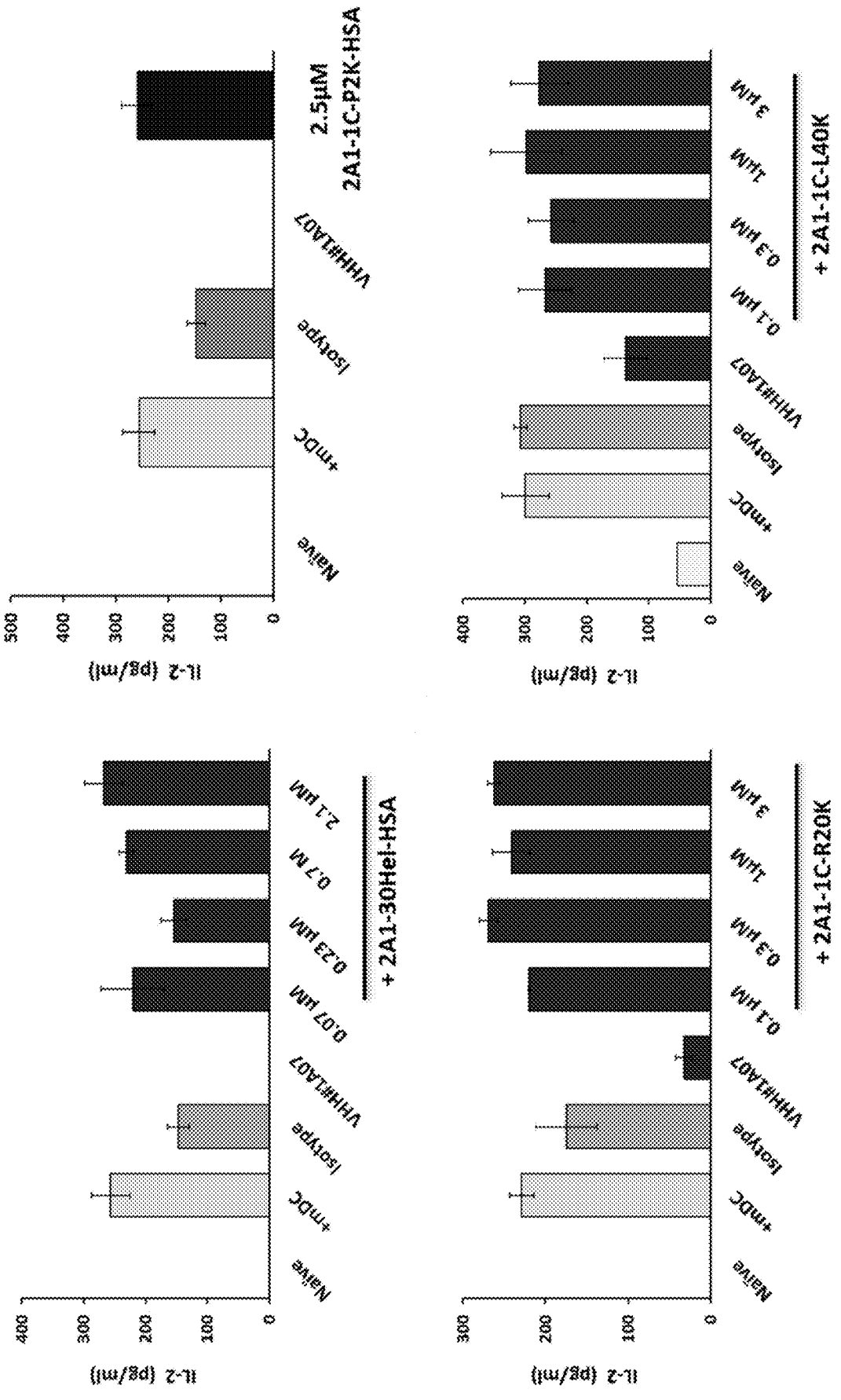

FIG. 17: Immune-modulatory effect of different 2A1 half-life extending constructs in MLR based assay. Bar charts of IL2 secretion from a mixed-lymphocyte reaction (light grey bars), in the presence of an irrelevant VHH clone #3C04 (3 µM, Isotype control, dark grey bars), CD28 antagonist clone VHH #1A07 (3 µM), and different 2A1 constructs at various concentrations (0.1-3 µM, except 2A1-1C-P2K-HSA which was used at sole concentration of 2.5 µM).

Figure 18:
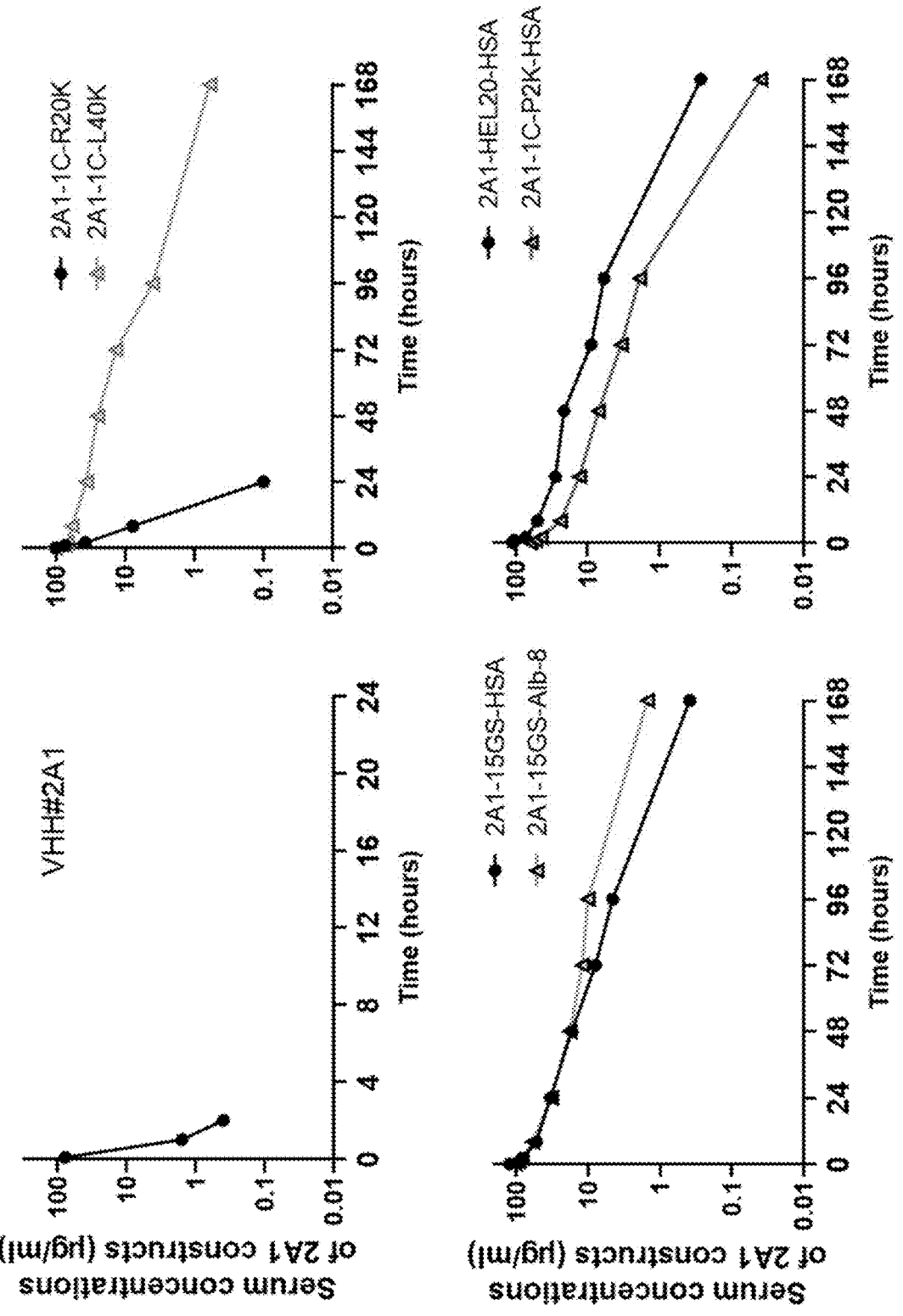

FIG. 18: The impact of half-life extended construct on 2A1 serum exposure in mice. Line graphs of mean observed (n=3*; ±standard deviation) serum concentrations (µg/mL) as function of time (hours) of the various tested VHH constructs in mice.

Figure 19:
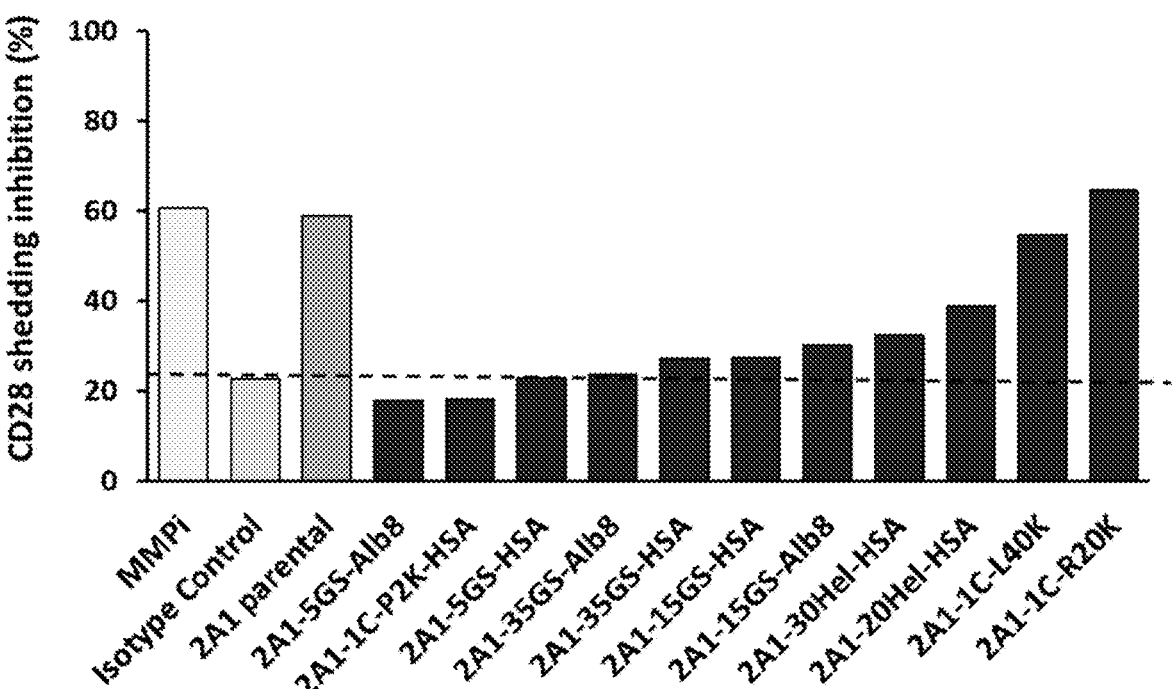

FIG. 19: Inhibition of CD28 shedding in stimulated lymphocytes. Levels of soluble CD28 were measured in culture media of isolated human CD4 stimulated with PHA and IL-2 or PBMCs stimulated with SEB and normalized to negative control with an irrelevant VHH #3C04 negative control (3 µM, Isotype control, grey bar). Parental 2A1 VHH (3 µM, dark grey bar), MMP inhibitors (positive control, 1 µM TMI-1, light grey bar) and the various 2A1 half-life extending constructs (3 µM, black bars) were also assessed and normalized.

DETAILED DESCRIPTION OF THE INVENTION

The present invention, in some embodiments, provides agents comprising at least two moieties, wherein a first moiety binds membranal CD28 (mCD28) on a cell surface and inhibits proteolytic cleavage of the mCD28, and a second moiety increases stability of the first moiety. Methods of generating agents of the invention, treating cancer, improving PD-1/PD-L1 based immunotherapy, and decreasing sCD28 levels in a subject comprising administering an agent of the invention are also provided. Pharmaceutical compositions comprising the agents of the invention, as well as methods of use of the pharmaceutical compositions are also provided. The agents, methods and compositions of the invention are based on the surprising finding that sCD28, as results from proteolytic cleavage of mCD28, acts as an immunosuppressant, and so reduction of shedding has the double benefit of decreasing the inhibition by sCD28 and increasing immune activation via mCD28 signaling. Full size antibodies against the cleavage site of mCD28 are too large to access the membrane proximal region and thus cannot inhibit shedding, while a smaller polypeptide with specificity to mCD28 on a cell surface is able to access the membrane proximal region and block proteolytic cleavage. Therapeutically useful stability of the polypeptide in serum is enhanced by linkage to a second moiety. The second moiety increases the serum half-life of the first moiety, while not affecting the binding capability of the polypeptide to mCD28 on cells.

Agents

According to a first aspect, there is provided an agent comprising at least two moieties separated by a linker, wherein a first moiety binds mCD28 on a surface of a cell and wherein a second moiety increases stability of the first moiety.

The term "moiety", as used herein, relates to a part of a molecule that may include either whole functional groups or parts of functional groups as substructures. The term "moiety" further means part of a molecule that exhibits a particular set of chemical and/or pharmacologic characteristics which are similar to the corresponding molecule.

In some embodiments, the CD28 is mammalian CD28. In some embodiments the CD28 is human CD28. In some embodiments, the human CD28 comprises or consists of the amino acid sequence:

```
                                    (SEQ ID NO: 20)
MLRLLLLALNLFPSIQVTGNKILVKQSPMLVAYDNAVNLSCKYSYNLFSRE

FRASLHKGLDSAVEVCVVYGNYSQQLQVYSKTGFNCDGKLGNESVTFYLQ

NLYVNQTDIYFCKIEVMYPPPYLDNEKSNGTIIHVKGKHLCPSPLFPGPS

KPFWVLVVVGGVLACYSLLVTVAFIIFWVRSKRSRLLHSDYMNMTPRRPG

PTRKHYQPYAPPRDFAAYRS
```

In some embodiments, mature CD28 lacks a signal peptide and comprises the sequence:

```
                                    (SEQ ID NO: 21)
NKILVKQSPMLVAYDNAVNLSCKYSYNLFSREFRASLHKGLDSAVEVCVV

YGNYSQQLQVYSKTGFNCDGKLGNESVTFYLQNLYVNQTDIYFCKIEVMY

PPPYLDNEKSNGTIIHVKGKHLCPSPLFPGPSKPFWVLVVVGGVLACYSL

LVTVAFIIFWVRSKRSRLLHSDYMNMTPRRPGPTRKHYQPYAPPRDFAAY

RS.
```

In some embodiments, the DNA coding sequence that codes for full length human CD28 comprises the sequence:

```
                                    (SEQ ID NO: 22)
ATGCTCAGGCTGCTCTTGGCTCTCAACTTATTCCCTTCAATTCAAGTAAC

AGGAAACAAGATTTTGGTGAAGCAGTCGCCCATGCTTGTAGCGTACGACA

ATGCGGTCAACCTTAGCTGCAAGTATTCCTACAATCTCTTCTCAAGGGAG

TTCCGGGCATCCCTTCACAAAGGACTGGATAGTGCTGTGGAAGTCTGTGT

TGTATATGGGAATTACTCCCAGCAGCTTCAGGTTTACTCAAAAACGGGGT

TCAACTGTGATGGGAAATTGGGCAATGAATCAGTGACATTCTACCTCCAG

AATTTGTATGTTAACCAAACAGATATTTACTTCTGCAAAATTGAAGTTAT

GTATCCTCCTCCTTACCTAGACAATGAGAAGAGCAATGGAACCATTATCC

ATGTGAAAGGGAAACACCTTTGTCCAAGTCCCCTATTTCCCGGACCTTCT

AAGCCCTTTTGGGTGCTGGTGGTGGTTGGTGGAGTCCTGGCTTGCTATAG

CTTGCTAGTAACAGTGGCCTTTATTATTTTCTGGGTGAGGAGTAAGAGGA

GCAGGCTCCTGCACAGTGACTACATGAACATGACTCCCCGCCGCCCCGGG

CCCACCCGCAAGCATTACCAGCCCTATGCCCCACCACGCGACTTCGCAGC

CTATCGCTCCTGA.
```

In some embodiments, the CD28 is membranal CD28 (mCD28). In some embodiments, membranal CD28 is membrane CD28. In some embodiments, the mCD28 is on a cell surface. In some embodiments, the mCD28 is in a membrane. In some embodiments, the cell surface is a cell membrane. In some embodiments, the cell is a mammalian cell. In some embodiments, the cell is an immune cell. In some embodiments, the immune cell is a T cell. In some embodiments, the immune cell is an NK cell. In some embodiments, the immune cell is an NKT cell. In some embodiments, the cell is a cell of a cell line. In some embodiments, the cell line expresses mCD28. In some embodiments, the cell line expresses mCD28 from an expression vector. In some embodiments, the cell line stably expresses mCD28.

In some embodiments, the CD28 is soluble CD28 (sCD28). As used herein, sCD28 refers to any CD28 fragment or variant that does not comprise a transmembrane domain and thus cannot be integrated in a membrane. In some embodiments, the CD28 transmembrane domain comprises the amino acid sequence FWVLVVVGGVLACYS-LLVTVAFIIFWV (SEQ ID NO: 23). In some embodiments, sCD28 is not membrane bound. In some embodiments, sCD28 is in solution. In some embodiments, the sCD28 is CD28 in blood. In some embodiments, the sCD28 is CD28 in the TME. In some embodiments, sCD28 is CD28 in a bodily fluid. In some embodiments, sCD28 lacks exon 3 of CD28. In some embodiments, sCD28 is a splice variant arising from alternative splicing that splices out exon 3 of CD28. In some embodiments, sCD28 is a cleavage product from membranal CD28 (mCD28). In some embodiments, sCD28 is truncated CD28. In some embodiments, sCD28 lacks the cytoplasmic domain of full-length CD28. In some embodiments, sCD28 is dimeric sCD28. In some embodiments, sCD28 is monomeric sCD28. In some embodiments, sCD28 is not a splice variant arising from alternative splicing of CD28. In some embodiments, the alternative splicing splices out exon 3 of CD28. In some embodiments, sCD28 comprises the amino acid sequence: MLRLLLALNLFP-SIQVTGNKILVKQSPMLVAYDNAVNLSCKYSYNLFS- REFRASLHKG LDSAVEVCVVYGNYSQQLQVYSK-
TGFNCDGKLGNESVTFYLQNLYVNQTDIYFCKIE
VMYPPPYLDNEKSNGTIIHVKGEE (SEQ ID NO: 24). In
some embodiments, sCD28 consists of the amino acid
sequence of SEQ ID NO: 24. In some embodiments, sCD28
lacks the signal peptide and comprises the sequence: NKIL-
VKQSPMLVAYDNAVNLSCKYSYNLFSREFRASLH-
KGLDSAVEVCVVYGNYSQQ LQVYSKTGFNC-
DGKLGNESVTFYLQNLYVNQTDIYFCKIEVMYPP-
PYLDNEKSNGTIIH VKGEE (SEQ ID NO: 25). In some
embodiments, sCD28 consists of the amino acid sequence of
SEQ ID NO: 25. In some embodiments, sCD28 comprises
the amino acid sequence: MLRLLLALNLFP-
SIQVTGNKILVKQSPMLVAYDNAVNLSCKYSYNLFS-
REFRASLHKG LDSAVEVCVVYGNYSQQLQVYSKT-
GFNCDGKLGNESVTFYLQNLYVNQTDIYFCKIE
VMYPPPYLDNEKSNGTIIHVKGKHLCPSP (SEQ ID
NO: 26). In some embodiments, sCD28 consists of the
amino acid sequence of SEQ ID NO: 26. In some embodi-
ments, sCD28 lacks the signal peptide and comprises the
sequence: NKILVKQSPMLVAYDNAVNLSCKYSYNLFS-
REFRASLHKGLDSAVEVCVVYGNYSQQ LQVY-
SKTGFNCDGKLGNESVTFYLQNLYVNQTDIYFCKI-
EVMYPPPYLDNEKSNGTIIH VKGKHLCPSP (SEQ ID
NO: 27). In some embodiments, sCD28 consists of the
amino acid sequence of SEQ ID NO: 27.

In some embodiments, the DNA coding sequence that
codes for human sCD28 comprises the sequence:

```
                                      (SEQ ID NO: 28)
ATGCTCAGGCTGCTCTTGGCTCTCAACTTATTCCCTTCAATTCAAGTAAC

AGGAAACAAGATTTTGGTGAAGCAGTCGCCCATGCTTGTAGCGTACGACA

ATGCGGTCAACCTTAGCTGCAAGTATTCCTACAATCTCTTCTCAAGGGAG

TTCCGGGCATCCCTTCACAAAGGACTGGATAGTGCTGTGGAAGTCTGTGT

TGTATATGGGAATTACTCCCAGCAGCTTCAGGTTTACTCAAAAACGGGGT

TCAACTGTGATGGGAAATTGGGCAATGAATCAGTGACATTCTACCTCCAG

AATTTGTATGTTAACCAAACAGATATTTACTTCTGCAAAATTGAAGTTAT

GTATCCTCCTCCTTACCTAGACAATGAGAAGAGCAATGGAACCATTATCC

ATGTGAAAGGTGAGGAGTAAGAGGAGCAGGCTCCTGCACAGTGACTACAT

GAACATGACTCCCCGCCGCCCCGGGCCCACCCGCAAGCATTACCAGCCCT

ATGCCCCACCACGCGACTTCGCAGCCTATCGCTCCTGA.
```

The effects of sCD28 on immune cells are well known in
the art, and include as non-limiting examples, immune cell
induction of anti-inflammatory cytokines such as IL-10 or
TGF β, immune cell expression of Indoleamine 2,3-dioxy-
genase (IDO), and immune cell down regulation of pro-
inflammatory cytokines, such as IL-2 or IFN-γ. In some
embodiments, the agent inhibiting proteolytic cleavage of
membranal CD28 comprises inhibiting generation of
sCD28. In some embodiments, the inhibiting generation of
sCD28 comprises inhibiting effects of sCD28 on immune
cells.

In some embodiments, the agent comprises at least two
moieties. In some embodiments, the agent comprises a
plurality of moieties. In some embodiments, the agent
comprises at least 2, 3, 4, 5, 6, or 7 moieties. Each possibility
represents a separate embodiment of the invention. In some embodiments, the agent comprises two moieties. In some
embodiments, the agent comprises a first moiety and a
second moiety. In some embodiments, at least one of the
moieties is a binding moiety. In some embodiments, at least
one of the moieties is a half-life enhancing moiety. In some
embodiments, at least one of the moieties is a half-life
extending moiety. In some embodiments, at least one of the
moieties is a stability enhancing moiety. In some embodi-
ments, at least one of the moieties is a stability increasing
moiety.

In some embodiments, the first moiety, the second moiety
or both is not a full-size antibody. In some embodiments, the
first moiety, the second moiety or both is not an IgG. In some
embodiments, the agent, the first moiety, the second moiety
or a combination thereof is smaller than 100 kilodaltons
(kDa). In some embodiments, the agent, the first moiety, the
second moiety or a combination thereof is smaller than 100,
95, 90, 85, 80, 75, 70, 65, 60, 55, 50, 45, 40, 35, 30, 25, 20
or 15 kDa. Each possibility represents a separate embodi-
ment of the invention. In some embodiments, the agent, the
first moiety, the second moiety or a combination thereof is
smaller than 50 kDa. In some embodiments, the agent, the
first moiety, the second moiety or a combination thereof is
smaller than 25 kDa. In some embodiments, the agent, the
first moiety, the second moiety or a combination thereof is
smaller than 20 kDa. In some embodiments, the agent, the
first moiety, the second moiety or a combination thereof is
smaller than 15 kDa.

In some embodiments, a first moiety binds mCD28. In
some embodiments, a first moiety binds mCD28 on a surface
of a cell. In some embodiments, a first moiety inhibits
proteolytic cleavage of the mCD28. In some embodiments,
the mCD28 is the mCD28 bound by the first moiety. As used
herein, "inhibiting proteolytic cleavage" refers to any reduc-
tion in proteolytic cleavage of mCD28. In some embodi-
ments, the inhibition is a reduction in cleavage of at least 5,
10, 15, 20, 25, 30, 35, 40, 45, 50, 55, 60, 65, 70, 75, 80, 85,
90, 95, 97, 99 or 100%. Each possibility represents a
separate embodiment of the invention. In some embodi-
ments, inhibiting proteolytic cleavage maintains levels of
mCD28 on immune cells. In some embodiments, inhibiting
proteolytic cleavage increases levels of mCD28 on immune
cells. In some embodiments, inhibiting proteolytic cleavage
maintains levels of mCD28 adequate for immune stimula-
tion.

In some embodiments, the reduction in proteolytic cleav-
age is reduction in cleavage by at least one protease. In some
embodiments, the reduction in proteolytic cleavage is reduc-
tion in cleavage by at least one metalloprotease. In some
embodiments, the metalloprotease is MMP-2, ADAM10,
ADAM17 or a combination thereof. In some embodiments,
the metalloprotease is MMP-2, ADAM10, ADAM17, MMP-
13 or a combination thereof. In some embodiments, the
metalloprotease is MMP-2. In some embodiments, the met-
alloprotease is MMP-2 or MMP-13. In some embodiments,
the metalloprotease is MMP-2. In some embodiments, the
metalloprotease is MMP-2, MMP-13 or a combination
thereof.

In some embodiments, the first moiety, is selected from an
antigen binding fragment of an antibody, a Fab fragment, a
single chain antibody, a single domain antibody, a small
molecule and a peptide that specifically binds to CD28. In
some embodiments, the first moiety is a Fab fragment. In
some embodiments, the first moiety is a single chain anti-
body. In some embodiments, the first moiety is a single
domain antibody. In some embodiments, the first moiety is
a peptide that specifically binds to CD28. In some embodiments, the first moiety, is selected from an antigen binding fragment of an antibody, a Fab fragment, a single chain antibody, and a single domain antibody. In some embodiments, the first moiety, the second moiety or both are not full-size antibodies. In some embodiments, the first moiety, the second moiety or both lacks a Fc domain. In some embodiments, the first moiety, the second moiety or both is an antigen binding domain that lacks an Fc domain. In some embodiments, the first moiety, the second moiety or both is a camelid, shark or nanobody.

In some embodiments, the agent is fused to another protein or fragment of a protein. In some embodiments, the second protein or fragment targets the agent to CD28. In some embodiments, the another protein or fragment of a protein is an antigen binding moiety that binds an extracellular domain of CD28.

An example of the first moiety, the second moiety or both includes, but is not limited to, an antibody, an antigen binding fragment of an antibody, a nanobody, a single chain antibody, a single domain antibody, a small molecule, a peptide and a DARPin. In some embodiments, the agent is selected from an antibody, an antigen binding fragment of an antibody, a Fab fragment, a nanobody, a single chain antibody, a single domain antibody, a small molecule, a peptide and a DARPin. In some embodiments, the agent is selected from an antibody, an antigen binding fragment of an antibody, a Fab fragment, a single chain antibody, a single domain antibody, a small molecule, and a peptide with specific binding to CD28. In some embodiments, the agent is a single domain antibody. In some embodiments, the agent is a nanobody. In some embodiments, the agent is a VHH antibody. As used herein, the terms "single domain antibody", "nanobody" and "VHH antibody" are synonymous and used interchangeably. In some embodiments, the peptide has specific binding to CD28. In some embodiments, the agent is a peptide with specific binding to CD28. In some embodiments, the peptide is selected from an antibody, an antigen binding fragment of an antibody, a Fab fragment, a single chain antibody, a single-domain antibody, a nanobody, a VHH antibody and an antibody mimetic. As used herein, the term "antibody mimetic" refers to an organic compound that can specifically bind to a target antigen. In some embodiments, an antibody mimetic is not structurally related to an antibody. Examples of antibody mimetics include, but are not limited to, affilins, affimers, affitins, alphabodies, anticalins, avimers, DARPins, fynomers, Kunitz domain peptides, monobodies, and nanoCLAMPS. In some embodiments, the antibody mimetic is a DARPin. All of these agents are well known in the art and are known to be useful in blocking interactions between receptors and their ligands. Small molecules and proteins that can bind mCD28 may occlude the cleavage site or may cause hinderance or impair access for the protease. In some embodiments, the protein is an antibody mimetic. As used herein, the term "DARPin" refers to a designed ankyrin repeat protein. DARPins are genetically engineered antibody mimetic proteins that are generally highly specific for their protein target. Thus, a DARPin for CD28 may be an example of an agent.

In some embodiments, a Fab fragment comprises a size of about 50 kDa. In some embodiments, a Fab fragment comprises a size of less than 100 kDa. In some embodiments, a Fab fragment comprises a size of less than 80 kDa. In some embodiments, a Fab fragment comprises a size of less than 70 kDa. In some embodiments, a Fab fragment comprises a size of less than 50 kDa. In some embodiments, a Fab fragment comprises a size of 50 kDa or less. In some embodiments, a single chain antibody comprises a size of about 25 kDa. In some embodiments, a single chain antibody comprises a size of less than 50 kDa. In some embodiments, a single chain antibody comprises a size of less than 40 kDa. In some embodiments, a single chain antibody comprises a size of less than 30 kDa. In some embodiments, a single chain antibody comprises a size of less than 25 kDa. In some embodiments, a single chain antibody comprises a size of 25 kDa or less. In some embodiments, a single domain antibody comprises a size of about 15 kDa. In some embodiments, a single domain antibody comprises a size of between 10-20 kDa. In some embodiments, a single domain antibody comprises a size of between 10-17 kDa. In some embodiments, a single domain antibody comprises a size of between 10-16 kDa. In some embodiments, a single domain antibody comprises a size of between 10-15 kDa. In some embodiments, a single domain antibody comprises a size of between 12-15 kDa. In some embodiments, a single domain antibody comprises a size of between 12-16 kDa. In some embodiments, a single domain antibody comprises a size of between 12-17 kDa. In some embodiments, a single domain antibody comprises a size of between 12-20 kDa. In some embodiments, a single domain antibody comprises a size of less than 25 kDa. In some embodiments, a single domain antibody comprises a size of less than 20 kDa. In some embodiments, a single domain antibody comprises a size of less than 15 kDa. In some embodiments, a single domain antibody comprises a size of 15 kDa or less. Due to its small size and that antigen-binding relies on only 3 CDRs, the binding machinery of a single domain antibody, specifically a VHH, is of a convex shape and binds its epitope from only one side and is more thus suited to bind epitopes that are characterized by limited solvent exposure, such as found in protein clefts like the stalk region of membrane anchored CD28. By comparison, Fab fragments and single-chain antibodies comprise 6 CDRs and bind epitopes from at least 2 sides. In some embodiments, binding with only 3 CDRs allows superior access to the mCD28 stalk region as compared to binding with 6 CDRS. In some embodiments, the geometry of single-domain antibody binding is superior for accessing the mCD28 stalk region.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', F(ab')2, single stranded antibody (scFv), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)— Fc fusions and scFv-scFv-Fc fusions.

Immunoglobulin molecules can be of any type (e.g., IgG, IgE, IgM, IgD, IgA and IgY), class (e.g., IgG1, IgG2, IgG3, IgG4, IgA1 and IgA2) or subclass.

The basic unit of the naturally occurring antibody structure is a heterotetrameric glycoprotein complex of about 150,000 Daltons, composed of two identical light (L) chains and two identical heavy (H) chains, linked together by both noncovalent associations and by disulfide bonds. Each heavy and light chain also has regularly spaced intra-chain disulfide bridges. Five human antibody classes (IgG, IgA, IgM, IgD and IgE) exist, and within these classes, various subclasses, are recognized based on structural differences, such as the number of immunoglobulin units in a single antibody molecule, the disulfide bridge structure of the individual units, and differences in chain length and sequence. The class and subclass of an antibody is its isotype. In some embodiments, a Fab fragment has a size of less than 100, 90, 80, 75, 70, 65, 60, 55, or 50 kDa. Each possibility represents a separate embodiment of the invention. In some embodiments, a Fab fragment has a size of less than 50 kDa.

The amino terminal regions of the heavy and light chains are more diverse in sequence than the carboxy terminal regions, and hence are termed the variable domains. This part of the antibody structure confers the antigen-binding specificity of the antibody. A heavy variable (VH) domain and a light variable (VL) domain together form a single antigen-binding site, thus, the basic immunoglobulin unit has two antigen-binding sites. Particular amino acid residues are believed to form an interface between the light and heavy chain variable domains (Chothia et al., J. Mol. Biol. 186, 651-63 (1985); Novotny and Haber, (1985) Proc. Natl. Acad. Sci. USA 82 4592-4596).

The carboxy terminal portion of the heavy and light chains form the constant domains i.e. CH1, CH2, CH3, CL. While there is much less diversity in these domains, there are differences from one animal species to another, and further, within the same individual there are several different isotypes of antibody, each having a different function.

The term "framework region" or "FR" refers to the amino acid residues in the variable domain of an antibody, which are other than the hypervariable region amino acid residues as herein defined. The term "hypervariable region" as used herein refers to the amino acid residues in the variable domain of an antibody, which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Kabat et al.).

Immunoglobulin variable domains can also be analyzed using the IMGT information system (www://imgt.cines.fr/) (IMGT®/V-Quest) to identify variable region segments, including CDRs. See, e.g., Brochet, X. et al, Nucl. Acids Res. J6:W503-508 (2008).

Chothia et al. also defined a numbering system for variable domain sequences that is applicable to any antibody. One of ordinary skill in the art can unambiguously assign this system of "Chothia numbering" to any variable domain sequence, without reliance on any experimental data beyond the sequence itself. As used herein, "Chothia numbering" refers to the numbering system set forth by Chothia et al., Journal of Molecular Biology, "Canonical Structures for the Hypervariable regions of immunoglobulins" (1987) and Chothia et al., Nature, "Conformations of Immunoglobulin Hypervariable Regions" (1989).

As used herein, the terms "single chain antibodies" and "single chain variable fragments" are used synonymously and refer to a fusion protein of variable region of heavy and light chains of immunoglobulins, connected by a short peptide linker. In some embodiments a single chain antibody has a size of less than 50, 45, 40, 35, 30, 25, or 20 kDa. Each possibility represents a separate embodiment of the invention. In some embodiments, a single chain antibody has a size of less than 25 kDa. In some embodiments, the linker of a single chain antibody is between 10 and 25 amino acids. In some embodiments, the linker of a single chain antibody is between 1-40, 5-40, 10-40, 1-35, 5-35, 10-35, 1-30, 5-30, 10-30, 1-25, 5-25 or 10-25 amino acids. Each possibility represents a separate embodiment of the invention. In some embodiments, the single chain antibody comprises a heavy chain of antibody M9. In some embodiments, the single chain antibody comprises a light chain of antibody M9. In some embodiments, the single chain antibody comprises the CDRs of antibody M9.

As used herein, the terms "single domain antibody", "nanobody", "DARPin" and "VHH" are used synonymously and refer to an antibody fragment consisting of a single monomeric variable antibody domain. In some embodiments, the single domain antibody is a camelid antibody. In some embodiments, a camelid is a camel, an alpaca or a llama. In some embodiments, the camelid is a camel. In some embodiments, the camelid is an alpaca. In some embodiments, the camelid is a llama. In some embodiments, the single domain antibody is a shark antibody.

Also, as already indicated herein, the amino acid residues of a Nanobody are numbered according to the general numbering for VHs given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. In this respect, it should be noted that—as is well known in the art for VH domains and for VHH domains— the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.

Alternative methods for numbering the amino acid residues of VH domains, which methods can also be applied in an analogous manner to VHH domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

As used herein, the term "humanized antibody" refers to an antibody from a non-human species whose protein sequences have been modified to increase similarity to human antibodies. A humanized antibody may be produced by production of recombinant DNA coding for the CDRs of the non-human antibody surrounded by sequences that resemble a human antibody. In some embodiments, the humanized antibody is a chimeric antibody. In some embodiments, humanizing comprises insertion of the CDRs of the invention into a human antibody scaffold or backbone. Humanized antibodies are well known in the art and any method of producing them that retains the CDRs of the invention may be employed.

The term "monoclonal antibody" or "mAb" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies and is not to be construed as produced by any specific preparation method. Monoclonal antibodies to be used in accordance with the methods provided herein, may be made by the hybridoma method first described by Kohler et al, Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624-628 (1991) and Marks et al, J. Mol. Biol. 222:581-597 (1991), for example.

The mAb of the present invention may be of any immunoglobulin class including IgG, IgM, IgD, IgE or IgA. A hybridoma producing a mAb may be cultivated in vitro or in vivo. High titers of mAbs can be obtained from in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

"Antibody fragments" comprise a portion of an intact antibody, preferably comprising the antigen binding region thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al, Protein Eng. 8(10): 1057-1062 (1995)); one-armed antibodies, single variable domain antibodies, minibodies, single-chain antibody molecules; multispecific antibodies formed from antibody fragments (e.g., including but not limited to, db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three surfaces of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called a, delta, e, gamma, and micro, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies production is known in the art and is described in Proc. Natl. Acad. Sci. USA, 90:6444-6448 (1993).

The term "multispecific antibody" is used in the broadest sense and specifically covers an antibody that has poly-epitopic specificity. Such multispecific antibodies include, but are not limited to, an antibody comprising a heavy chain variable domain (VH) and a light chain variable domain (VL), where the VHVL unit has polyepitopic specificity, antibodies having two or more VL and VH domains with each VHVL unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s).

A monoclonal antibody of the invention may be prepared using methods well known in the art. Examples include various techniques, such as those in Kohler, G. and Milstein, C, Nature 256: 495-497 (1975); Kozbor et al, Immunology Today 4: 72 (1983); Cole et al, pg. 77-96 in MONOCLO-NAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies, one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

In some embodiments, antibodies and portions thereof include: antibodies, fragments of antibodies, Fab and F(ab')

20

2, single-domain antigen-binding recombinant fragments and natural nanobodies. In some embodiments, the antigen binding fragment is selected from the group consisting of a Fv, Fab, F(ab')₂, scFv or a scFv₂ fragment.

In some embodiments, the present invention provides nucleic acid sequences encoding the agents of the present invention.

For example, the polynucleotide may encode an entire immunoglobulin molecule chain, such as a light chain or a heavy chain. A complete heavy chain includes not only a heavy chain variable region (VH) but also a heavy chain constant region (CH), which typically will comprise three constant domains: CH1, CH2 and CH3; and a "hinge" region. In some situations, the presence of a constant region is desirable.

Other polypeptides which may be encoded by the poly-nucleotide include antigen-binding antibody fragments such as single domain antibodies ("dAbs"), Fv, scFv, Fab' and CHI and CK or CL domain has been excised. As minibodies are smaller than conventional antibodies they should achieve better tissue penetration in clinical/diagnostic use but being bivalent they should retain higher binding affinity than monovalent antibody fragments, such as dAbs. Accordingly, unless the context dictates otherwise, the term "antibody" as used herein encompasses not only whole antibody molecules, but also antigen-binding antibody fragments of the type discussed above. Each framework region present in the encoded polypeptide may comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

Suitably, the polynucleotides described herein may be isolated and/or purified. In some embodiments, the poly-nucleotides are isolated polynucleotides.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring".

In some embodiments, the first moiety comprises three CDRs, wherein CDR1 comprises the amino acid sequence set forth in SEQ ID NO: 1 (INAMG), CDR2 comprises the amino acid sequence as set forth in SEQ ID NO: 2 (AIS-GGGDTYYADSVKG), CDR3 comprises the amino acid sequence as set forth in SEQ ID NO: 3 (DLYGSDYWD).

In some embodiments, the first moiety comprises three CDRs, wherein CDR1 comprises the amino acid sequence set forth in SEQ ID NO: 4 (INAMA), CDR2 comprises the amino acid sequence as set forth in SEQ ID NO: 5 (AITSSGSTNYANSVKG), CDR3 comprises the amino acid sequence as set forth in SEQ ID NO: 6 (DEYGSDYWI).

In some embodiments, the first moiety comprises three CDRs, wherein CDR1 comprises the amino acid sequence set forth in SEQ ID NO: 1 (INAMG), CDR2 comprises the amino acid sequence as set forth in SEQ ID NO: 7 (AITSGGSTNYADSVKG), CDR3 comprises the amino acid sequence as set forth in SEQ ID NO: 8 (DLYGEDYWI).

In some embodiments, the CDRs are numbered according to the Abm method of numbering. In some embodiments, the CDRs are numbered according to the Chothia method of numbering. In some embodiments, the CDRs are numbered according to the Kabat method of numbering.

In some embodiments, CDR1 comprises the amino acid sequence set forth in SEQ ID NO: 29 (INAMX$_1$), wherein X$_1$ is G or A. In some embodiments, CDR2 comprises the amino acid sequence set forth in SEQ ID NO: 30 (AIX$_1$X$_2$X$_3$GX$_4$TX$_5$YAX$_6$SVKG), wherein X$_1$ is S or T, X$_2$ is G or S, X$_3$ is G or S, X$_4$ is D or S, X$_5$ is Y or N, and X$_6$ is D or N. In some embodiments, CDR3 comprises the amino acid sequence set forth in SEQ ID NO: 31 (DX$_1$YGX$_2$DYWX$_3$), wherein X$_1$ is E or L, X$_2$ is E or S, and X$_3$ is D or I. In some embodiments, CDR3 comprises the amino acid sequence set forth in SEQ ID NO: 32 (DX$_1$YGSDYWX$_2$), wherein X$_1$ is E or L, and X$_2$ is D or I.

In some embodiments, the first moiety, the second moiety or both is a single-domain antibody. In some embodiments, the first moiety, the second moiety or both is a VHH antibody. In some embodiments, the first moiety, the second moiety or both is a camelid antibody. In some embodiments, the camelid is a llama. In some embodiments, the first moiety, the second moiety or both comprises no other CDRs other than the CDRs recited hereinabove.

In some embodiments, the first moiety comprises a sequence comprising and/or consisting of

```
                                  (SEQ ID NO: 9)
EVQLVESGGGLVQAGESLRLSCAASGSIASINAMGWYRQAPGSQRELVAA

ISGGGDTYYADSVKGRFTISRDNAKTTVYLQMNSLRPEDTAVYYCVVDLY

GSDYWDWGQGTQVTVSS.
```

In some embodiments, the first moiety comprises a sequence comprising and/or consisting of

```
                                  (SEQ ID NO: 10)
EVQLVESGGGLVQAGGSLRLSCAASGSLFSINAMAWYRQAPGKQRELVAA

ITSSGSTNYANSVKGRFTVSRDNAKNTMYLQMNSLKPEDTAVYYCVVDEY

GSDYWIWGQGTQVTVSS.
```

In some embodiments, the first moiety comprises a sequence comprising and/or consisting of

```
                                  (SEQ ID NO: 11)
QVQLVESGGGLVQAGGSLRLSCAASGSIFSINAMGWYRQAPGKQRERVAA

ITSSGSTNYADSVKGRFTISRDNAKNTVYLQMNNLEPRDAGVYYCVVDLY

GEDYWIWGQGTQVTVSS.
```

In some embodiments, the VHH sequences further comprise a His tag. In some embodiments, the His tag is at least 1, 2, 3, 4, 5, 6, 7, 8, 9, or 10 histidine residues. Each possibility represents a separate embodiment of the invention. In some embodiments, the His tag consists of 6 histidine residues. In some embodiments, the His tag is connected to the VHH via a linker. In some embodiments, the linker is a peptide linker. In some embodiments, the linker is an alanine repeat linker. In some embodiments, the alanine repeat comprises at least 1, 2, 3, 4, 5, 6, 7, 8, 9, or 10 alanine residues. Each possibility represents a separate embodiment of the invention. In some embodiments, the alanine repeat linker consists of 3 alanine residues. In some embodiments, the His-tag is a six His tag.

In some embodiments, the VHH sequences found to specifically bind the stalk region of human CD28 and comprising a His tag are:

```
                          (SEQ ID NO: 33, clone 2A1)
EVQLVESGGGLVQAGESLRLSCAASGSIASINAMGWYRQAPGSQRELVAA

ISGGGDTYYADSVKGRFTISRDNAKTTVYLQMNSLRPEDTAVYYCVVDLY

GSDYWDWGQGTQVTVSSAAAHHHHHH;

(SEQ ID NO: 34, clone 4A4)
EVQLVESGGGLVQAGGSLRLSCAASGSLFSINAMAWYRQAPGKQRELVAA

ITSSGSTNYANSVKGRFTVSRDNAKNTMYLQMNSLKPEDTAVYYCVVDEY

GSDYWIWGQGTQVTVSSAAAHHHHHH;
and (SEQ ID NO: 35, clone 4A1)
QVQLVESGGGLVQAGGSLRLSCAASGSIFSINAMGWYRQAPGKQRERVAA

ITSGGSTNYADSVKGRFTISRDNAKNTVYLQMNNLEPRDAGVYYCVVDLY

GEDYWIWGQGTQVTVSSAAAHHHHHH.
```

In some embodiments, the VHH sequences further comprise a cysteine at the C-terminus of the His tag. In some embodiments, the cysteine is separated from the His-tag by a spacer. In some embodiments, the spacer is a single amino acid. In some embodiments, the spacer is 1, 2, 3, 4, 5, 6, 7, 8, 9, or 10 amino acids. Each possibility represents a separate embodiment of the invention. In some embodiments, the spacer comprises or consists of a glycine residue. In some embodiments, the VHH sequences found to specifically bind the stalk region of human CD28 comprising a His-tag and a C-terminal cysteine separated from the His-tag by a glycine are selected from:

```
                                  (SEQ ID NO: 36)
EVQLVESGGGLVQAGESLRLSCAASGSIASINAMGWYRQAPGSQRELVAA

ISGGGDTYYADSVKGRFTISRDNAKTTVYLQMNSLRPEDTAVYYCVVDLY

GSDYWDWGQGTQVTVSSAAAHHHHHHGC;

(SEQ ID NO: 37)
EVQLVESGGGLVQAGGSLRLSCAASGSLFSINAMAWYRQAPGKQRELVAA

ITSSGSTNYANSVKGRFTVSRDNAKNTMYLQMNSLKPEDTAVYYCVVDEY

GSDYWIWGQGTQVTVSSAAAHHHHHHGC;
and (SEQ ID NO: 38)
QVQLVESGGGLVQAGGSLRLSCAASGSIFSINAMGWYRQAPGKQRERVAA

ITSGGSTNYADSVKGRFTISRDNAKNTVYLQMNNLEPRDAGVYYCVVDLY

GEDYWIWGQGTQVTVSSAAAHHHHHHGC.
```

In some embodiments, the first moiety comprises three heavy chain CDRs (CDR-H) and three light chain CDRs (CDR-L), wherein: CDR-H1 comprises the amino acid sequence set forth in SEQ ID NO: 39 (GYTLTNY), CDR-H2 comprises the amino acid sequence as set forth in SEQ ID NO: 40 (NTYTGK), CDR-H3 comprises the amino acid sequence as set forth in SEQ ID NO: 41 (GDANQQFAY), CDR-L1 comprises the amino acid sequence as set forth in SEQ ID NO: 42 (KASQDINSYLS), CDR-L2 comprises the amino acid sequence as set forth in SEQ ID NO: 43 (RANRLVD), and CDR-L3 comprises the amino acid sequence as set forth in SEQ ID NO: 44 (LQYDEFPPT).

In some embodiments, the first moiety comprises three heavy chain CDRs (CDR-H) and three light chain CDRs (CDR-L), wherein: CDR-H1 comprises the amino acid sequence set forth in SEQ ID NO: 12 (GFTFSSYYMS), CDR-H2 comprises the amino acid sequence as set forth in SEQ ID NO: 13 (TISDGGDNTYYAGTVTG), CDR-H3 comprises the amino acid sequence as set forth in SEQ ID NO: 14 (IHWPYYFDS), CDR-L1 comprises the amino acid sequence as set forth in SEQ ID NO: 15 (RASSSVSYMN), CDR-L2 comprises the amino acid sequence as set forth in SEQ ID NO: 16 (ATSDLAS), and CDR-L3 comprises the amino acid sequence as set forth in SEQ ID NO: 17 (QQWSSHPPT). This antibody is herein referred to as M9.

In some embodiments, the first moiety comprises a heavy chain comprising the amino acid sequence DVKLVESGG-GLVKLGGSLKLSCVASGFTFSSYYMSWVRQTPEKR-LEWVATISDGGDN TYYAGTVTGRFTISRDFAKNT-LYLQMNSLTSEDTAVYYCARIHWPYYFDSWGQGTTL TVSS (SEQ ID NO: 45). In some embodiments, the variable region of the heavy chain comprises and/or consists of SEQ ID NO: 45. In some embodiments, the agent comprises a heavy chain comprising an amino acid sequence encoded by the nucleotide sequence GACGTGAAGCTCGTG-GAGTCTGGGGGAGGCTTAGTGAAGCTTGGAGGG-TCCCTGA AACTCTCCTGTGTAGCCTCTGGATT-CACTTTCAGTAGCTATTACATGTCTTGGGTTC GCC-AGACTCCGGAAGAGGCTGGAGTGGGTC-GCGACCATAAGTGATGGTGGTGA TAACACCTAC-TACGCAGGCACTGTGACGGGCCGATTCACCATCT-CCAGAGACTTTG CCAAGAACACCCTGTACCTG-CAAATGAACAGTCTGACCTCTGAGGACACAGCCGT GTATTACTGTGCAAGAATTCATTGGCCTTACTAT-TTTGACTCCTGGGGCCAAGGCA CCACTCTCACA-GTCTCCTCA (SEQ ID NO: 46). In some embodiments, the heavy chain consists of SEQ ID NO: 46. Antibody M9 was sequenced and found to have a heavy chain consisting of SEQ ID NO: 45. The CDRs of this heavy chain, as determined using Chothia scheme, are SEQ ID NOs: 12-14.

In some embodiments, the first moiety comprises a light chain comprising the amino acid sequence (SEQ ID NO: 47)
QFVLSQSPAILSASPGEMLTMTCRASSSVSYMNWYQQKPGSSPKPWIYAT

SDLASGVPARFSGSGSGTSYSLTISRVEAEDAATYYCQQWSSHPPTFGGG

TKLEIR.

In some embodiments, the variable region of the light chain comprises and/or consists of SEQ ID NO: 47. In some embodiments, the first moiety comprises a light chain comprising an amino acid sequence encoded by the nucleotide sequence CAATTTGTTCTCTCCCAGTCTCCAGCAA-TCCTGTCTGCATCTCCCGGGGAGATGCTC ACAA-TGACTTGCAGGGCCAGCTCAAGTGTAAGTTATAT-GAACTGGTATCAGCAGA AGCCAGGATCTTCCCC-CAAACCCTGGATTTATGCCACATCCGACCTGGCT-TCTGGA GTCCCTGCTCGCTTCAGTGGCAGTGGG-TCTGGGACCTCTTATTCTCTCACAATCAGC AGAG-TGGAGGCTGAAGATGCTGCCACTTATTACTGCCAGCAGTGGAGTAGTCACCC ACCCACGTTCG-GAGGGGGGGACCAAGCTGGAAATAAGA (SEQ ID NO: 48). In some embodiments, the light chain consists of SEQ ID NO: 48. Antibody M9 was sequenced and found to have a light chain consisting of SEQ ID NO: 47. The CDRs of this light chain, as determined using Chothia scheme, are SEQ ID NOs: 15-17.

In some embodiments, the first moiety binds as a mono-mer. In some embodiments the first moiety binds as a dimer. In some embodiments, the first moiety binds as a monomer and/or a dimer. In some embodiments, the first moiety binds as a dimer, but does not crosslink and/or activate mCD28. In some embodiments, the first moiety binds as a dimer, but only binds a single molecule of CD28. In some embodi-ments, the first moiety binds monomeric CD28. In some embodiments, the first moiety, the second moiety or both binds dimeric CD28. In some embodiments, the first moiety binds monomeric and/or dimeric CD28.

In some embodiments, the agent, the first moiety, the second moiety or a combination thereof is not a CD28 agonist. In some embodiments, the agent, the first moiety, the second moiety or a combination thereof is not a CD28 antagonist. In some embodiments, the agent, the first moiety, the second moiety or a combination thereof is neither a CD28 agonist or antagonist.

The term "agonist" generally refers to a molecule, com-pound or agent that binds to a receptor and activates, fully or partially, the receptor. In some embodiments, the agonist binds at the same site as the natural ligand. In some embodiments, the agonist binds at an allosteric site different from the binding site of the natural ligand. The term "antago-nist" generally refers to a molecule, compound or agent that binds to a receptor at the same site as an agonist or another site, does not activate the receptor and does one or more of the following: interferes with or blocks activation of the receptor by a natural ligand, and interferes with or blocks activation of the receptor by a receptor agonist. In some embodiments, the agent, the first moiety, the second moiety or a combination thereof bind to mCD28 but do not activate or block activation of the receptor. In some embodiments, the agent, the first moiety, the second moiety or a combi-nation thereof do not block activation by CD86. In some embodiments, the agent, the first moiety, the second moiety or a combination thereof do not bind mCD28.

As used herein, a "direct agonist/antagonist" refers to a molecule that binds to a receptor (mCD28) and by binding increases/decreases signaling by that molecule. In the case of mCD28 an agonist would bind mCD28 and by binding increase mCD28 signaling in the cell. In some embodiments, the agonist increases T cell activation. In some embodi-ments, the agonist increases T cell proliferation. In some embodiments, the agonist increases pro-inflammatory cyto-kine secretion. Pro-inflammatory cytokines are well known in the art and are known to be secreted by activated T cells. Examples of pro-inflammatory cytokines include, but are not limited to, TNFα, IFNγ, IL-1B, IL-2, and IL-6. In some embodiments, the pro-inflammatory cytokine is IFNγ. In some embodiments, the pro-inflammatory cytokine is IL-2. In the case of mCD28 an antagonist would bind mCD28 and by binding decrease mCD28 signaling in the cell. In some embodiments, the antagonist decreases T cell activation, decreases T cell proliferation and/or decreases pro-inflam-matory cytokine secretion. A molecule that effects a recep-tor's signaling by contacting its ligand, contacting an inhibi-tor, contacting a co-receptor or contacting any molecule other than the receptor in question in order to modify receptor signaling is not considered a direct agonist/antagonist. In some embodiments, the agent of the invention contacts sCD28 in serum and thereby allows for increased signaling through mCD28 on cells. Though the result is increased mCD28 signaling the antibody is not a mCD28 agonist or direct agonist as its binding to mCD28 does not increase the receptors signaling.

In some embodiments, the first moiety does not bind the ligand binding domain of mCD28. In some embodiments, the agent, the first moiety, the second moiety or a combination thereof does not obscure or block access to the ligand binding domain. In some embodiments, the agent, the first moiety, the second moiety or a combination thereof does not bind, obscure or block access to the IgV domain of sCD28. In some embodiments, the IgV domain is the ligand binding domain. In some embodiments, the ligand binding domain comprises amino acids 28-137 of SEQ ID NO: 20. In some embodiments, the ligand binding domain comprises or consists of the amino acid sequence MLVAYD-NAVNLSCKYSYNLFSREFRASLHKGLDSAVEVCV-VYGNYSQQLQVYSKTG FNCDGKLGNESVTFYLQN-LYVNQTDIYFCKIEVMYPPPYLDNEKSNGTIIHVKG (SEQ ID NO: 49). In some embodiments, the agent, the first moiety, the second moiety or a combination thereof does not inhibit binding of sCD28 to a ligand. In some embodiments, the CD28 ligand is selected from: CD80, CD86 and ICOSL. In some embodiments, the CD28 ligand is CD86. In some embodiments, the CD28 ligand is CD80. In some embodiments, the CD28 ligand is ICOSL. In some embodiments, CD86 is CD86-Fc. In some embodiments, CD80 is CD80-Fc.

In some embodiments, the first moiety binds a stalk region of CD28. In some embodiments, the first moiety binds a membrane proximal region of mCD28. In some embodiments, the stalk region comprises the sequence GKHLCPSPLFPGPSKP (SEQ ID NO: 50). In some embodiments, the stalk region comprises the sequence KGKHLCPSPLFPGPS (SEQ ID NO: 51). In some embodiments, the stalk region comprises or consists of the sequence HVKGKHLCPSPLFPGPSKP (SEQ ID NO: 52). In some embodiments, a fragment of the CD28 extracellular domain is the stalk region. In some embodiments, the first moiety binding to CD28 prevents cleavage of CD28. In some embodiments, the first moiety binding to CD28 prevents shedding of CD28 from a cell.

In some embodiments, the first moiety binds at a cleavage site in the stalk region. In some embodiments, the first moiety binds at a cleavage site within mCD28. In some embodiments, the first moiety binds at a cleavage site of at least one protease. In some embodiments, the first moiety binds at a cleavage site of MMP-2.

In some embodiments, the first moiety does not bind the ligand binding domain of mCD28. In some embodiments, the agent, the first moiety, the second moiety or a combination thereof does not obscure or block access to the ligand binding domain. In some embodiments, the first moiety binds a cleavage site. In some embodiments, the first moiety obscures, occludes or blocks access to a cleavage site. In some embodiments, the first moiety binds, blocks, occludes or obscures a protease cleavage site. In some embodiments, first moiety does not bind a protease cleavage site but occludes the site. In some embodiments, first moiety blocks access to a protease cleavage site. In some embodiments, first moiety, the second moiety, the agent of a combination thereof generates steric hinderance that blocks a protease cleavage site. In some embodiments, the first moiety does not bind a protease cleavage site but binding of the agent generates a conformational change to mCD28 that blocks the protease cleavage site. In some embodiments, binding of the first moiety generates a conformational change to mCD28 that blocks a protease cleavage site. In some embodiments, the protease is MMP-2. In some embodiments, the protease is MMP-13. In some embodiments, the cleavage site is a cleavage motif. In some embodiments, the MMP-2 cleavage motif is PXX/X, wherein the last X is a hydrophobic residue. In some embodiments, the PXX/X motif in CD28 is PSP/L. In some embodiments, the protease cleavage site is amino acids 142-145 (PSPL) of SEQ ID NO: 20. In some embodiments, the protease cleavage site is amino acids 124-127 (PSPL) of SEQ ID NO: 21. In some embodiments, the protease cleavage site is amino acids 9-12 (PSPL) of SEQ ID NO: 52. In some embodiments, the first moiety blocks accesses of a protease to a cleavage site. In some embodiments, the first moiety binds to PSPL in a stalk domain of mCD28.

In some embodiments, the cleavage site is before a leucine. In some embodiments, the cleavage site is before a valine. In some embodiments, the cleavage site is before an aromatic amino acid. In some embodiments, the cleavage site is before a leucine, valine and/or aromatic amino acid. In some embodiments, the aromatic amino acid is selected from phenylalanine, tryptophan, tyrosine and histidine. In some embodiments, the cleavage site is before any one of histidine 134, valine 135, histidine 139, leucine 140, leucine 145, and phenylalanine 146 of SEQ ID NO: 20. In some embodiments, the cleavage site is before histidine 134, valine 135, histidine 139, leucine 140, leucine 145, or phenylalanine 146 of SEQ ID NO: 20. Each possibility represents a separate embodiment of the invention. In some embodiments, the cleavage site is before leucine 145 of SEQ ID NO: 20. In some embodiments, the cleavage site is before leucine 145 of SEQ ID NO: 1. In some embodiments, the cleavage site is before leucine 127 of SEQ ID NO: 21.

In some embodiments, the first moiety does not bind a stalk region of CD28 with a mutated cleavage site. In some embodiments, the stalk region of CD28 with a mutated cleavage site is not a substrate for a protease. In some embodiments, the stalk region of CD28 with a mutated cleavage site is not a substrate for a metalloprotease. In some embodiments, the stalk region of CD28 with a mutated cleavage site is not a substrate for a matrix metalloprotease. In some embodiments, the stalk region of CD28 with a mutated cleavage site is not a substrate for matrix metalloprotease 2 (MMP-2). In some embodiments, the stalk region of CD28 with a mutated cleavage site is not a substrate for matrix metalloprotease 13 (MMP-13). In some embodiments, the mutated cleavage site is a mutation of leucine 145 of SEQ ID NO: 20. In some embodiments, the mutated cleavage site is an amino acid substitution for leucine 145 of SEQ ID NO: 20. In some embodiments the amino acid substitution for leucine 145 of SEQ ID NO: 20 is a lysine.

In some embodiments, the agent, the first moiety, the second moiety or a combination thereof does not modulate CD28 function and/or signaling. In some embodiments, the agent, the first moiety, the second moiety or a combination thereof does not degrade mCD28. In some embodiments, the agent, the first moiety, the second moiety or a combination thereof does not lead to or facilitate mCD28 degradation. In some embodiments, the signaling is mCD28-mediated immune cell activation. In some embodiments, the agent, the first moiety, the second moiety or a combination thereof does not inhibit immune cell activation. In some embodiments, the agent, the first moiety, the second moiety or a combination thereof does not induce CD28 receptor internalization or recycling. Co-stimulation via mCD28 is essential for immune activation of T-cells. Proteolytic cleavage removes the ligand-binding domain in the extracellular region of CD28 from the transmembrane and cytoplasmic portions of the protein which remain in the membrane. Thus, cleaved CD28 cannot signal and cannot contribute to T cell activation. Thus, an agent that blocks cleavage, and is also an antagonist does not allow for mCD28 activation. Similarly, an agent that blocks cleavage, but is also an agonist could induce aberrant T-cell activation, and potentially an autoimmune response.

In some embodiments, the agent does not reduce surface levels of mCD28 on an immune cell. In some embodiments, the immune cell is a T cell. In some embodiments, the agent reduces surface levels of mCD28 by less than 50, 40, 30, 25, 20, 15, 10, 7, 5, 3, 2 or 1%. Each possibility represents a separate embodiment of the invention.

In some embodiments, the binding of the agent to a cell does not kill the cell. In some embodiments, the binding of the agent to a cell does not lead to death of the cell. In some embodiments the agent does not induce antibody dependent cell-mediated cytotoxicity (ADCC). In some embodiments, the agent does not induce complement-dependent cytotoxicity (CDC). In some embodiments, the agent does not induce ADCC and/or CDC. In some embodiments, the agent is an antibody and comprises an IgG2 or IgG4 domain. In some embodiments, the antibody comprises an IgG2 domain. In some embodiments, the antibody comprises an IgG4 domain. In some embodiments, the antibody comprises an IgG1 or IgG3 mutated to reduce cell death mediated by binding of the antibody. In some embodiments, the mutation mutates a Fc receptor binding domain. In some embodiments, a Fc domain of the antibody is engineered or mutated to decrease CDC, ADCC or both. Fc engineering is well known in the art, and any mutation or amino acid change that is known to decrease antibody mediated cell killing may be used.

In some embodiments, the agent, the first moiety, the second moiety or a combination thereof lacks an Fc domain. In some embodiments, the first moiety, the second moiety or both is an antigen binding domain that lacks an Fc domain. In some embodiments, the first moiety, the second moiety or both is a single-domain antibody. In some embodiments, the first moiety, the second moiety or both is a camelid, shark or nanobody.

In some embodiments, the first moiety, the second moiety or both is a non-antibody protein. In some embodiments, the first moiety, the second moiety or both is a small molecule. In some embodiments, the agent, the first moiety, the second moiety or a combination thereof is a nucleic acid molecule. In some embodiments, the agent, the first moiety, the second moiety or a combination thereof is a synthetic peptide. In some embodiments, the agent, the first moiety, the second moiety or a combination thereof is a synthetic binding protein. In some embodiments, the synthetic peptide is based on a non-antibody scaffold. In some embodiments, the agent, the first moiety, the second moiety or a combination thereof is an antibody mimetic. In some embodiments, the antibody mimetic has a molar mass of less than 100, 90, 80, 70, 60, 50, 40, 30 or 20 kDa. Each possibility represents a separate embodiment of the invention. In some embodiments, the agent, the first moiety, the second moiety or a combination thereof is a nucleic acid aptamer. In some embodiments, the aptamer is DNA. In some embodiments, the aptamer is RNA. In some embodiments, the aptamer is DNA or RNA. Examples of antibody mimetics include, but are not limited to, affilins, affimers, affitins, alphabodies, anticalins, avimers, DARPins, fynomers, Kunitz domain peptides, monobodies, and nanoCLAMPS. In some embodiments, the antibody mimetic is a DARPin.

In some embodiments, the first moiety inhibits proteolytic cleavage by at least one protease. In some embodiments, the protease is a metalloprotease. In some embodiments, the protease is a matrix metalloprotease. In some embodiments, the protease is a serine protease. In some embodiments, the protease is a cysteine protease. In some embodiments, the protease is a threonine protease. In some embodiments, the protease is a serine, cysteine or threonine protease. In some embodiments, the protease is an aspartic protease. In some embodiments, the protease is a glutamic protease. In some embodiments, the protease is selected from an aspartic, a glutamic, a serine, a cysteine and a threonine protease. In some embodiments, the protease is an asparagine peptide lyases. In some embodiments, the protease is a sheddase. In some embodiments, the metalloprotease is an exopeptidase. In some embodiments, the metalloprotease is an endopeptidase. In some embodiments, the metalloprotease is an exopeptidase or endopeptidase. In some embodiments, the metalloprotease is zinc catalyzed. In some embodiments, the metalloprotease is cobalt catalyzed. In some embodiments, the metalloprotease is matrix metalloproteinase-2 (MMP-2). In some embodiments, the metalloprotease is matrix metalloproteinase-13 (MMP-13). In some embodiments, the metalloprotease is ADAM10. In some embodiments, the metalloprotease is ADAM17. In some embodiments, the metalloprotease is ADAM10, MMP-2, and/or ADAM17. In some embodiments, the metalloprotease is ADAM10, MMP-2, MMP-13 and/or ADAM17. In some embodiments, the metalloprotease is MMP-2, ADAM10, ADAM17 or a combination thereof. In some embodiments, the metalloprotease is MMP-2, MMP-13, ADAM10, ADAM17 or a combination thereof.

In some embodiments, the agent comprises a polypeptide. In some embodiments, the polypeptide is fused to a shielding molecule that is not a polypeptide. As used herein, the term "shielding molecule" refers to a moiety that protects the first moiety from degradation, clearance or removal. In some embodiments, the shielding molecule is a polymer. In some embodiments, the polymer is a copolymer. In some embodiments, the polymer is a biodegradable polymer. In some embodiments, the polymer is a polysaccharide polymer. In some embodiments, the polymer is a protein polymer. In some embodiments, the protein polymer is an unstructured protein polymer. Examples of polymers include, but are not limited to, natural polysaccharides, semi-synthetic polysaccharides, O-linked oligosaccharides, N-linked oligosaccharides, dextran, agarose, alginate, chitosan, carrageenan, hydroxyethyl starch (HES), polysialic acid, hyaluronic acid, homo-amino acid polymers, elastin-like polymers, XTEN, PAS, polyethylene glycol (PEG), Poly-(glycolic acid) (PGA) and poly-(lactic acid) (PLA), poly-(lactic-co-glycolic acid) (PLGA) and Poly-D,L-lactic Acid (PDLLA). In some embodiments, the polymer is a biocompatible polymer. In some embodiments, the shielding molecule comprises a polyethylene glycol (PEG) molecule. In some embodiments, the polymer is PEG. In some embodiments, the polymer is selected from PEG, PLGA, PGA, PLA, and PDLLA. In some embodiments, the shielding molecule comprises a PLGA molecule. In some embodiments, the shielding molecule comprises a PGA molecule. In some embodiments, the shielding molecule comprises a PLA molecule. In some embodiments, the shielding molecule comprises a PDLLA molecule. In some embodiments, the shielding molecule comprises an oligosaccharide polymer selected from dextran, agarose, alginate, chitosan, carrageenan, HES, polysialic acid and hyaluronic acid. In some embodiments, the shielding molecule comprises a protein polymer selected from XTEN and PAS. In some embodiments, the shielding molecule comprises a plurality of PEG molecules.

In some embodiments, the agent comprises a polypeptide fused to a PEG molecule or to a plurality of PEG molecules. In some embodiments, the agent comprises a polypeptide but does not comprise a PEG molecule. In some embodiments, the agent comprises a polypeptide fused to a polymer molecule or to a plurality of polymer molecules.

In some embodiments, a second moiety comprises a PEG molecule. In some embodiments, a second moiety comprises a plurality of PEG molecules. In some embodiments, the second moiety is polyethylene glycol (PEG). In some embodiments, the second moiety is a polyethylene glycol (PEG) molecule. In some embodiments, the second moiety comprises PEG or a PEG molecule. In some embodiments, the PEG is linear PEG. In some embodiments, the PEG is chained PEG. In some embodiments, the PEG is chains of PEG. In some embodiments, the PEG is branched PEG. In some embodiments, the PEG comprises PEG methyl ether. In some embodiments, the PEG is PEG dimethyl ether.

In some embodiments, the PEG is low molecular weight PEG. In some embodiments, the PEG is high molecular weight PEG. In some embodiments, the PEG comprises a molecular weight of at least 100, 200, 300, 400, 500, 600, 700, 800, 900, 1000, 1500, 2000, 2500, 3000, 3500, 4000, 4500, 5000, 10000, 15000 or 20000 grams/mol. Each possibility represents a separate embodiment of the invention. In some embodiments, the PEG comprises a molecular weight of at most 500, 600, 700, 800, 900, 1000, 1500, 2000, 2500, 3000, 3500, 4000, 4500, 5000, 10000, 15000, 20000, 25000, 30000, 35000, 40000, 45000, or 50000 grams/mol. Each possibility represents a separate embodiment of the invention. In some embodiments, the PEG comprises a molecular weight of about 100, 200, 300, 400, 500, 600, 700, 800, 900, 1000, 1500, 2000, 2500, 3000, 3500, 4000, 4500, 5000, 10000, 15000, 2000, 2500, 3000, 3500, 4000, 4500, 5000, 10000, 15000, 20000, 25000, 30000, 35000, 40000, 45000, or 50000 grams/mol. Each possibility represents a separate embodiment of the invention. In some embodiments, the PEG comprises a molar mass of at least 2 KDa. In some embodiments, the PEG comprises a size of at least 2 KDa. In some embodiments, the PEG comprises a molar mass of between 2 and 40 KDa. In some embodiments, the PEG comprises a size of between 2 and 40 KDa. In some embodiments, a PEG of less than 2 KDa does not produce half-life extension.

In some embodiments, the PEG molecule or molecules is attached to the polypeptide at a carboxylic acid residue. In some embodiments, the PEG molecule or molecules is attached to the polypeptide at a cysteine residue. In some embodiments, the PEG molecule or molecules is attached to the polypeptide at an aspartic acid residue. In some embodiments, the PEG molecule or molecules is attached to the polypeptide at a glutamic acid residue. In some embodiments, the PEG molecule or molecules is attached to the polypeptide at a lysine residue. In some embodiments, the PEG molecule or molecules is attached to the polypeptide at an aspartic acid residue, a glutamic acid residue, a lysine residue or a cysteine residue, each possibility represents a separate embodiment of the invention. In some embodiments, the PEG conjugated to a cysteine via a thiol linkage. In some embodiments, the PEG is conjugated to a C-terminus of the first moiety. In some embodiments, the PEG is conjugated to a C-terminus of the linker. In some embodiments, the PEG is conjugated to an amino acid residue proximal to a C-terminus of the first moiety. In some embodiments, the PEG is conjugated to an amino acid residue proximal to a C-terminus of the linker. In some embodiments, proximal is within 10 amino acids. It will be understood by a skilled artisan that conjugation close to the C-terminus will keep the PEG moiety away from the CDRs and thus decrease the chance of interfering with binding.

As used herein, "PEGylation" is the process of both covalent and non-covalent attachment or amalgamation of PEG to molecules and macrostructures. Methods of PEGylation are well known in the art and are disclosed in for example U.S. Pat. No. 7,610,156, which is incorporated by reference herein.

In some embodiments, the PEG is conjugated directly to the first moiety. In some embodiments, the PEG is conjugated directly to the linker. In some embodiments, the conjugation is an irreversible conjugation. In some embodiments, the PEG is conjugated to a chemical group and the chemical group is bound to the first moiety. In some embodiments, the PEG is conjugated to a chemical group and the chemical group is bound to the linker. In some embodiments, bond between the chemical group and the first moiety or linker is reversible. For example, a PEG substituted with an SPDP group (2-pyridyl-dithio, also known as OPSS-ortho-pyridine disulfide) can react via said group with a cysteine residue to form a reversible disulfide bond. In some embodiments, the PEG is irreversible conjugated. In some embodiments, the PEG is reversibly conjugated.

In some embodiments, the agent comprises a linker. In some embodiments, the at least two moieties are separated by at least one linker. In some embodiments, the at least two moieties are separated by a linker. In some embodiments, the two moieties are separated by a linker. In some embodiments, the two moieties are joined by a linker. In some embodiments, the agent comprises a linker between at least two moieties. In some embodiment, the agent comprises a linker between a first moiety and a second moiety.

In some embodiments, the linker is a peptide linker. In some embodiments, the linker is a flexible linker. In some embodiments, a flexible linker comprises or consists of at least one GGGGS (SEQ ID NO: 18) sequence. In some embodiments, a flexible linker comprises or consists of at least one GGGS sequence. In some embodiments, a flexible linker comprises or consists of at least one GGGGS repeat. In some embodiments, a flexible linker comprises or consists of 1, 3, or 7 GGGGS repeats. Each possibility represents a separate embodiment of the invention. In some embodiments, a flexible linker comprises or consists of 1, 2, 3, 4, 5, 6, 7, 8, 9, or 10 GGGGS repeats. Each possibility represents a separate embodiment of the invention. In some embodiments, a flexible linker comprises or consists of 1, 2, 3, 4, 5, 6, 7, 8, 9, or 10 GGGS repeats. Each possibility represents a separate embodiment of the invention. In some embodiments, a flexible linker comprises or consists of 1 GGGGS repeat. In some embodiments, a flexible linker comprises or consists of 3 GGGGS repeats. In some embodiments, a flexible linker comprises or consists of 7 GGGGS repeats.

In some embodiments, the linker is of a length sufficient to allow binding of the first moiety to mCD28. In some embodiments, the linker is of a length sufficient to allow binding of the first moiety to its target epitope. In some embodiments, the linker is of a length sufficient to allow binding of the first moiety to the stalk region of mCD28 on a cell. It will be understood by a skilled artisan that the connection of a protective moiety to a small moiety capable of binding the stalk region of mCD28 on the cell surface will need to be of a sufficient length so that the protective moiety does not generate steric hindrance that would perturb the ability of the first moiety to bind. Thus, the linker must be of a sufficient length to allow a range of movement of the first moiety that allows it to access the stalk domain. In some embodiments, the agent does not induce mCD28 crosslinking. In some embodiments, the agent does not induce mCD28 crosslinking that induces immune activation.

In some embodiments, the linker comprises or consists of at least 1, 2, 3, 4, 5, 6, 7, 8, 9, 10, 11, 12, 13, 14, 15, 16, 17, 18, 19, 20, 25, 30, 35, 40, 45 or 50 amino acids. Each possibility represents a separate embodiment of the invention. In some embodiments, the linker comprises or consists of at least 1 amino acid. In some embodiments, the linker comprises or consists of at least 2 amino acids. In some embodiment, the linker is a dipeptide. In some embodiments, the dipeptide is GC. In some embodiments, the linker comprises a cysteine. In some embodiments, the cysteine is a C-terminal cysteine. In some embodiments, the cysteine is proximal to the C-terminus. In some embodiments, proximal is within 50, 45, 40, 35, 30, 25, 20, 15, 10, 5, 3, 2 or 1 amino acid of the C-terminus. Each possibility represents a separate embodiment of the invention. In some embodiments, proximal is within 10 amino acids of the C-terminus. In some embodiments, the C-terminus is the C-terminus of the first moiety. In some embodiments, the C-terminus is the C-terminus of the linker. In some embodiments, the linker comprises or consists of at least 5 amino acids. In some embodiments, the linker comprises or consists of at least 10 amino acids. In some embodiments, the linker comprises or consists of at least 15 amino acids. In some embodiments, the linker comprises or consists of at least 35 amino acids. In some embodiments, the linker comprises or consists of at most 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 amino acids. Each possibility represents a separate embodiment of the invention. In some embodiments, the linker comprises or consists of at most 5 amino acids. In some embodiments, the linker comprises or consists of at most 15 amino acids. In some embodiments, the linker comprises or consists of at most 20 amino acids. In some embodiments, the linker comprises or consists of at most 30 amino acids. In some embodiments, the linker comprises or consists of at most 35 amino acids. In some embodiments, the linker comprises or consists of at most 40 amino acids. In some embodiments, the linker comprises or consists of at most 50 amino acids. In some embodiments, the linker comprises or consists of between 5-100, 5-75, 5-50, 5-35, 5-15, 10-100, 10-75, 10-50, 10-35, 10-30, 10-20, 15-100, 15-75, 15-50, 15-35, 15-30, 15-20, 20-100, 20-75, 20-50, 20-35, 20-30, 25-100, 25-75, 25-50, 25-35, 20-30, 35-100, 35-75 or 35-50 amino acids. Each possibility represents a separate embodiment of the invention. In some embodiments, the linker comprises or consists of between 5-35 amino acids. In some embodiments, the linker comprises or consists of between 15-35 amino acids. In some embodiments, the linker comprises or consists of between 5-50 amino acids. In some embodiments, the linker comprises or consists of between 15-50 amino acids. In some embodiments, the linker comprises or consists of between 35 and 50 amino acids. In some embodiments, the linker comprises or consists of between 10 and 20 amino acids. In some embodiments, the linker comprises or consists of between 10 and 30 amino acids. In some embodiments, the linker comprises or consists of between 15 and 20 amino acids. In some embodiments, the linker comprises or consists of between 15 and 30 amino acids. In some embodiments, the linker comprises or consists of between 10 and 40 amino acids. In some embodiments, the linker comprises or consists of between 20 and 40 amino acids.

In some embodiments, the C-terminus of the first moiety is linked to the linker. In some embodiments, the N-terminus of the first moiety is linked to the linker. In some embodiments, the C-terminus of the second moiety is linked to the linker. In some embodiments, the N-terminus of the second moiety is linked to the linker. In some embodiments, the C-terminus of the first moiety is linked to the linker and the N-terminus of the second moiety is linked to the linker. In some embodiments, the N-terminus of the first moiety is linked to the linker and the C-terminus of the second moiety is linked to the linker. In some embodiments, the C-terminus of the first moiety is linked to the N-terminus of the peptide linker. In some embodiments, the N-terminus of the first moiety is linked to the C-terminus of the peptide linker. In some embodiments, the C-terminus of the second moiety is linked to the N-terminus of the peptide linker. In some embodiments, the N-terminus of the second moiety is linked to the C-terminus of the peptide linker. In some embodiments, the C-terminus of the first moiety is linked to the N-terminus of the peptide linker and the C-terminus of the peptide linker is linked to the N-Terminus of the second moiety. In some embodiments, the N-terminus of the first moiety is linked to the C-terminus of the peptide linker and the N-terminus of the peptide linker is linked to the C-terminus of the second linker.

As used herein, the term "linked" refers to any method of attachment known in the art by which two moieties are stably connected. In some embodiments, linked is a covalent linkage. In some embodiments, linked is a peptide linkage. In some embodiments, linked is a reversible linkage. In some embodiments, linked is an irreversible linkage. In some embodiments, linked is an amino linkage. In some embodiments, linked is a thiol linkage. In some embodiments, linked is a serine linkage. In some embodiments, the linkage is linkage to a side chain of an amino acid.

In some embodiments, the linker comprises a cysteine. In some embodiments, the linker comprises at least one cysteine. In some embodiments, the first moiety is linked to the N-terminus of the linker and the cysteine is at the C-terminus of the linker. In some embodiments, the first moiety is linked to the C-terminus of the linker and the cysteine is at the N-terminus of the linker. In some embodiments, the linker comprising the cysteine comprises a histidine tag. In some embodiments, the histidine tag comprises a plurality of histidines. In some embodiments, the histidine tag comprises at least 1, 2, 3, 4, 5, 6, 7, 8, 9, or 10 histidines. Each possibility represents a separate embodiment of the invention. In some embodiments, the histidine tag comprises 6 histidines.

In some embodiments, a PEG molecule is attached to the cysteine. In some embodiments, the second moiety is attached to the cysteine. In some embodiments, the second moiety is attached to the cysteine via thiol linkage. In some embodiments, the second moiety comprises a thiol reactive group or a plurality of thiol reactive groups. In some embodiments, the second moiety comprises at least one thiol reactive group. Examples of thiol reactive groups include, but are not limited to, OPSS, maleimide, vinylsulfone and iodoacetamide functional groups. In some embodiments, the PEG molecule or molecules are attached to the cysteine via thiol linkage. In some embodiments, the PEG molecule or molecules comprise a thiol reactive group or a plurality of thiol reactive groups. In some embodiments, the PEG molecule or molecules comprises one thiol reactive group. In some embodiments, the thiol reactive groups are selected from OPSS, maleimide, vinylsulfone and iodoacetamide functional groups.

In some embodiments, the first moiety binding mCD28 is smaller than 100 kDa. In some embodiments, the first moiety binding mCD28 is smaller than 50 kDa. In some embodiments, the first moiety binding mCD28 is smaller than 25 kDa. In some embodiments, the first moiety binding mCD28 is smaller than 20 kDa. In some embodiments, the first moiety binding mCD28 is smaller than 15 kDa.

In some embodiments, the agent comprises a second moiety. In some embodiments, the second moiety is connected to the first moiety by a linker. In some embodiments, the second moiety comprises a shielding molecule. In some embodiments, the second moiety is a shielding moiety. In some embodiments, the second moiety is a protective moiety. In some embodiments, the second moiety protects the first moiety. In some embodiments, the second moiety shields the first moiety. In some embodiments, the second moiety increases stability of the first moiety. In some embodiments, increasing stability is increasing stability in a physiological fluid. In some embodiments, the physiological fluid is a biological fluid. In some embodiments, the bodily fluid is selected from the group consisting of: blood, serum, gastric fluid, intestinal fluid, saliva, bile, tumor fluid, breast milk, urine, interstitial fluid, and stool. In some embodiments, the biological fluid is blood. In some embodiments, blood is whole blood or serum. In some embodiments, blood is serum. In some embodiments, increasing stability in blood comprises reducing clearance from blood. In some embodiments, reducing clearance from blood is reducing clearance of the first moiety from blood. In some embodiments, reducing clearance from blood is reducing clearance of the agent from blood. In some embodiments, reducing clearance from blood comprises reducing renal filtration, reducing lysosomal degradation or both. In some embodiments, reducing clearance from blood comprises reducing renal filtration. In some embodiments, reducing clearance from blood comprises reducing lysosomal degradation. In some embodiments, increasing stability comprises increasing half-life of the first moiety. In some embodiments, increasing stability comprises decreasing degradation. In some embodiments, degradation comprises degradation by proteases. In some embodiments, degradation comprises decreasing degradation by a lysosome. In some embodiments, decreasing clearance comprises decreasing the proportion of the first moiety that is filtered by the renal system or the kidney glomerulus. In some embodiments, the second moiety increases stability of the first moiety, decreases clearance of the first moiety, decreases degradation of the first moiety or any combination thereof. Measuring stability of a protein in a subject is well characterized in the art, and any method may be performed. In some embodiments, measurements of molecule concentration in a fluid are made a various time points in order to calculate stability.

It will be understood by a skilled artisan that when the function of the second moiety is referred to as increasing, decreasing, enhancing, reducing or any comparative measure, the comparison is as compared to the first moiety alone. Comparison to the first moiety linked of the linker is also envisioned. In some embodiments, increase is at least a 5, 10, 15, 20, 25, 30 35, 40, 45, 50, 55, 60, 65, 70, 75, 80, 85, 90, 95, 100, 110, 120,125, 130, 140, 150, 175, 200, 250, 300, 350, 400, 450, 500, 600, 700, 800, 900 or 1000% increase. Each possibility represents a separate embodiment of the invention. In some embodiments, decrease is at least a 5, 10, 15, 20, 25, 30 35, 40, 45, 50, 55, 60, 65, 70, 75, 80, 85, 90, 95, 97, 99 or 100% decrease. Each possibility represents a separate embodiment of the invention.

In some embodiments, the second moiety comprises or consists of a serum or blood molecule. In some embodiments, the serum or blood molecule is a human molecule. In some embodiments, the molecule is a protein. In some embodiments, the protein can be bound by a receptor on a cell. In some embodiments, binding by the receptor enables uptake into the cell. In some embodiments, uptake enables release back into blood. In some embodiments, the protein is serum albumin. In some embodiments, the serum albumin is human serum albumin (HSA). In some embodiments, the second moiety comprises or consists of an HSA polypeptide. In some embodiments, HSA comprises the amino acid sequence DAHKSEVAHRFKDLGEENFKALVLIA-FAQYLQQCPFEDHVKLVNEVTEFAKTCVADE SAE-NCDKSLHTLFGDKLCTVATLRETYGEMADCCAKQ-EPERNECFLQHKDDNPNLPR LVRPEVDVMCTAFHD-NEETFLKKYLYEIARRHPYFYAPELLFFAKRYKAAF-TECCQAA DKAACLLPKLDELRDEGKASSAKQRLK-CASLQKFGERAFKAWAVARLSQRFPKAEFA EVSKL-VTDLTKVHTECCHGDLLECADDRADLAKYICENQD-SISSKLKECCEKPLLEKS HCIAEVENDEMPADLPS-LAADFVESKDVCKNYAEAKDVFLGMFLYEYAR-RHPDYSVV LLLRLAKTYETTLEKCCAAADPHEC-YAKVFDEFKPLVEEPQNLIKQNCELFEQLGEYK FQNALLVRYTKKVPQVSTPTLVEVSRNLGKVG-SKCCKHPEAKRMPCAEDYLSVVLNQ LCVLHEK-TPVSDRVTKCCTESLVNRRPCFSALEVDETYVPKEF-NAETFTFHADICTLSE KERQIKKQTALVELVKHKP-KATKEQLKAVMDDFAAFVEKCCKADDKETCFAE-EGKK LVAASQAALGL (SEQ ID NO: 65). In some embodiments, HSA consists of SEQ ID NO: 65.

In some embodiments, the second moiety comprises or consists of a molecule that binds a serum protein. In some embodiments, the second moiety comprises or consists of a polypeptide that binds a serum protein. In some embodiments, the second moiety comprises or consists of a lipid that binds a serum protein. In some embodiments, the second moiety comprises or consists of a polypeptide that binds a serum albumin. In some embodiments, the second moiety comprises or consists of a polypeptide that binds HSA. In some embodiments, the second moiety comprises or consists of a lipid that binds a serum albumin. In some embodiments, the second moiety comprises or consists of a lipid that binds HSA. In some embodiments, the lipid is a fatty acid or fatty acid derivative. In some embodiments, the second moiety comprises or consists of an HSA binding polypeptide. In some embodiments, the second moiety comprises or consists of an HSA binding lipid. In some embodiments, an HSA binding polypeptide is selected from an antibody, an antigen binding fragment of an antibody, a Fab fragment, a single chain antibody, a single domain antibody, a small molecule and a peptide that specifically binds to HSA. In some embodiments, the HSA binding polypeptide is a Fab fragment. In some embodiments, the HSA binding polypeptide is a single chain antibody. In some embodiments, the HSA binding polypeptide is a single domain antibody. In some embodiments, the HSA binding polypeptide is a peptide that specifically binds to HSA.

In some embodiments, the HSA binding polypeptide comprises a single domain antibody. In some embodiments, the HSA binding polypeptide is a single domain antibody. In some embodiments, the second moiety comprises a single domain antibody comprising or consisting of the sequence:

EVQLVESGGGLVQPGNSLRLSCAASGFTFSSFGMS-
WVRQAPGKGLEWVSSISGSGSDT LYADSVKGRFTIS-
RDNAKTTLYLQMNSLRPEDTAVYYCTIGGSLSRSS-
QGTLVTVSSAA A (SEQ ID NO: 19). In some embodi-
ments, the single domain antibody binding HSA is Alb8.

By another aspect, there is provided a nucleic acid mol-
ecule encoding the agent of the invention.

In some embodiments, the nucleic acid molecule is a
DNA molecule. In some embodiments, the nucleic acid
molecule is an RNA molecule. In some embodiments, the
nucleic acid molecule is introduced into a cell. In some
embodiments, the nucleic acid molecule is introduced into a
bacterial cell, a yeast cell, an insect cell, or a mammalian
cell. In some embodiments, the nucleic acid molecule is
introduced into a human cell. In some embodiments, the
nucleic acid molecule is provided on an expression vector.
In some embodiments, the expression vector comprises the
nucleic acid molecule encoding the agent of the invention.
In some embodiments, the expression vector is a mamma-
lian expression vector.

The term "nucleic acid" is well known in the art. A
"nucleic acid" as used herein will generally refer to a
molecule (i.e., a strand) of DNA, RNA or a derivative or
analog thereof, comprising a nucleobase. A nucleobase
includes, for example, a naturally occurring purine or
pyrimidine base found in DNA (e.g., an adenine "A," a
guanine "G," a thymine "T" or a cytosine "C") or RNA (e.g.,
an A, a G, an uracil "U" or a C). The terms "nucleic acid
molecule" include but not limited to single-stranded RNA
(ssRNA), double-stranded RNA (dsRNA), single-stranded
DNA (ssDNA), double-stranded DNA (dsDNA), small RNA
such as miRNA, siRNA and other short interfering nucleic
acids, snoRNAs, snRNAs, tRNA, piRNA, tnRNA, small
rRNA, hnRNA, circulating nucleic acids, fragments of
genomic DNA or RNA, degraded nucleic acids, ribozymes,
viral RNA or DNA, nucleic acids of infections origin,
amplification products, modified nucleic acids, plasmidical
or organellar nucleic acids and artificial nucleic acids such
as oligonucleotides.

In some embodiments, the nucleic acid molecule encodes
the first moiety of the agent. In some embodiments, the
nucleic acid molecule encodes the second moiety of the
agent. In some embodiments, the nucleic acid molecule
encodes both the first and the second moiety of the agent. In
some embodiments, the nucleic acid molecule encodes only
the first moiety of the agent. In some embodiments, coding
sequences for the first and the second moieties are located on
the same nucleic acid molecule. In some embodiments
coding sequences for the first and the second moieties are
located on separate nucleic acid molecules. In some embodi-
ments, the second moiety is not encoded by a nucleic acid.
In some embodiments, the nucleic acid molecule comprises
a nucleic acid sequence or a plurality of nucleic acid
sequences encoding the agent of the invention or a portion
thereof. In some embodiments, the expression vector com-
prises a nucleic acid molecule comprising one or more
coding sequences for the agent of the invention. In some
embodiments, the expression vector comprises the nucleic
acid molecule comprising the coding sequence for the first
moiety. In some embodiments, the expression vector com-
prises the nucleic acid molecule comprising the coding
sequence for the second moiety. In some embodiments, the
expression vector comprises the nucleic acid molecule com-
prising the coding sequence for the first and second moieties.
In some embodiments, the nucleic acid molecule comprises
the coding sequence for the first and second moieties, and
the coding sequences for the first and second moieties are in frame, thus encoding a fusion protein. In some embodi-
ments, the nucleic acid molecule comprises the coding
sequence for the first and second moieties separated by a
coding sequence for a linker and the coding sequences for
the first moiety, the linker, and the second moiety are in
frame, thus encoding a fusion protein. In some embodi-
ments, the expression vector comprises the nucleic acid
molecule comprising the coding sequence for the first and
second moieties in frame. In some embodiments, the expres-
sion vector comprises the nucleic acid molecule comprising
the coding sequence for the first and second moieties sepa-
rated by a coding sequence for a linker and the coding
sequences for the first moiety, the linker, and the second
moiety are in frame.

In some embodiments, the nucleic acid sequence encod-
ing the agent or a portion thereof is operably linked to a
promoter. The term "operably linked" is intended to mean
that the nucleotide sequence of interest is linked to the
regulatory element or elements in a manner that allows for
expression of the nucleotide sequence (e.g. in an in vitro
transcription/translation system or in a host cell when the
vector is introduced into the host cell).

Methods of Use

By another aspect, there is provided a method of treating
and/or preventing cancer in a subject in need thereof, the
method comprising administering the agent of the invention.

By another aspect, there is provided a method of improv-
ing immunotherapy in a subject in need thereof, the method
comprising administering the agent of the invention.

By another aspect, there is provided a method of decreas-
ing sCD28 in a subject in need thereof, the method com-
prising administering the agent of the invention.

In some embodiments, the immunotherapy is PD-1 and/or
PD-L1 based immunotherapy. In some embodiments, the
PD-1/PD-L1 based immunotherapy comprises administer-
ing an anti-PD1 or anti-PD-L1 antibody. In some embodi-
ments, the therapy comprises blockade of the PD-1 check-
point. In some embodiments, the immunotherapy comprises
administering allogenic, syngeneic or autologous immune
cells to the subject. In some embodiments, the immune cells
are T cells. In some embodiments, the subject in need of
immunotherapy suffers from cancer. In some embodiments,
the subject suffers from cancer. In some embodiments, the
cancer is a sCD28 positive cancer. In some embodiments,
the cancer is a sCD28 high cancer. In some embodiments,
the subject is at risk for developing cancer.

As used herein, the terms "treatment" or "treating" of a
disease, disorder, or condition encompasses alleviation of at
least one symptom thereof, a reduction in the severity
thereof, or inhibition of the progression thereof. Treatment
need not mean that the disease, disorder, or condition is
totally cured. To be an effective treatment, a useful compo-
sition herein needs only to reduce the severity of a disease,
disorder, or condition, reduce the severity of symptoms
associated therewith, or provide improvement to a patient or
subject's quality of life.

In some embodiments, the decreasing comprises admin-
istering to the subject at least one agent of the invention. As
used herein, the terms "administering," "administration,"
and like terms refer to any method which, in sound medical
practice, delivers a composition containing an active agent
to a subject in such a manner as to provide a therapeutic
effect. One aspect of the present subject matter provides for
oral administration of a therapeutically effective amount of
an agent of the invention to a patient in need thereof. Other suitable routes of administration can include parenteral, subcutaneous, intravenous, intramuscular, or intraperitoneal.

By another aspect, there is provided a pharmaceutical composition comprising an agent of the invention and a therapeutically acceptable carrier, adjuvant or excipient. In some embodiments, the administering is administering a pharmaceutical composition of the invention.

As used herein, the term "carrier," "excipient," or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, glycols, such as propylene glycol, polyols such as glycerin, sorbitol, mannitol and polyethylene glycol; esters such as ethyl oleate and ethyl laurate, pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, stearic acid, magnesium stearate, calcium sulfate, polyols, pyrogen-free water, isotonic saline, phosphate buffer solutions, as well as other non-toxic pharmaceutically compatible substances used in other pharmaceutical formulations. Wetting agents and lubricants such as sodium lauryl sulfate, as well excipients, stabilizers, antioxidants, and preservatives may also be present. Any non-toxic, inert, and effective carrier may be used to formulate the compositions contemplated herein.

The carrier may comprise, in total, from about 0.1% to about 99.99999% by weight of the pharmaceutical compositions presented herein.

In some embodiments, the methods of the invention do not degrade or lead to degradation of mCD28. In some embodiments, the methods of the invention do not decrease mCD28 levels on immune cells. In some embodiments, the methods of the invention do not decrease mCD28-mediated immune cell activation. In some embodiments, the methods of the invention maintain mCD28 levels on immune cells in the subject. In some embodiments, the methods of the invention increase mCD28 levels on immune cells in the subject.

In some embodiments, the reduction is at least a 10, 20, 30, 40, 50, 60, 70, 80, 90, 95, or 99% reduction in sCD28. Each possibility represents a separate embodiment of the invention. In some embodiments, the reduction is in serum sCD28. In some embodiments, the reduction is in the blood levels of sCD28. In some embodiments, the reduction is in the levels of sCD28 in the tumor microenvironment (TME).

In some embodiments, the subject's blood comprises elevated levels of sCD28. In some embodiments, the subject's blood before the decreasing comprises elevated levels of sCD28. In some embodiments, the levels are elevated above those of healthy subjects. In some embodiments, the subject's sCD28 levels are elevated by at least 5%, 10%, 15%, 20%, 25%, 30%, 40%, 50%, 60%, 70%, 80%, 90%, 100%, 150%, 200%, 250%, 300%, 350%, 400%, 500%, 600%, 700%, 800%, 900%, or 1000% above healthy subject levels. Each possibility represents a separate embodiment of the invention. In some embodiments, the levels are elevated above 5, 6, 7, 8, 9, 10, 12, 14, 15, 16, 18, 20, 25, 30, 35, 40, 45 or 50 ng/mL of blood. Each possibility represents a separate embodiment of the invention. In some embodiments, the levels are elevated above 5 ng/mL. In some embodiments, the levels are elevated above 10 ng/mL. In some embodiments, the levels are elevated above 20 ng/mL. In some embodiments, the subject's blood comprises at least 5, 6, 7, 8, 9, 10, 12, 14, 15, 16, 18, 20, 25, 30, 35, 40, 45 or 50 ng sCD28 per mL of blood. Each possibility represents a separate embodiment of the invention. In some embodiments, the subject's blood prior to the decreasing comprises at least 5, 6, 7, 8, 9, 10, 12, 14, 15, 16, 18, 20, 25, 30, 35, 40, 45 or 50 ng sCD28 per mL of blood. Each possibility represents a separate embodiment of the invention. In some embodiments, the subject's blood comprises at least 5 ng/mL sCD28. In some embodiments, the subject's blood comprises at least 10 ng/mL sCD28. In some embodiments, the subject's blood comprises at least 20 ng/mL sCD28. In some embodiments, the subject's blood prior to the decreasing comprises at least 5 ng/mL sCD28. In some embodiments, the subject's blood prior to the decreasing comprises at least 10 ng/mL sCD28. In some embodiments, the subject's blood prior to the decreasing comprises at least 20 ng/mL sCD28.

In some embodiments, the subject suffers from cancer. In some embodiments, the cancer is a cancer that can be treated with PD-1/PD-L1 therapy. In some embodiments, the subject has undergone PD-1/PD-L1 therapy. In some embodiments, the subject is a non-responder to PD-1/PD-L1 therapy. In some embodiments, the subject is naïve to PD-1/PD-L1 therapy. In some embodiments, the methods of the invention are performed together with PD-1/PD-L1 therapy. In some embodiments, the methods of the invention are performed before PD-1/PD-L1 therapy.

In some embodiments, the method further comprises administering another immunotherapy to the subject. In some embodiments, the method further comprises administering a PD-1 and/or PD-L1 based immunotherapy. In some embodiments, the another immunotherapy is a checkpoint inhibitor. In some embodiments, the checkpoint inhibitor is a PD-1 and/or PD-L1 inhibitor. In some embodiments, the checkpoint inhibitor is a CTLA-4 inhibitor. In some embodiments, the another immunotherapy is a chimeric antigen receptor (CAR) based immunotherapy. In some embodiments, the CAR is a CAR-T. In some embodiments, the CAR is a CAR-NK. In some embodiments, the another immunotherapy is a cancer vaccine.

As used herein, the terms "CAR-T cell" and "CAR-NK cell" refer to an engineered receptor which has specificity for at least one protein of interest (for example an immunogenic protein with increased expression following treatment with an epigenetic modifying agent) and is grafted onto an immune effector cell (a T cell or NK cell). In some embodiments, the CAR-T cell has the specificity of a monoclonal antibody grafted onto a T-cell. In some embodiments, the CAR-NK cell has the specificity of a monoclonal antibody grafted onto a NK-cell. In some embodiments, the T cell is selected from a cytotoxic T lymphocyte and a regulatory T cell.

CAR-T and CAR-NK cells and their vectors are well known in the art. Such cells target and are cytotoxic to the protein for which the receptor binds. In some embodiments, a CAR-T or CAR-NK cell targets at least one viral protein. In some embodiments, a CAR-T or CAR-NK cell targets a plurality of viral proteins. In some embodiments, a CAR-T or CAR-NK cell targets a viral protein with increased expression due to contact with an epigenetic modifying agent.

Construction of CAR-T cells is well known in the art. In one non-limiting example, a monoclonal antibody to a viral protein can be made and then a vector coding for the antibody will be constructed. The vector will also comprise a costimulatory signal region. In some embodiments, the costimulatory signal region comprises the intracellular domain of a known T cell or NK cell stimulatory molecule. In some embodiments, the intracellular domain is selected from at least one of the following: CD3Z, CD27, CD28, 4-1BB, OX40, CD30, CD40, PD-1, ICOS, lymphocyte function-associated antigen-1 (LFA-1), CD2, CD 7, LIGHT, NKG2C, B7-H3, and a ligand that specifically binds with CD83. In some embodiments, the vector also comprises a CD3Z signaling domain. This vector is then transfected, for example by lentiviral infection, into a T-cell.

In some embodiments, the cancer is a cancer with elevated sCD28 levels. In some embodiments, the cancer comprises high sCD28 levels. In some embodiments, elevated and/or high sCD28 levels are levels at and/or above 5, 6, 7, 8, 9, 10, 12, 14, 15, 17, 20, 25, 30, 35, 40, 50, 60, 70, 80, 90 or 100 ng/mL. Each possibility represents a separate embodiment of the invention. In some embodiments, the cancer comprises high sCD28 levels. In some embodiments, elevated and/or high sCD28 levels are levels at and/or above 5, 10, 15, 20, 25, 30, 35, 40, 45, 50, 55, 60, 65, 70, or 75% of the levels in a healthy subject. Each possibility represents a separate embodiment of the invention. In some embodiments, the cancer is not breast cancer. In some embodiments, the cancer is selected from melanoma, head and neck, non-small cell lung cancer, ovarian, kidney, gastric and colorectal. In some embodiments, the cancer is selected from melanoma, head and neck, non-small cell lung cancer, ovarian, and colorectal. In some embodiments, the cancer is melanoma, head and neck, non-small cell lung cancer, ovarian, kidney, gastric or colorectal. Each possibility represents a separate embodiment of the invention.

Kits

By another aspect, there is provided a kit comprising at least one agent of the invention, or the pharmaceutical composition of the invention.

In some embodiments, the kit further comprises a PD-1 and/or PD-L1 based immunotherapeutic. In some embodiments, the kit comprises a label stating the agent of the invention is for use with a PD-1 and/or PD-L1 based immunotherapeutic. In some embodiments, the kit comprises a label stating the PD-1 and/or PD-L1 based therapeutic is for use with an antibody or pharmaceutical composition of the invention.

By another aspect, there is provided a kit comprising a PD-1 and/or PD-L1 based immunotherapeutic comprising a label stating it is for use with an antibody or pharmaceutical composition of the invention.

In some embodiments, a kit of the invention is for use in treating cancer. In some embodiments, a kit of the invention is a diagnostic kit. In some embodiments, a kit of the invention is for use in determining serum levels of sCD28 in a subject in need thereof. In some embodiments, the subject suffers from cancer. In some embodiments, a kit of the invention is for use in determining suitability of a subject to be treated with an agent or pharmaceutical composition of the invention. In some embodiments, the kit is for use in determining suitability of a subject to be treated with anti-PD-1/PD-L1 based immunotherapy.

Methods of Agent Generation

By another aspect, there is provided a method of generating an agent of the invention comprising at least one of:
    a. obtaining a first moiety that binds mCD28 on a cell surface;

b. linking the first moiety to a second moiety that enhances protein stability by a linker to produce a linked agent and testing binding of the linked agent to mCD28 on a cell surface; and
    c. selecting a linked agent that binds mCD28 on a cell surface;
thereby generating an agent of the invention.

By another aspect, there is provided a method of generating an agent on the invention, comprising:
    culturing a host cell comprising one or more vectors comprising a nucleic acid sequence encoding an agent, wherein the nucleic acid sequence is that of an agent that was selected by:
        i. obtaining a first moiety that binds mCD28 on a cell surface;
        ii. linking the first moiety to a second moiety that enhances protein stability by a linker to produce a linked agent and testing binding of the linked agent to mCD28 on a cell surface; and
        iii. selecting a linked agent that binds mCD28 on a cell surface;
thereby generating an agent of the invention.

In some embodiments, linking comprises linking the first moiety to a linker. In some embodiments, linking comprises linking the second moiety to a linker. In some embodiments, the second moiety is linked to a linker attached the first moiety. In some embodiments, the first moiety is linked to the linker attached the second moiety. In some embodiments, linking comprises a chemical process of linkage. Methods of peptide linkage as well as chemical linkages are well known in the art and any such method may be employed.

In some embodiments, the method further comprises testing an ability of the agent to block cleavage by a protease of mCD28 on a cell surface. In some embodiments, the agent is an anti-cleavage agent. In some embodiments, the agent is an anti-shedding agent. In some embodiments, the agent decreases shedding of sCD28 in a subject. In some embodiments, the agent decreases cleavage of mCD28. In some embodiments, the agent decreases cleavage of mCD28 in a subject.

In some embodiments, the protease is MMP-2. In some embodiments, the protease is ADAM10. In some embodiments, the protease is ADAM17. In some embodiments, the protease is MMP-2, ADAM10, ADAM17 or a combination thereof.

As used herein, the term "extracellular domain of CD28" refers to the N-terminal portion of CD28 that comes before the transmembrane domain. In some embodiments, an extracellular domain of CD28 is sCD28. In some embodiments, an extracellular domain of CD28 is CD28a. In some embodiments, an extracellular domain of CD28 is the CD28 stalk domain. In some embodiments, an extracellular domain of CD28 comprises the stalk domain of CD28. In some embodiments, an extracellular domain of CD28 comprises or consists of the sequence NKILVKQSPMLVAYD-NAVNLSCKYSYNLFSREFRASLHKGLDSAVEVCV-VYGNYSQQ LQVYSKTGFNCDGKLGNESVTFYLQN-LYVNQTDIYFCKIEVMYPPPYLDNEKSNGTIIH VKGKHLCPSPLFPGPSKP (SEQ ID NO: 53). In some embodiments, the extracellular domain of CD28 or a fragment thereof is dimeric. In some embodiments, the extracellular domain of CD28 or a fragment thereof is monomeric. In some embodiments, the extracellular domain of CD28 or a fragment thereof is dimeric or monomeric.

As used herein, a "fragment" refers to a partial polypeptide that makes up part of the larger protein or protein domain. In some embodiments, a fragment comprises at least 10, 20, 30, 40 or 50 amino acids. Each possibility represents a separate embodiment of the invention. In some embodiments, a fragment comprises at most 10, 20, 30, 40, 50, 60 70, 80, 90 or 100 amino acids. Each possibility represents a separate embodiment of the invention. In some embodiments, obtaining an agent that binds a fragment of the extracellular domain of CD28 is obtaining an agent that binds specifically to a CD28 stalk domain.

In some embodiments, the method further comprises assaying mCD28 downstream signaling in the presence of the obtained agent and selecting at least one agent that neither substantially agonizes nor substantially antagonizes mCD28 signaling. In some embodiments, the selecting is selecting at least one agent that does not antagonize mCD28 signaling. It will be understood by a skilled artisan that for cancer treatment agonizing CD28 signaling might not be deleterious, but that antagonizing the signaling would be counterproductive.

In some embodiments, testing an agent's ability to block cleavage comprises measuring sCD28 in serum of activated immune cells in the presence and absence of the agent. In some embodiments, testing an agent's ability to block cleavage comprises mixing of the agent, the protease and an extracellular domain of CD28 or a fragment thereof comprising a cleavage site. In some embodiments, the testing further comprises sequencing the extracellular domain of CD28 or a fragment thereof to check for truncation and/or cleavage. In some embodiments, the testing further comprises running the extracellular domain of CD28 or a fragment thereof on a gel that is sufficiently sensitive to measure the size change due to cleavage. In some embodiments, the testing further comprises measuring the production of sCD28 from cells expressing mCD28 in the presence of the agent and the protease.

In some embodiments, the method further comprises assaying the linked agent's stability in blood. In some embodiments, the method further comprises selecting a linked agent with increased stability in blood. In some embodiments, assaying increased stability is as compared to the stability of the first moiety alone. In some embodiments, assaying increased stability is as compared to the stability of the first moiety linked to the linker. Methods of assaying protein stability are well known in the art and include the methods described herein. In some embodiments, the assaying comprises incubating the agent in blood or serum and measuring agent concentration at various time points. In some embodiments, the assaying comprises administering the agent to a model animal and measuring agent concentration in blood of the animal at various time points. In some embodiments, the model animal is a rodent. In some embodiments, the rodent is a mouse. Any method of assaying stability, half-life and/or blood retention known in the art may be employed.

In some embodiments, the obtaining an agent comprises immunizing a shark or camelid with said CD28 extracellular domain or fragment thereof and collecting antibodies from said immunized organism. In some embodiments, the obtaining an agent comprises screening a library of agents for binding to a CD28 extracellular domain or fragment thereof and selecting an agent that binds.

In some embodiments, the collecting an antibody comprises extracting B cells from a spleen of the immunized shark or camelid. In some embodiments, the B cells are fused with a melanoma cell to produce a hybridoma. In some embodiments, the antibodies are collected from the culture media of the hybridoma. In some embodiments, obtaining the agent comprises immunizing an organism with the CD28 extracellular domain or fragment thereof, and collecting antibodies from the immunized organism. In some embodiments, the organism is a mouse. In some embodiments, the organism is selected from a rabbit, a mouse, a rat, a shark, a camelid, a chicken, a goat and a phage. In some embodiments, the camelid is selected from a camel and a llama. In some embodiments, the collecting comprises drawing blood. In some embodiments, the collecting comprises:

a. extracting B cells from a spleen of the immunized organism;

b. fusing the extracted B cells with myeloma cells to produce a hybridoma; and c. collecting antibodies from the hybridoma.

In some embodiments, obtaining the agent comprises screening a library of agents for binding to a CD28 extracellular domain or fragment thereof and selecting an agent that so binds. In some embodiments, the library is a phage display library. In some embodiments, the library is an immunized library derived from splenic B cells. In some embodiments, the library is an IgG library. In some embodiments, the library is a Fab library. In some embodiments, the library is a library of VHH antibodies. In some embodiments, the library is a library of single chain, single domain or nanobodies. In some embodiments, obtaining the agent comprises sequencing the agent. In some embodiments, obtaining the agent comprises producing a recombinant form of the agent. In some embodiments, selecting the agent comprises sequencing the agent. In some embodiments, selecting the agent comprises producing a recombinant form of the agent. In some embodiments, the recombinant form is produced from the sequence of the agent. In some embodiments, the method further comprises humanizing the agent.

Expressing of a nucleic acid molecule that encodes an agent within a cell is well known to one skilled in the art. It can be carried out by, among many methods, transfection, viral infection, or direct alteration of the cell's genome. In some embodiments, the gene is in an expression vector such as plasmid or viral vector. One such example of an expression vector containing p16-Ink4a is the mammalian expression vector pCMV p16 INK4A available from Addgene.

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

By another aspect, there is provided an agent produced by a method of the invention.

By another aspect, there is provided a pharmaceutical composition comprising an agent produced by a method of the invention and a pharmaceutically acceptable carrier, excipient or adjuvant.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Antibodies—Commercial mouse monoclonal anti-CD28 clone #CD28.2 (Biolegend, Cat. No. 302902) and FITC conjugated (Biolegend, Cat. No. 302906). Goat polyclonal anti-CD28 (R&D system, Cat. No. AF-342-PB). FITC conjugated anti-Human PD-L1 (BD bioscience, Cat. No. 558065). APC conjugated anti-Human PD-L2 (Biolegend, Cat. No. 345508). PE conjugated anti-Human IDO (R&D system, Cat. No. IC6030P). Goat anti mouse IgG Alexa Fluor 647 (Biolegend, Cat. No. 405322). Donkey anti human IgG (H+L) Alexa Fluor 647 (Jackson immune research, Cat. No. 709-605-149). Goat anti mouse IgG HRP (Jackson immune research, Cat. No. 115-035-071). Anti-Human CD3 clone OKT3 (Biolegend, Cat. No. 317304). Anti-Human PD-1 pembrolizumab (MK-3475). Human IgG (Sigma, Cat. No. 14506).

Isolation of VHH targeting the stalk region of human CD28 receptor—The genetic code of peripheral blood B cells, derived from naïve non-immunized Llama, was used to construct a phage library composed of particles expressing individual VHHs as a fusion protein with a C-terminal His6-Myc tag. The naïve library was used to select nanobody with binding capabilities to the stalk region of human CD28. Screenings were done with biotinylated recombinant CD28-Fc chimera or oxidized dimeric peptide with the sequence of "HVKGKHLCPSPLFPGPSKP (SEQ ID NO: 52)" with a biotin addition at the C-terminal. Each antigen was bound to streptavidin magnetic beads that were blocked with skimmed milk. In-solution selections of phages were performed using the same antigen throughout three consecutive selection rounds, varying the phage input amount and antigen concentration. Blocked beads without antigen were used as control. Elution of bound phages was carried out with trypsin for 20 mins. Enrichment ratios during in-solution selections were calculated as the ratio between the number of phages eluted from the CD28 antigen selection conditions over the number of phage eluted from no antigen selection condition. 279 individual phage mono-clones of selected outputs, in either phage or periplasmic formats, were verified for antigen binding by ELISA and characterized for binding to membranal CD28 by flow cytometry. 72 clones showed specific binding to the stalk region peptide in periplasmic format, 22 proved to have a unique CDR sequence and only 6 were found to belong to a distinctive CDR3 family. The 6 VHHs were produced as recombinant proteins in CHO cells with c-terminal His tag and evaluated for anti-shedding activity and cellular binding. Transfection— CD28 wt (encoding the full-length CD28 transcript) plasmids were generated by cloning the DNA sequences into a PCDNA3.1 vector. Transfections were done using Jet Pei Transfection regent (PolyPlus Transfections). Stable transfectants were selected in G418-containing medium.

ELISA—Commercial ELISA kits were used for quantitation of the amount of human interferon-gamma (Biolegend, Cat. No. 430103), human interleukin 2 (Biolegend, Cat. No. 431802), human interleukin 6 (Biolegend, Cat. No. 430502), human interleukin 10 (Biolegend, Cat. No. 430603), human tumor growth factor beta 1 (Biolegend, Cat. No. 436708), human interleukin beta 1 (Biolegend, Cat. No. 437004) and human CD28 (R&D system, Cat. No. DY342). Cell Proliferation and viability (MTT assay) was conducted according to manufacturer instructions (Roche, Cat. No. 11465007001). Kynurenine (IDO activity) ELISA kit was conducted according to manufacturer instructions (ImmuSmol, Cat. No. BA E-2200).

CD28 stalk region binding assay—Biotin conjugated wild-type or L145K CD28 stalk region dimeric peptides were immobilized on neutravidin coated ELISA maxi-sorb plates. Serial dilution of the VHH clones (0.2-5 µg/mL) was performed and detection of bound VHH was done with anti His tag-HRP conjugated antibody and development was done with TMB.

Cytokine multiplex—The simultaneous evaluation of several cytokines was carried out using ProcartaPLex (Invitrogen, Cat. No. PPX-07-MXXGPY2) on the Magpix system (Millipore).

Flow Cytometry—Generally, cells were kept on ice during all steps. Prior to staining, $5 \times 10^5$ cells were blocked with 50 µg/mL human IgG (Sigma, Cat. No. 14506) in FACS buffer (PBS with 0.1% BSA) for 15 min. Anti-CD28 VHH constructs were used at indicated concentrations. When Alb-8 constructs were used the mixtures was supplemented with recombinant human serum albumin (Sigma, Cat. No. A9731) to saturate Alb-8. Antibodies were used at concentrations recommended by the manufacturer and incubated for 30 min. in the dark. Incubations were done in a volume of 100 µL in 96-well U bottom plates. Cells were washed twice with 200 µL of FACS buffer and transferred to FACS tubes in 150 µL of FACS buffer for analysis. Cells were analyzed on a Gallios Flow Cytometer (Beckman Coulter) using the Kaluza for Gallios Flow Cytometry Acquisition Software.

Cell lines and isolation of human immune cells—Jurkat leukemic T-cell lymphoblast cell line clone E6.1 and SCC-25 tongue squamous cell carcinoma were obtained from the ATCC. PBMCs were isolated from fresh blood samples of healthy donors using standard lymphocytes separation medium (MBP, Cat. No. 850494). CD3 cells were isolated from fresh blood samples of healthy donors using RosetteSEP™ Human T cells Enrichment Kit (STEMCELL, Cat. No. 15061) by negative selection method. CD4 cells were isolated from fresh blood samples of healthy donors using EasySep™ Human CD4 T cells Enrichment Kit (STEMCELL, Cat. No. 19059) by negative selection method. Monocytes were isolated from fresh blood samples of healthy donors using EasySep™ Human Monocyte Enrichment Kit (STEMCELL, Cat. No. 17952) by negative selection method. All cells were grown in complete RPMI-1640 media supplemented with 10% HI-FCS and pen/strep mixture.

CD86 blocking FACS—$0.5 \times 10^6$ HEK293 cells stably transfected with human CD28 were incubated with 2 µg/ml CD86-Fc (R&D systems, Cat. No. 141-B2) without or with anti CD28-shedding nanobodies at indicated concentrations for 30 min in room temperature. Cells were washed and taken for secondary binding using anti-human heavy and light chains antibody conjugated to fluorophore at 1:5000 dilution for 20 min on ice. When Alb-8 constructs were used the mixtures were supplemented with recombinant human serum albumin (Sigma, Cat. No. A9731) to saturate Alb-8.

Transfection— CD28-FL (encoding the full-length CD28 transcript), CD80-FL (encoding the full-length CD80 transcript) and scOKT3-CD14 (encoding the single-chain FV portion of mouse anti-CD3 OKT3 clone fused to CD14 extra-cellular domain) plasmids were generated by cloning the DNA sequences into a PCDNA3.1 vector. Transfections were done using Jet Pei Transfection regent (PolyPlus Transfections). Stable transfectants were selected in G418 and/or hygromycin-containing medium.

Dendritic cell differentiation—monocytes were cultured at a density of $1 \times 10^6$/mL in RPMI medium with growth factors that was refreshed at day 3 and at day 6. Immature dendritic cells (iDCs) were induced by 50 ng/mL GM-CSF (R&D systems, Cat. No. 215-GM) and 20 ng/mL IL-4 (R&D systems, Cat. No. 204-IL) for 6 days. When needed the iDCs were further differentiated into mature dendritic cells by addition of 100 ng/mL LPS (Sigma, Cat. No. L4391) and 20 ng/mL interferon-gamma (R&D systems, Cat. No. 285-IF) for 48 hrs. The generated cell populations were tested for the indicated phenotypes by FACS analysis of relevant markers and by analysis of secretion of characteristic cytokines.

Metalloproteinases—Commercial recombinant human metalloproteinase MMP-2 was used both from Anaspec (Cat. No. AS-72005) or R&D system (Cat. No. 902-MP). Commercial recombinant human metalloproteinase MMP-13 was purchased from R&D system (Cat. No. 511-MM). Pro-MMP2 and Pro-MMP-13 were activated with 1 mM p-aminophenylmercuric acetate (APMA) for 1-2 hr at 37° C. according to manufacturer's protocol.

Synthetic Peptide—Substrate peptide with the final form of "DYKDDDDKGGGGGHVKGKHLCPSPLFPGPSKP (SEQ ID NO: 54)-biotin" was designed to include the amino acid sequence of human CD28 stalk region (His134-Pro152) between an N-terminal cMyc tag followed by five glycine sequence and a C-terminal biotin conjugation. The peptide was custom synthesized by Genecust Europe. The Cysteine residue at position 141 was used to generate a dimeric peptide by a disulfide linkage. CD28 stalk region peptide with mutation at the cleavage site, substitution of Leucine at position 145 to Lysine, was similarly synthesized with the final form of "DYKDDDDKGGGGGHVKGKHLCP-SPKFPGPSKP (SEQ ID NO: 55)-biotin".

In-vitro cleavage assay— 50 ng pf purified recombinant MMP-2 or MMP-13 were incubated with 0.125 µM dimeric c-Myc-tagged and biotinylated substrate peptide in the presence or absence of MMP inhibitor (TMI-1, 50 nM), M9 Fab or indicated VHH clones at various concentrations (0.4-10 µg/mL) for 5 hours. The assay was performed in 50 mM Tris, 10 mM $CaCl_2$), 150 mM NaCl, 0.05% Brij-35, pH 7.5. After 5 hr the cleavage reaction mixture was diluted to a final 1 nM concentration of peptide and loaded on a neutravidin plate to bind the peptide. After 1 hr incubation at room-temperature the plate was washed, and detection of un-cleaved peptide is done using an anti-cMyc antibody conjugated to HRP.

SEB or CMV activation of PBMCs for the generation of soluble CD28-$0.3 \times 10^6$ PBMCs were stimulated with 0.5 ng/mL SEB (Sigma, Cat. No. S4881) for 5-7 days at 37° C. with/without the indicated concentration of various protease inhibitors in 48 well plate. Alternatively, $0.1 \times 10^6$ PBMCs were stimulated with 0.5 ng/mL SEB in 96 well plate format assay. For CMV stimulation $0.5 \times 10^6$ PBMCs were stimulated with 0.5 µg/mL CMV peptivator (Milteny Biotec, Cat.

No. 130-093-435) for 2-5 days at 37° C. with/without the indicated concentration of various protease inhibitors in a 96 well plate. For continuous shedding experiments PBMC were stimulated with SEB or CMV in 24 well plate for 24 hr, cells were taken and washed three times with RPMI without stimulant and plated again in a 96 well plate. Samples were taken at indicated times and put under freezing conditions until examination for soluble CD28.

PHA activation of T cells for the generation of soluble CD28-2×10$^5$ CD3 or CD4 T cells were incubated with concentration of 5 µg/mL Phytohemagglutinin (Sigma, Cat. No. L8902), 200 IU of IL-2 (Proleukine) and indicated treatments for 7 days. When Alb-8 constructs were used the mixtures were supplemented with recombinant human serum albumin (Sigma, Cat. No. A9731) to saturate Alb-8.

Protease Inhibitors—Protease inhibitors were added at the indicated concentration at the start of each experiment. In cellular week-long assays another portion of the inhibitors was added after 3 days at the final concentration. Protease inhibitors used are GI254023X (Sigma, Cat. No. SML0789) or TMI-1 (Sigma, Cat. No. PZ0336).

Cellular assays evaluating anti shedding activity of VHH—For SEB activation of PBMCs, 0.1×10$^6$ PBMCs were stimulated with 2 ng/mL SEB (Sigma, Cat. No. S4881) for 5-7 days at 37° C. with/without the indicated concentrations of various treatments in 96 well plates. For PHA activated T cells, 0.1×10$^6$ CD4 T cells were incubated with the indicated concentration of Phytohemagglutinin (Sigma, Cat. No. L8902) and 200 IU/mL of IL-2 (Proleukine) for 5-7 days at 37° C. with/without the indicated concentrations of various treatments in 96 well plates. For HEK spontaneous CD28 shedding assay, 0.1×10$^5$ HEK cells were incubated for 48 hours at 37° C. with/without the indicated concentrations of various treatments in 96 well plates.

Mixed lymphocyte reaction— 0.1×10$^6$ T cells were mixed with 0.2×10$^4$ mature dendritic cells from different donor for 24-72 hr at 37° C. with/without the indicated concentration of treatments. Assays were conducted in complete RPMI-1640 media supplemented with 10% HI-human serum and pen/strep mixture.

Autologous monocytes CD3 MLR—0.5×10$^6$ T cells were mixed with 0.5×10$^5$ monocytes from same CMV reactive donor and stimulated with 0.5 µg/mL CMV peptivator for 6 days at 37° C. with/without the indicated concentration of treatments.

Antibody sequencing—Antibodies were supplied to the Rapid Novor company for amino acid sequencing. Sequencing was performed using standard methods, which briefly include LC-MS analysis performed after enzymatic digestion with six enzymes (pepsin, trypsin, chymotrypsin, elastase, Lys C and Asp N). Digestion was performed with disulfide reduction, and alkylation. LC-MS/MS analysis was performed using a Thermo-Fisher Q-exactive mass spectrometer. In both the heavy and light chains of each antibody 100% of amino acid residues were covered by at least 5 peptide scans, with significant supporting fragment ions. CDRs were determined using Chothia scheme.

Production of recombinant 2A1 constructs—Synthetic codon-optimized genes were subcloned into relevant pcDNA3.1 expression vectors. 2A1 constructs were produced from transiently transfected ExpiCHO cells and purified by immobilized metal affinity chromatography (IMAC). Protein preparations in 1×PBS pH 7.4 were analyzed by SDS-PAGE for the presence of correct chains under nonreducing conditions and by analytical size exclusion chromatography (aSEC) for the quantification of monomeric form within the preparation.

Chemical modification of parental 2A1 molecule—2A1 construct carrying the C-terminal Cysteine (2A1-1C) was incubated with different chemical moieties such as linear mPEG 20 kDa-OPSS (Nanocs, Cat. No. PG1-OS-20K), linear mPEG 40 kDa-Mal (Sigma Aldrich, Cat. No. JKA3123), (BroadPharm, Cat. No. BP-22151). In some cases, Tris (2-carboxyethyl) phosphine hydrochloride (TCEP) (Sigma Aldrich, Cat. No. 75259) was added prior to the reaction to resolve dimeric content. Following the completion of the different modification reactions, the reaction mixtures were loaded on SP cation exchange column to remove excess reagents and, in some cases, un-reacted material. The preparations were PBS desalted using Vivaspin concentrators and analyzed by mass-spectrometry for conjugation validation. In other preparations, HSA (Sigma, Cat. No, A9731) was modified with MAL-PEG(2000 Da)-MAL (Nanocs, Cat. No. PG2-ML-2K) and purified from remains of un-reacted reagent by anion exchange column, following incubation with 2A1-1C to yield the final product HSA-P2K-2A1.

Direct CD28 EIA—Unless discussed otherwise, Corning high binding plate or equivalent were used for screening. Each well was coated with 200 ng of human CD28-Fc chimera (R&D, Cat. No. 342-CD). Plates were blocked using 1% casein in PBS for 1 hr. at room temperature (RT). Plates were washed 3 times using PBST and incubated with investigated antibody following detection with mouse anti His conjugated with HRP (Biolegend, Cat. No. 652504) diluted 1:5000 or Rabbit anti Camelid VHH Cocktail conjugated with HRP (GenScript, Cat. No. A02016) diluted 1:500. When Alb-8 constructs were used the mixtures were supplemented with recombinant human serum albumin (Sigma, Cat. No. A9731) to saturate Alb-8.

T cells stimulation with OKT3—0.1×10$^6$ isolated CD3 T cells (from healthy donors) were stimulated with indicated amount of anti-CD3 clone OKT3 for 24-48 hr at 37° C. When stated recombinant human CD80-Fc (2 µg/ml, R&D system, Cat. No. 141-B1) was added in soluble form. Treatments of antibodies or VHH targeting CD28 or controls were added at the indicated concentration in soluble form.

T cells stimulation with A375/scOKT3 artificial antigen presenting cells (aAPC)—1×10$^5$ isolated CD3 T cells (from healthy donors) were stimulated with 0.4×10$^4$ mitomycin treated aAPC (A375 cells stably transfected with scOKT3-CD14 chimera plasmid) for 24 hr at 37° C. Treatments of antibodies or VHH targeting CD28 or controls were added at the indicated concentration in soluble form. Assays were conducted in complete RPMI-1640 media supplemented with 10% HI-human serum and pen/strep mixture.

T cells stimulation with HEK/CD80/scOKT3 artificial antigen presenting cells (aAPC-CD80)—1×10$^5$ isolated CD3 T cells (from healthy donors) were stimulated with 0.5×10$^4$ mitomycin treated aAPC-CD80 (HEK293 cells stably transfected with CD80 and scOKT3-CD14 chimera plasmids) for 24-48 hr at 37° C. Treatments of antibodies or VHH targeting CD28 or controls were added at the indicated concentration in soluble form. Assays were conducted in complete RPMI-1640 media supplemented with 10% HI-human serum and pen/strep mixture.

Pharmaco-kinetics profile study—A PK study for each test article was performed in a group of 12 adult male mice (male balb/c). Each test article was given a dose equivalent to 2.5-10 mg/Kg by intravenous injection. Blood samples were taken from 3 animals at the following time points: 0.083 (animals 1-3), 1 (animals 4-6), 2 (animals 7-9), 8 (animals 10-5 12), 24 (animals 1-3), 48 (animals 3-6), 72 (animals 7-9), 96 (animals 10-12) and 168 (all animals)

hours. The concentration of test articles was done in the K-EDTA collected blood. Quantification of the concentration of each test article was done by using sandwich ELISA composed of a pair from following antibodies: Rabbit anti Camelid VHH (QVQ, Cat. No. QE-19), Rabbit anti Camelid VHH conjugated with HRP (GenScript, Cat. No. A01861), Goat anti human serum albumin conjugated with HRP (Abcam, Cat. No. ab19183) as described in Table 1:

TABLE 1

| | | | | | | | |
|---|---|---|---|---|---|---|---|
| | | | ∏ Sandwich ELISA components | | | | |
| VHH#2A1 constructs | 2A1-6H | 2A1-15GS-HSA | 2A1-15GS-Alb8 | 2A1-L40KPEG | 2A1-Hel20-HSA | 2A1-1C-P2K-HSA | 2A1-R20KPEG |
| Capture antibody | Rabbit anti VHH 4 µg/mL | Rabbit anti VHH 4 µg/mL | Rabbit anti VHH 4 µg/mL | Rabbit anti VHH 4 µg/mL | Rabbit anti VHH 4 µg/mL | Rabbit anti VHH 4 µg/mL | Rabbit anti VHH 4 µg/mL |
| Detection antibody | Rabbit anti-VHH-HRP 1 µg/mL | Anti-human HSA-HRP 0.5 µg/mL | Rabbit anti-VHH-HRP 1 µg/mL | Rabbit anti-VHH-HRP 2 µg/mL | Anti-human HSA-HRP 0.5 µg/mL | Anti-human HSA-HRP 0.5 µg/mL | Rabbit anti-VHH-HRP 2 µg/mL |
| STD range | 40 ng/mL-0.62 ng/mL 2 fold | 30 ng/mL-0.04 ng/mL 3 fold | 30 ng/mL-0.04 ng/mL 3 fold | 300 ng/mL 0.41 ng/mL 3 fold | 30 ng/mL-0.04 ng/mL 3 fold | 30 ng/mL-0.04 ng/mL 3 fold | 300 ng/mL-0.41 ng/mL 3 fold |
| LOD | 1 ng/mL | 0.125 ng/mL | 0.125 ng/mL | 2.5 ng/mL | 0.5 ng/mL | 0.5 ng/mL | 5 ng/mL |

Example 1: Characterization of Anti-Shedding Antibody-Based Agents

The finding that human CD28 undergoes a proteolytic process by a matrix metalloproteinase (MMP) prompted the inspection of its polypeptide sequence for candidate regions showing potential susceptibility for proteolytic shedding. The most attractive sequence region in human CD28 is the stalk section, ranging from Histidine 134 to Proline 152 (SEQ ID NO: 52, HVKGKHLCPSPLFPGPSKP), connecting the globular IgV domain to the transmembrane region. This region holds 3 total leucine and valine residues, as well as a phenylalanine residue and is predicted to be devoid of any secondary structure elements that might hinder access of the proteases. Notably, the stalk region also contains Cysteine 141 that forms the inter-disulfide bond that facilitates the homo-dimerization of CD28. With the aim of generating an antibody or antibody fragments that specifically bind the CD28 stalk region and potentially block access of different proteases to shed CD28 while avoiding any compromising of CD28 oligomeric structure and function, CD1 mice were immunized with a dimeric peptide mimicking the CD28 stalk region. The peptide sequence used for immunization was SEQ ID NO: 56, GKHLCPSPLFPGPSKPK, the C-terminal Lysine was added in order to have a free amino group to allow KLH or BSA conjugation using hydrazide chemistry. The conjugations were performed between the hydrazide-terminated CD28 peptide and S-4FB modified BSA, which generates free aldehydes for site-specific conjugation. Dimerization was confirmed by running the peptide on a non-denaturing gel.

Figure 1A:
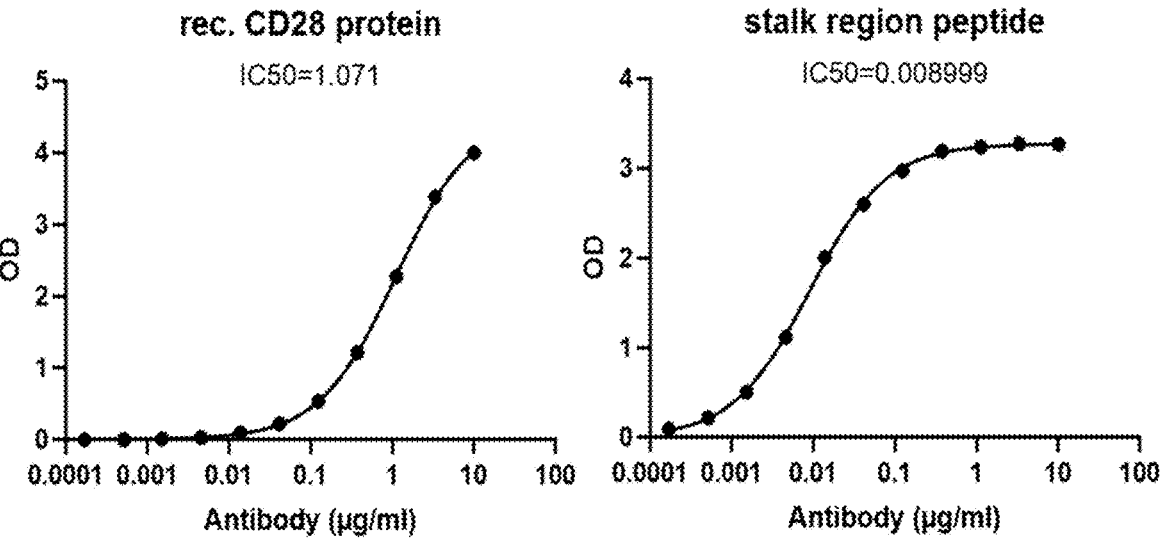
Figure 1B:
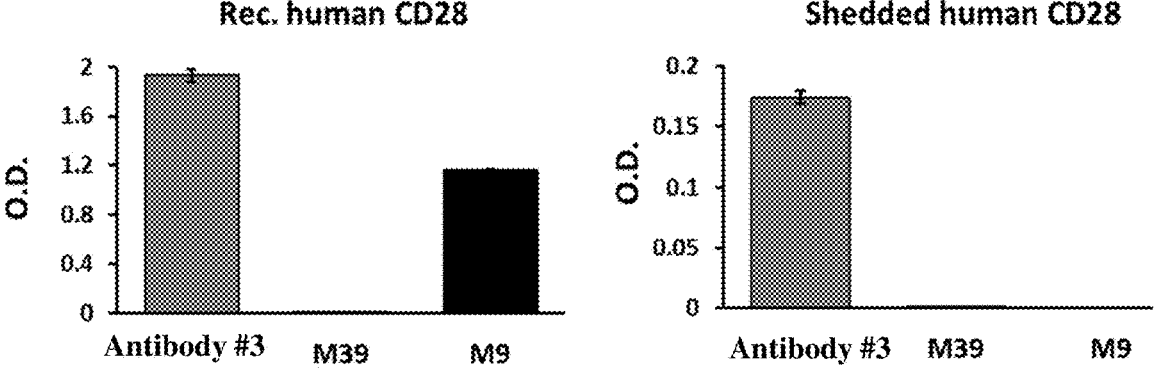

An antibody with high binding affinity for recombinant human CD28 as measured by direct CD28 EIA was found. This antibody is designated M9 and sequences of this antibody are provided hereinabove. Serial dilution of antibody M9 was used to confirm its specific binding to recombinant human sCD28 and to the stalk region peptide (FIG. 1A). Interestingly, while the antibody was able to detect recombinant human sCD28 it was not able to detect sCD28 actually shed from immune cells (FIG. 1B). This strongly suggests that the antibody binds at the cleavage site, and the deisotope to which it binds is incomplete in the cleaved form.

Figure 1C:
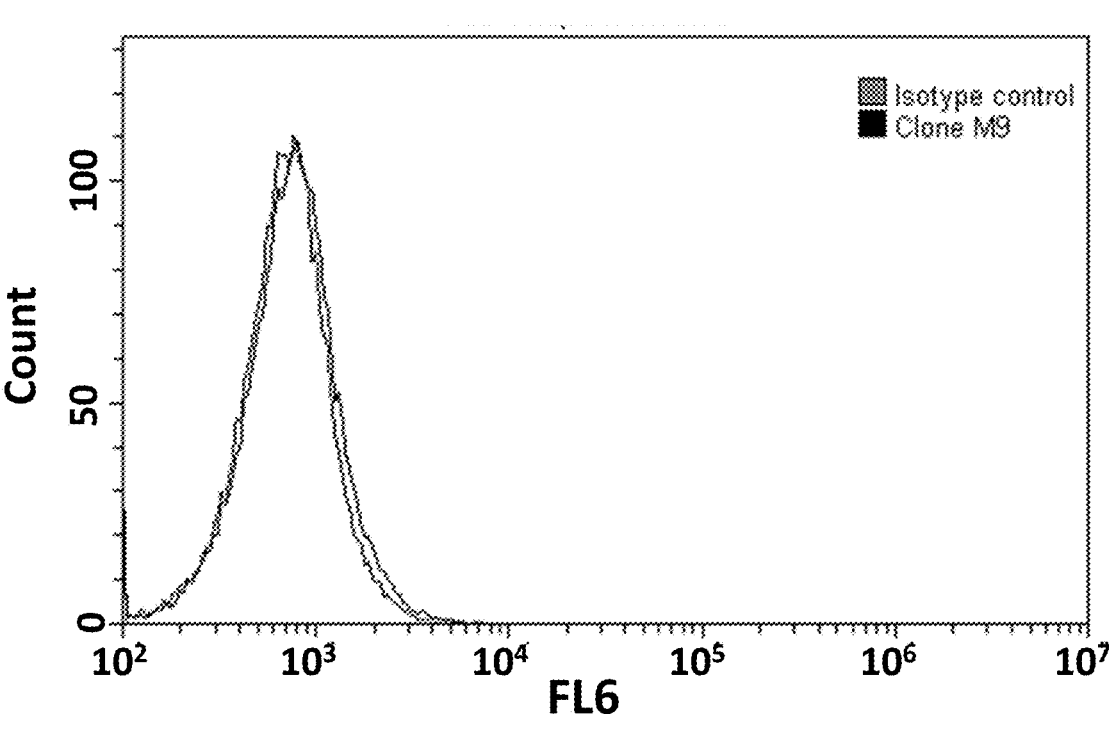
Figure 1C:
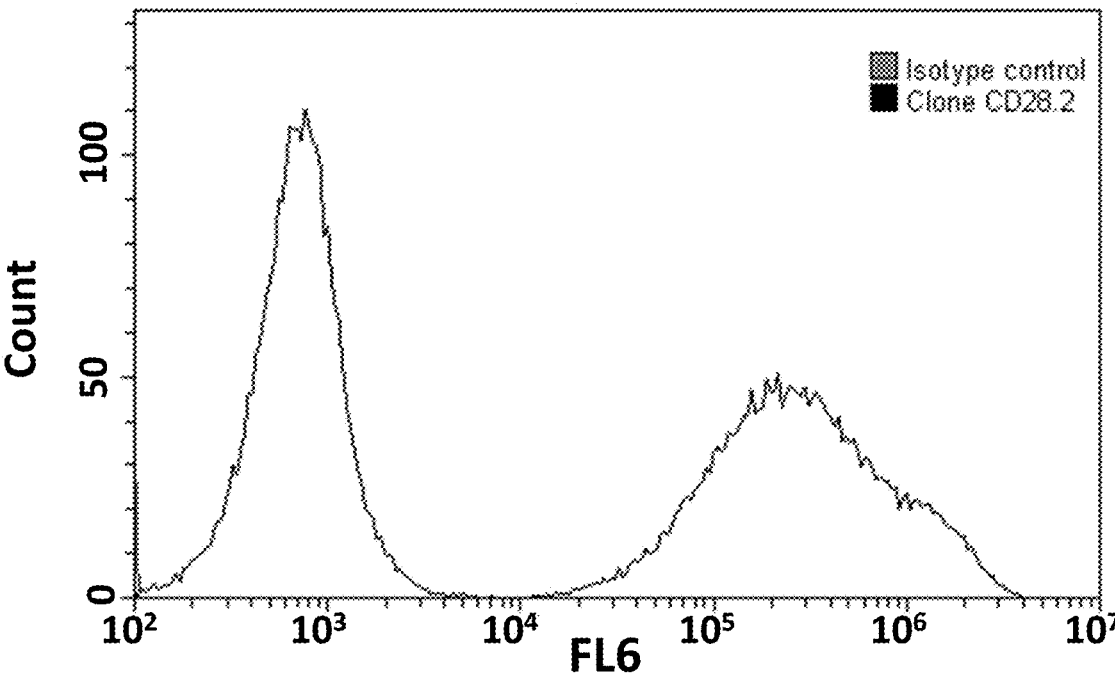

Next the ability of the antibody to bind mCD28 on a cell surface was investigated. In order to reduce shedding of sCD28 from a cell the antibody would need to actually bind on the membranal form of the protein and not just recombinant protein in solution. HEK293 cells overexpressing human full-length CD28 were analyzed. Mouse CD28 does not appear to be cleaved into a soluble form (activated murine splenocytes do not appear to produce sCD28) and so the human protein must be investigated. Cells were analyzed by flow cytometry using the M9 antibody and the CD28.2 antibody as a positive control. Surprisingly, M9 did not appear to bind to surface mCD28 (FIG. 1C). This is likely due to steric hinderance and limited access to the stalk region when it is membrane adjacent.

Example 2: Single-Domain Antibodies Inhibit sCD28 Shedding from the Cell Surface Small agents capable of binding mCD28 on the surface of a cell and blocking shedding of sCD28 were designed. While full size antibodies are about 150 kDa in size, Fab fragments derived from antibodies have a size of about 50 kDa, while single chain antibodies (also called single chain variable fragments, scFvs) have a size of about 25 kDa and single domain antibodies (also called VHH antibodies and DARPins) have a size of only 12-20 kDa.

Single domain antibodies were isolated using a phage library of naïve llama derived VHH. The library was composed of VHH sequences that were taken from naïve non-immunized Llama, i.e., extracting B cells and sequencing the whole available repertoire of VHH CDRs. These CDRs were implemented into phage to generate a library. Using ELISA and flow cytometry, the library was screened against recombinant CD28 extracellular domain and the dimeric stalk region peptide to find antibodies that specifically bind the stalk region of human CD28. The VHH sequences found to specifically bind the stalk region of human CD28 are: EVQLVESGGGLVQAGESLRLSCAASGSIASINAM-GWYRQAPGSQRELVAAISGGGDTY YADSVKGRFTIS-RDNAKTTVYLQMNSLRPEDTAVYYCVVDLYGSD-YWDWGQGTQVT VSSAAAHREIHHH (SEQ ID NO: 33, clone 2A1); EVQLVESGGGLVQAGGSLRLS-CAASGSLFSINAMAWYRQAPGKQRELVAAITSSGSTN YANSVKGRFTVSRDNAKNTMYLQMNSLKPED-TAVYYCVVDEYGSDYWIWGQGTQV TVSSAAAH-HHHMH (SEQ ID NO: 34, clone 4A4); and QVQLVES-GGGLVQAGGSLRLSCAASGSIFSINAMGWYRQAPG-KQRERVAAITSGGSTN YADSVKGRFTISRDNAKN-TVYLQMNNLEPRDAGVYYCVVDLYGEDYWIWGQ-GTQVT VSSAAAHHHHHH (SEQ ID NO: 35, clone 4A1).

The VHHs were produced as recombinant proteins in CHO cells and then evaluated for cellular binding and anti-shedding activity as described below. A His-tag at the C-terminus was used for purification and was linked via triple alanine repeat. The CDRs of the three investigated clones are provided in Table 2.

TABLE 2

| CDR sequences of the tested clones | | | |
|---|---|---|---|
| VHH Clone | CDR1 (SEQ ID) | CDR2 (SEQ ID) | CDR3 (SEQ ID) |
| 2A1 | INAMG (1) | AISGGGDTYYADSVKG (2) | DLYGSDYWD (3) |
| 4A4 | INAMA (4) | AITSSGSTNYANSVKG (5) | DEYGSDYWI (6) |
| 4A1 | INAMG (1) | AITSGGSTNYADSVKG (7) | DLYGEDYWI (8) |

Binding of the VHH clones to the human CD28 stalk region sequence was first confirmed with ELISA using serial dilution of VHH clones (FIG. 2). Binding to membranal human CD28 on the cellular level was confirmed with FACS analysis using labeled VHH clone and HEK cells overexpressing CD28 (FIG. 3). Membranal CD28 binding demonstrates access to the CD28 membrane proximal region. Previous experimentation has shown that the size of the agent is critical to access this region, as full-size antibodies that could bind to the CD28 stalk region peptides could not bind to the CD28 stalk region on cells (FIG. 1C). Notably, VHH clones were not capable of binding human CD28 stalk region sequence with a L-K substitution at amino acid residue 145, located within a potential MMP cleavage site (FIG. 4).

Anti-shedding activity was confirmed both on the peptide and the cellular level. ELISA techniques were used to detect intact human CD28 stalk region dimeric peptide to confirm that the VHH clones block the cleavage of human CD28 stalk region by MMP-2 (FIG. 5), and MMP-13 (FIG. 6) While M9 Fab exhibited the ability to block CD28 stalk region peptide cleavage, as described above it could not bind the CD28 stalk region on cells and could not inhibit CD28 shedding from cell membranes. On the cellular level, standard sandwich ELISA was used to confirm the efficacy of the VHH clones in inhibiting sCD28 shedding by measuring the levels of human sCD28 in the supernatant of HEK cells overexpressing human CD28 (FIG. 7), isolated CD4 T cells activated by PHA and IL-2 (FIG. 8) and PBMC activated by a superantigen (FIG. 9). As expected, M9 Fab did not decrease sCD28 levels in supernatant, further emphasizing the importance of size and architecture of the blocking agent on its ability to actually block shedding.

Critically, the VHH clones were found to not impair human CD28 functionality. Using flow-cytometry, it was found that the VHH clones do not change the magnitude of CD86 binding to membrane CD28 (FIG. 10). Standard sandwich ELISA was used to show the VHH clones do not agonize CD28 as measured by the secreted levels of the inflammatory cytokine interferon gamma (FIG. 11). Activating antibody CD28.2 was used as a positive control. Similarly, standard sandwich ELISA was used to show that the VHH clones do not antagonize CD80-Fc stimulation through CD28, as measured by the secreted levels of the cytokine IL-2 (FIG. 12).

Example 3: Designing Other Small Agents to Inhibit sCD28 Shedding from the Cell Surface Fab fragment generation is performed using a commercial kit, or commercially available service. The CDR regions of antibody M9 are used for Fab generation as they have been shown to bind to the proper deisotope. Efficacy of the resultant Fab fragment is tested first by binding assays to recombinant human CD28 and the dimeric stalk region peptide to confirm that this binding is retained. Binding to surface mCD28 is assayed by FACS to mouse cells expressing human CD28 and to human immune cells. Antibody CD28.2 is used as a positive control. Direct inhibition of sCD28 shedding is tested in immune cell culture after stimulation. sCD28 in the culture media is measured by sandwich ELISA when the cells are in the presence and absence of the Fab fragments. Fab fragments with shedding inhibitory action are assayed for their effect on CD28 signaling. First, agonism is tested by assaying the ability of the Fab fragments to induce secretion of a proinflammatory cytokine, e.g. interferon gamma, from T cells. Second, the ability to block binding of CD80-Fc (an agonist) is used to test antagonistic properties of the Fab fragments.

Single chain antibody generation using the M9 CDRs is performed by standard methods using a commercial service, or by inserting the CDRs into a scFv backbone. Purification is performed and the resultant antibodies are assessed by the same assays as described for Fab fragments.

Example 4: Generation of Serum Stable Agents Inhibiting CD28 Shedding from Cell Surface Though the VHH molecules were effective cleavage blockers, their small size leaves them at risk for degradation and clearance from serum if administered to a subject. In order to enhance the serum half-life of the VHH molecules they were linked to a second moiety that increases their size and enhances their stability. VHH 2A1 was selected for all conjugation tests as it was found to be the most potent cleavage blocker. Eleven distinct molecules were generated and tested; these molecules are summarized in Table 3. The sequences of these molecules are provided in Table 4. Due to the requirement for the agent to bind to the stalk region of CD28 on cells, the length and nature of the linker connecting the VHH to the half-life extending moiety is of crucial importance. A too short linker would render the second moiety to be close to the CD28-binding moiety, possibly interfering with its binding of membranal CD28. A too long linker might yield an agent in which the second moiety is too free to move around in relation to the first moiety, again possibly interfering with its CD28 binding activity.

First, human serum albumin (HSA) was employed as the half-life extending molecule. Human serum albumin (HSA), the most abundant protein in human serum, is known for its long half-life caused by its size (66 KDa) and ability to bind neonatal Fc receptor (FcRn) enabling its uptake by cells and its release back into the circulation. VHH 2A1 was conjugated at its C-terminus to HSA via flexible peptide linkers containing a GGGGS repeat. 1, 3, and 7 repeats were examined (2A1-5GS-HSA, 2A1-15GS-HSA, and 2A1-35GS-HSA respectively) to determine the optimal size of the linker that still allows access of the VHH to the cleavage site. A rigid, helical linker of 20 or 30 amino acids in length was also tested (2A1-20Hel-HSA and 2A1-30Hel-HSA, respectively).

The second tested half-life extending molecule was Alb8, a VHH clone that is specific to HSA. HSA-binding peptides, such as the Alb8 VHH (Maria, J. W. D. et al., Mol Cancer Ther. 2012, 11, 1017-1025) are known to enhance half-life when used in protein conjugates. Alb8 was also conjugated via flexible peptide linkers containing 1, 3 or 7 GGGGS repeats (2A1-5GS-Alb8, 2A1-15GS-Alb8, and 2A1-35GS-Alb8 respectively).

Next, PEGylation was tested as a half-life extending moiety. Addition of polyethylene glycol (PEG) to proteins has been extensively utilized to increase the protein size and thus extending half-life. For the purpose of attaching PEG molecules to the cleavage blocking VHH, a free cysteine group at the C-terminal of the VHH was added, exploiting the fact that camelid derived, and especially llama derived, single domain antibodies, lack free cysteine residues and even, for the most part, disulfide bonds. This cysteine, with its free thiol group, located far from the CDRs of the binding agent, can be utilized for attaching various PEG molecules carrying a thiol-reactive group, including maleimide and iodoacetate functional groups. The generated agents can comprise linear or branched PEG molecules, ranging in size from 500 Da to 40 KDa. A too small PEG may not enable half-life extension while a too large PEG may sterically interfere with the binding to CD28. PEG molecules can also be attached in additional positions besides at the C-terminal cysteine, such as at lysine or carboxylic acids (Glutamic and Aspartic residues).

To facilitate PEGylation, the dipeptide GC was added to the C-terminus of the 2A1 VHH. This C-terminal cysteine was either directly conjugated with a linear 40 KDa PEG moiety substituted with a maleimide thiol reactive functional group (2A1-1C-L40K) or was chemically conjugated to linear 20 KDa PEG moiety substituted with an SPDP functional group (2A1-1C-R20K). The SPDP group contains a pyridyldithiol moiety that forms a disulfide bond with the C-terminal cysteine of the VHH. Finally, a combined approach was tried in which the 2A1 VHH was linked to HSA by a GC dipeptide and the HSA was modified by PEGylation with a 2 KDa PEG moiety. To facilitate this, HSA was pre-modified on its single free thiol (at cysteine 34) with a bis-Maleimide-PEG (linear 2 KDa PEG) and then the exposed maleimide group reacts with the C-terminal cysteine of the VHH. While the disulfide both is a reversible and easily cleaved linkage, the binding of the maleimide group is irreversible and highly stable.

The agent is a fusion protein. The fusion protein includes a 6× histidine tag for the purposes of protein purification and recognition by a suitable binding antibody. Techniques for histidine tag-based purification are well known in the art.

TABLE 3

Summary of produced 2A1 half-life extending constructs

| Construct | Mw (KDa) | Half-life extending module | Linker | SEQ ID NO: |
|---|---|---|---|---|
| 2A1-6H | 13.57 | None | None | 33 |
| 2A1-5GS-HSA | 80.55 | Human serum albumin (25-609) | 5 amino acid flexible | 57 |
| 2A1-15GS-HSA | 81.18 | Human serum albumin (25-609) | 15 amino acid flexible | 58 |
| 2A1-35GS-HSA | 82.44 | Human serum albumin (25-609) | 35 amino acid flexible | 59 |
| 2A1-5GS-Alb-8 | 26.19 | VHH clone Alb-8 specific for albumin | 5 amino acid flexible | 60 |
| 2A1-15GS-Alb-8 | 26.82 | VHH clone Alb-8 specific for albumin | 15 amino acid flexible | 61 |
| 2A1-35GS-Alb-8 | 28.08 | VHH clone Alb-8 specific for albumin | 35 amino acid flexible | 62 |
| 2A1-20Hel-HSA | 81.1 | Human serum albumin (25-609) | 20 amino acid rigid helix | 63 |
| 2A1-30Hel-HSA | 82.1 | Human serum albumin (25-609) | 30 amino acid rigid helix | 64 |
| 2A1-1C-P2K-HSA | 79.5 | Human serum albumin (25-609) | 2K PEG at specific site | 65 |
| 2A1-1C-L40K | 53.78 | Linear 40 kDa PEG | 1 cysteine residue | 36 |
| 2A1-1C-R20K | 33.78 | Disulfide mediated linear 20 kDa PEG | 1 cysteine residue | 36 |

TABLE 4

Sequences of constructs

| Construct | Sequence (SEQ ID NO:) |
|---|---|
| 2A1-6H | EVQLVESGGGLVQAGESLRLSCAASGSIASINAMGWYRQAPGSQRE LVAAISGGGDTYYADSVKGRFTISRDNAKTTVYLQMNSLRPEDTAV YYCVVDLYGSDYWDWGQGTQVTVSSAHHHHHH (33) |
| 2A1-5GS-HSA | EVQLVESGGGLVQAGESLRLSCAASGSIASINAMGWYRQAPGSQRE LVAAISGGGDTYYADSVKGRFTISRDNAKTTVYLQMNSLRPEDTAV YYCVVDLYGSDYWDWGQGTQVTVSSAAAGGGGSDAHKSEVAHRF KDLGEENFKALVLIAFAQYLQQCPFEDHVKLVNEVTEFAKTCVADE SAENCDKSLHTLFGDKLCTVATLRETYGEMADCCAKQEPERNECFL QHKDDNPNLPRLVRPEVDVMCTAFHDNEETFLKKYLYEIARRHPYF YAPELLFFAKRYKAAFTECCQAADKAACLLPKLDELRDEGKASSAK QRLKCASLQKFGERAFKAWAVARLSQRFPKAEFAEVSKLVTDLTKV HTECCHGDLLECADDRADLAKYICENQDSISSKLKECCEKPLLEKSH CIAEVENDEMPADLPSLAADFVESKDVCKNYAEAKDVFLGMFLYEY ARRHPDYSVVLLLRLAKTYETTLEKCCAAADPHECYAKVFDEFKPL VEEPQNLIKQNCELFEQLGEYKFQNALLVRYTKKVPQVSTPTLVEVS RNLGKVGSKCCKHPEAKRMPCAEDYLSVVLNQLCVLHEKTPVSDR VTKCCTESLVNRRPCFSALEVDETYVPKEFNAETFTFHADICTLSEKE RQIKKQTALVELVKHKPKATKEQLKAVMDDFAAFVEKCCKADDKE TCFAEEGKKLVAASQAALGLHHHHHH (57) |
| 2A1-15GS-HSA | EVQLVESGGGLVQAGESLRLSCAASGSIASINAMGWYRQAPGSQRE LVAAISGGGDTYYADSVKGRFTISRDNAKTTVYLQMNSLRPEDTAV YYCVVDLYGSDYWDWGQGTQVTVSSAAAGGGGSGGGGSGGGGSD AHKSEVAHRFKDLGEENFKALVLIAFAQYLQQCPFEDHVKLVNEVT EFAKTCVADESAENCDKSLHTLFGDKLCTVATLRETYGEMADCCAK |

TABLE 4-continued

Sequences of constructs

Construct Sequence (SEQ ID NO:)

QEPERNECFLQHKDDNPNLPRLVRPEVDVMCTAFHDNEETFLKKYL
YEIARRHPYFYAPELLFFAKRYKAAFTECCQAADKAACLLPKLDELR
DEGKASSAKQRLKCASLQKFGERAFKAWAVARLSQRFPKAEFAEVS
KLVTDLTKVHTECCHGDLLECADDRADLAKYICENQDSISSKLKECC
EKPLLEKSHCIAEVENDEMPADLPSLAADFVESKDVCKNYAEAKDV
FLGMFLYEYARRHPDYSVVLLLRLAKTYETTLEKCCAAADPHECYA
KVFDEFKPLVEEPQNLIKQNCELFEQLGEYKFQNALLVRYTKKVPQV
STPTLVEVSRNLGKVGSKCCKHPEAKRMPCAEDYLSVVLNQLCVLH
EKTPVSDRVTKCCTESLVNRRPCFSALEVDETYVPKEFNAETFTFHA
DICTLSEKERQIKKQTALVELVKHKPKATKEQLKAVMDDFAAFVEK
CCKADDKETCFAEEGKKLVAASQAALGLHHHHHH (58)

2A1-     EVQLVESGGGLVQAGESLRLSCAASGSIASINAMGWYRQAPGSQRE
35GS-    LVAAISGGGDTYYADSVKGRFTISRDNAKTTVYLQMNSLRPEDTAV
HSA      YYCVVDLYGSDYWDWGQGTQVTVSSAAAGGGGSGGGGSGGGGSG
         GGGSGGGGSGGGGSGGGGSDAHKSEVAHRFKDLGEENFKALVLIAF
         AQYLQQCPFEDHVKLVNEVTEFAKTCVADESAENCDKSLHTLFGDK
         LCTVATLRETYGEMADCCAKQEPERNECFLQHKDDNPNLPRLVRPE
         VDVMCTAFHDNEETFLKKYLYEIARRHPYFYAPELLFFAKRYKAAF
         TECCQAADKAACLLPKLDELRDEGKASSAKQRLKCASLQKFGERAF
         KAWAVARLSQRFPKAEFAEVSKLVTDLTKVHTECCHGDLLECADD
         RADLAKYICENQDSISSKLKECCEKPLLEKSHCIAEVENDEMPADLPS
         LAADFVESKDVCKNYAEAKDVFLGMFLYEYARRHPDYSVVLLLRL
         AKTYETTLEKCCAAADPHECYAKVFDEFKPLVEEPQNLIKQNCELFE
         QLGEYKFQNALLVRYTKKVPQVSTPTLVEVSRNLGKVGSKCCKHPE
         AKRMPCAEDYLSVVLNQLCVLHEKTPVSDRVTKCCTESLVNRRPCF
         SALEVDETYVPKEFNAETFTFHADICTLSEKERQIKKQTALVELVKH
         KPKATKEQLKAVMDDFAAFVEKCCKADDKETCFAEEGKKLVAASQ
         AALGLHHHHHH (59)

2A1-5GS- EVQLVESGGGLVQAGESLRLSCAASGSIASINAMGWYRQAPGSQRE
Alb-8    LVAAISGGGDTYYADSVKGRFTISRDNAKTTVYLQMNSLRPEDTAV
         YYCVVDLYGSDYWDWGQGTQVTVSSAAAGGGGSEVQLVESGGGL
         VQPGNSLRLSCAASGFTFSSFGMSWVRQAPGKGLEWVSSISGSGSDT
         LYADSVKGRFTISRDNAKTTLYLQMNSLRPEDTAVYYCTIGGSLSRS
         SQGTLVTVSSAAAHHHHHH (60)

2A1-     EVQLVESGGGLVQAGESLRLSCAASGSIASINAMGWYRQAPGSQRE
15GS-Alb- LVAAISGGGDTYYADSVKGRFTISRDNAKTTVYLQMNSLRPEDTAV
8        YYCVVDLYGSDYWDWGQGTQVTVSSAAAGGGGSGGGGSGGGGSE
         VQLVESGGGLVQPGNSLRLSCAASGFTFSSFGMSWVRQAPGKGLEW
         VSSISGSGSDTLYADSVKGRFTISRDNAKTTLYLQMNSLRPEDTAVY
         YCTIGGSLSRSSQGTLVTVSSAAAHHHHHH (61)

2A1-     EVQLVESGGGLVQAGESLRLSCAASGSIASINAMGWYRQAPGSQRE
35GS-Alb- LVAAISGGGDTYYADSVKGRFTISRDNAKTTVYLQMNSLRPEDTAV
8        YYCVVDLYGSDYWDWGQGTQVTVSSAAAGGGGSGGGGSGGGGSG
         GGGSGGGGSGGGGSGGGGSEVQLVESGGGLVQPGNSLRLSCAASGF
         TFSSFGMSWVRQAPGKGLEWVSSISGSGSDTLYADSVKGRFTISRDN
         AKTTLYLQMNSLRPEDTAVYYCTIGGSLSRSSQGTLVTVSSAAAHHH
         HHH (62)

2A1-     EVQLVESGGGLVQAGESLRLSCAASGSIASINAMGWYRQAPGSQRE
20Hel-   LVAAISGGGDTYYADSVKGRFTISRDNAKTTVYLQMNSLRPEDTAV
HSA      YYCVVDLYGSDYWDWGQGTQVTVSSAAASAEAAAKEAAAKEAAA
         KAAAGSDAHKSEVAHRFKDLGEENFKALVLIAFAQYLQQCPFEDHV
         KLVNEVTEFAKTCVADESAENCDKSLHTLFGDKLCTVATLRETYGE
         MADCCAKQEPERNECFLQHKDDNPNLPRLVRPEVDVMCTAFHDNE
         ETFLKKYLYEIARRHPYFYAPELLFFAKRYKAAFTECCQAADKAACL
         LPKLDELRDEGKASSAKQRLKCASLQKFGERAFKAWAVARLSQRFP
         KAEFAEVSKLVTDLTKVHTECCHGDLLECADDRADLAKYICENQDS
         ISSKLKECCEKPLLEKSHCIAEVENDEMPADLPSLAADFVESKDVCK
         NYAEAKDVFLGMFLYEYARRHPDYSVVLLLRLAKTYETTLEKCCAA
         ADPHECYAKVFDEFKPLVEEPQNLIKQNCELFEQLGEYKFQNALLVR
         YTKKVPQVSTPTLVEVSRNLGKVGSKCCKHPEAKRMPCAEDYLSVV
         LNQLCVLHEKTPVSDRVTKCCTESLVNRRPCFSALEVDETYVPKEFN
         AETFTFHADICTLSEKERQIKKQTALVELVKHKPKATKEQLKAVMD
         DFAAFVEKCCKADDKETCFAEEGKKLVAASQAALGL (63)

2A1-     EVQLVESGGGLVQAGESLRLSCAASGSIASINAMGWYRQAPGSQRE
30Hel-   LVAAISGGGDTYYADSVKGRFTISRDNAKTTVYLQMNSLRPEDTAV
HSA      YYCVVDLYGSDYWDWGQGTQVTVSSAAASAEAAAKEAAAKEAAA
         KEAAAKEAAAKAAAGSDAHKSEVAHRFKDLGEENFKALVLIAFAQ
         YLQQCPFEDHVKLVNEVTEFAKTCVADESAENCDKSLHTLFGDKLC
         TVATLRETYGEMADCCAKQEPERNECFLQHKDDNPNLPRLVRPEVD
         VMCTAFHDNEETFLKKYLYEIARRHPYFYAPELLFFAKRYKAAFTEC

TABLE 4-continued

Sequences of constructs

| Construct | Sequence (SEQ ID NO:) |
|---|---|
| | CQAADKAACLLPKLDELRDEGKASSAKQRLKCASLQKFGERAFKA WAVARLSQRFPKAEFAEVSKLVTDLTKVHTECCHGDLLECADDRA DLAKYICENQDSISSKLKECCEKPLLEKSHCIAEVENDEMPADLPSLA ADFVESKDVCKNYAEAKDVFLGMFLYEYARRHPDYSVVLLLRLAK TYETTLEKCCAAADPHECYAKVFDEFKPLVEEPQNLIKQNCELFEQL GEYKFQNALLVRYTKKVPQVSTPTLVEVSRNLGKVGSKCCKHPEAK RMPCAEDYLSVVLNQLCVLHEKTPVSDRVTKCCTESLVNRRPCFSA LEVDETYVPKEFNAETFTFHADICTLSEKERQIKKQTALVELVKHKP KATKEQLKAVMDDFAAFVEKCCKADDKETCFAEEGKKLVAASQAA LGL (64) |
| 2A1-1C-P2K-HSA | EVQLVESGGGLVQAGESLRLSCAASGSIASINAMGWYRQAPGSQRE LVAAISGGGDTYYADSVKGRFTISRDNAKTTVYLQMNSLRPEDTAV YYCVVDLYGSDYWDWGQGTQVTVSSAAAHHHHHHGC (36) -2 KDa PEG-DAHKSEVAHRFKDLGEENFKALVLIAFAQYLQQCPFEDHVKLVNEV TEFAKTCVADESAENCDKSLHTLFGDKLCTVATLRETYGEMADCCA KQEPERNECFLQHKDDNPNLPRLVRPEVDVMCTAFHDNEETFLKKY LYEIARRHPYFYAPELLFFAKRYKAAFTECCQAADKAACLLPKLDEL RDEGKASSAKQRLKCASLQKFGERAFKAWAVARLSQRFPKAEFAEV SKLVTDLTKVHTECCHGDLLECADDRADLAKYICENQDSISSKLKEC CEKPLLEKSHCIAEVENDEMPADLPSLAADFVESKDVCKNYAEAKD VFLGMFLYEYARRHPDYSVVLLLRLAKTYETTLEKCCAAADPHECY AKVFDEFKPLVEEPQNLIKQNCELFEQLGEYKFQNALLVRYTKKVPQ VSTPTLVEVSRNLGKVGSKCCKHPEAKRMPCAEDYLSVVLNQLCVL HEKTPVSDRVTKCCTESLVNRRPCFSALEVDETYVPKEFNAETFTFH ADICTLSEKERQIKKQTALVELVKHKPKATKEQLKAVMDDFAAFVE KCCKADDKETCFAEEGKKLVAASQAALGL (65) |
| 2A1-1C-L40K | EVQLVESGGGLVQAGESLRLSCAASGSIASINAMGWYRQAPGSQRE LVAAISGGGDTYYADSVKGRFTISRDNAKTTVYLQMNSLRPEDTAV YYCVVDLYGSDYWDWGQGTQVTVSSAAAHHHHHHGC (36)- 40 KDa PEG |
| 2A1-1C-R20K | EVQLVESGGGLVQAGESLRLSCAASGSIASINAMGWYRQAPGSQRE LVAAISGGGDTYYADSVKGRFTISRDNAKTTVYLQMNSLRPEDTAV YYCVVDLYGSDYWDWGQGTQVTVSSAAAHHHHHHGC (36) -linear 20 KDa PEG |

Example 5: Functional Binding of CD28 Peptide

The above-described agents were evaluated for their ability to bind recombinant CD28 peptide. Recombinant human CD28-Fc chimeric protein, which contains the stalk region sequence, and exists as a dimer, was immobilized on ELISA maxi-sorb plates. A 3-fold dilution series of parental 2A1 and the eleven half-life extending 2A1 constructs was performed and detection of bound VHH was carried out using anti VHH-HRP conjugated antibody followed by development with TMB (FIG. 13). EC50 values for each construct were calculated using Graph-Pad software utilizing four-parameters non-linear regression curve and are summarized in Table 5. Based on this analysis, all of the generated 2A1 constructs retained their ability to bind CD28 recombinant peptide. It should be noted that as the VHH is very small there can often be interference with the binding of the anti-VHH antibody to the VHH. This may explain some of the variability in the EC50 values, though the data shows that all of the VHHs are functional binders. This interference is most keenly observed when the VHH binds membranal CD28 on the cell surface. As the stalk is directly adjacent to the plasma membrane the VHH epitope bound by the anti-VHH antibody becomes buried. Thus, VHH binding to cell surface CD28 must be measured indirectly by its effect on blocking cleavage (or other functional outcomes) and not in a direct binding assay.

TABLE 5

| EC50 values for parental 2A1 and the half-life extending constructs | |
|---|---|
| Construct | EC50 (nM) |
| 2A1 | 79.2 |
| 2A1-5GS-HSA | 102.67 |
| 2A1-15GS-HSA | 49.5 |
| 2A1-35GS-HSA | 45.8 |
| 2A1-5GS-Alb8 | 137 |
| 2A1-15GS-Alb8 | 171.7 |
| 2A1-35GS-Alb8 | 55.8 |
| 2A1-20Hel-HSA | 28.6 |
| 2A1-30Hel-HSA | 9.4 |
| 2A1-1C-P2K-HSA | N.D. |
| 2A1-1C-R20K | N.D. |
| 2A1-1C-L40K | 245.5 |

Example 6: Testing Blocking of CD86 Binding by the Half-Life Extending Constructs The above-described agents were evaluated for potential unwanted blocking of native ligand binding to membranal CD28 in the presence of the agents of the invention. CD28's natural ligand is CD86, and this binding induces immune activation. It has been demonstrated that the VHH itself does not impair CD86 binding to CD28, however, it is possible that the half-life extending moiety might block or interfere with the CD28 binding region or otherwise effect ligand binding. A construct that impairs CD86 binding is of little value as the molecule is intended to upregulate/enhance immune response.

HEK293 cells were made to over express human CD28 and were then monitored by flow-cytometry for CD86-Fc (2 μg/mL) binding using secondary anti human Fc antibody conjugated to AlexaFlour® 647. Binding was tested without any anti-CD28 molecules, with the parental VHH and with the 11 half-life extending constructs. VHH #10E9 which is a CD28 antagonist served as a positive control (upper right chart.) For isotype control an irrelevant VHH, clone #3C04, was used. None of the tested half-life extending constructs were found to significantly impair CD86 binding (FIG. 14). The percent of CD86 blocking was calculated as percent of signal (median) reduction for each construct from basal CD86-Fc binding without the presence of a treatment and is summarized in Table 6. The half-life extending constructs were generally found to be comparable to the parental VHH, and none of the molecules blocked CD86 binding at levels higher than the isotype control.

TABLE 6

| Percent blocking of CD86 | |
| --- | --- |
| Construct | Blocking CD86 binding (%) |
| Isotype | 14.5 |
| VHH#10E09 | 88.3 |
| 2A1-6H | 8.2 |
| 2A1-5GS-HSA | 14.5 |
| 2A1-15GS-HSA | 5.9 |
| 2A1-35GS-HSA | 6.7 |
| 2A1-5GS-Alb-8 | 0.0 |
| 2A1-15GS-Alb-8 | 0.8 |
| 2A1-35GS-Alb-8 | 2.4 |
| 2A1-20Hel-HSA | 11.2 |
| 2A1-30Hel-HSA | 0.0 |
| 2A1-1C-2K-HSA | 9.4 |
| 2A1-1C-R20K | 15.9 |
| 2A1-1C-L40K | 13.4 |

Example 7: Testing Agonistic Effect of the Half-Life Extending Constructs

The above-described agents were evaluated for a potential unwanted agonistic effect on membranal CD28. If the construct is generally agonistic it may generate a non-specific effect of generalized immune activation which would be detrimental. Agonistic effect was tested as follows. Isolated human CD3 positive T cells were stimulated for 24 hr with plate bound anti-CD3 (OKT3, 2 μg/mL, light grey bar) (FIG. 15A) or with A375 cells transfected with scOKT3 plasmid (FIG. 15B). This was done in the presence of an irrelevant VHH clone #3C04, a positive control anti-CD28 agonist antibody clone 28.2 or the various different 2A1 constructs. The concentration of secreted IL-2 in the supernatant was measured by standardized sandwich ELISA (Biolegend) and acted as a readout for CD28 stimulation (an agonistic effect). None of the tested 2A1 constructs produced an agonistic effect.

Example 8: Testing Antagonistic Effect of the Half-Life Extending Constructs The above-described agents were evaluated for a potential unwanted antagonistic effect on membranal CD28. As the molecules are meant to enhance the possibility of natural immune activation an antagonistic effect would be undesirable. Isolated human CD3 positive T cells were stimulated for 24 hours with HEK293 cells transfected with both human CD80 and scOKT3 plasmids (artificial APC-CD80, light grey bars). This was done in the presence of an irrelevant VHH clone #3C04 as a negative, isotype control, anti-CD28 antagonist clone VHH #12B07 as a positive control and the various 2A1 half-life extending constructs (FIG. 16). As before, IL-2 secretion was quantified with a standardized sandwich ELISA (Biolegend) as a measure of immune activation and CD28 antagonism. Similar to the results for agonism and ligand blocking, none of the half-life extending constructs were found to antagonize CD28.

Example 9: Testing Immunomodulatory Effect of the Half-Life Extending Constructs The above-described agents were evaluated for any general immunomodulatory effect in a physiological setting. A mixed-lymphocyte reaction was performed as described hereinabove. Specifically, isolated mature dendritic cells were incubated with allogeneic CD3 positive T cells for 24 hours. This was done in the presence of a control VHH (clone #3C04, isotype) and an antagonistic VHH clone (#1A07) as well as parental 2A1 VHH and the various half-life extending constructs at various concentrations. Once again IL-2 secretion was used as the readout. Surprisingly, the parental VHH produced a very minor unwanted inhibitory effect at the very highest concentration tested (FIG. 17). This inhibitory effect was abrogated in the various half-life extended molecules and indeed none of these molecules showed an immunomodulatory effect in this assay (FIG. 17).

Example 10: Testing Half-Life Extension by the Half-Life Extending Moieties

Having determined that all of the above-described agents do not produce an undesired activating or inhibiting effect, their ability to actually extend the half-life of the 2A1 VHH was tested. Balb/C mice were administered via intravenous injection a fixed dose per mouse of 100 μg of each VHH molecule (2A1-1C-P2K-HSA was administered at 50 μg/mouse). This was performed in triplicate and serum concentrations were measured at various time points up to 168 hours (FIG. 18). The half-life (T1/2) of each molecule was estimated according to the terminal point measured and is presented in Table 7. As can be seen, all of the half-life extending molecules were functional and did indeed enhance the half-life of the VHH. The 2A1-1C-R20K which comprises a disulfide bond between the VHH and the PEGylated peptide produced only a modest improvement in half-life likely due to cleavage of the bond in the serum. Still this construct increased the half-life by a factor of 8. All the other constructs were highly effective, although as can be seen in Table 7 some were more effective than others. The relative half-life can be summarized as 2A1-15GS-Alb8>2A1-1C-L40K>2A1-15GS-HSA>2A1-20HEL-HSA>2A1-1C-P2K-HSA>>2A1-1C-R20K>>2A1.

TABLE 7

| []Half-life of the various 2A1 VHH constructs | | | |
| --- | --- | --- | --- |
| Construct | 2A1-6H | 2A1-15GS-HSA | 2A1-15GS-Alb-8 | 2A1-20Hel-HSA |
| $T_{1/2}$ (hr) | 0.3 | 23.0 | 32.5 | 19.0 |

| Construct | 2A1-1C-R20K | 2A1-1C-L40K | 2A1-1C-P2K-HSA |
| --- | --- | --- | --- |
| $T_{1/2}$ (hr) | 2.4 | 23.9 | 15.8 |

Example 11: Testing Inhibition of sCD28 Shedding by the Half-Life Extending Constructs Having determined that all the above-described half-life extending molecules do, to one extent or another, extend half-life, their ability to block shedding of sCD28 from cells was now tested. It is essential that the addition of a half-life extension domain or group does not hamper this basic ability or at least does not hamper it at too great a level such that the VHH cannot longer function. To this end, levels of soluble CD28 were measured in culture media of isolated human CD4 stimulated with PHA and IL-2 or in PBMCs stimulated with SEB. Inhibition of CD28 shedding was calculated as percent of soluble CD28 reduction from basal stimulation. Tests were run in triplicate and at various concentrations for some of the constructs. MMP inhibitor was used as a positive control and the irrelevant VHH #3C04 was used as a negative control (Isotype Control). The level of soluble human CD28 in the supernatant was quantified by standardized sandwich ELISA (R&D Systems). As can be seen in FIG. 19, the flexible linker constructs with only a 5 amino acid linker were completely ineffective at blocking CD28 shedding regardless of whether they were fused to HSA or ALB-8. Similarly, wherein only a single amino acid separated the VHH from PEGylated HSA the molecule was not effective at shedding blocking. The results with a very long flexible linker of 35 amino acids were only slightly better, with the intermediate linker of 15 amino acids showing the best results, though these were only marginally better than the isotype control. Four constructs did show significant shedding blocking. Both constructs with a rigid linker produced significant shedding blocking, albeit at a lower level than the parental VHH. Both PEGylated VHHs (without HSA) also showed significant shedding blocking and indeed the 2A1-1C-R20K produced shedding that was even slightly superior to the parental VHH. The percent blocking is summarized in Table 8.

TABLE 8

| Percent shedding blocking by the half-life extending constructs | |
| --- | --- |
| Agent | Inhibition (%) |
| MMPi | 60.5 |
| Isotype Control | 22.7 |
| 2A1 parental | 58.9 |
| 2A1-5GS-Alb8 | 17.9 |
| 2A1-1C-P2K-HSA | 18.1 |
| 2A1-5GS-HSA | 22.8 |
| 2A1-35GS-Alb8 | 23.7 |
| 2A1-35GS-HSA | 27.3 |
| 2A1-15GS-HSA | 27.3 |
| 2A1-15GS-Alb8 | 30.2 |
| 2A1-30Hel-HSA | 32.4 |
| 2A1-20Hel-HSA | 39 |
| 2A1-1C-L40K | 54.6 |
| 2A1-1C-R20K | 64.6 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. An agent comprising at least two moieties separated by a linker, wherein a first moiety binds membranal CD28 (mCD28) on a surface of a cell and inhibits proteolytic cleavage of said mCD28 and wherein a second moiety increases stability of said first moiety, wherein said linker is at least one of:

a rigid peptide linker;

a peptide linker comprising a helix motif;

comprising at least 15 amino acids;

a rigid linker comprising at least 30 amino acids;

comprising at least one cysteine residue; and comprising at least one C-terminal cysteine residue.

2. The agent of claim 1, wherein at least one of:

said first moiety, said second moiety, or both are smaller than 100 kilodaltons (kDa);

said agent is smaller than 100 kDa;

said first moiety, is selected from an antigen binding fragment of an antibody, a Fab fragment, a single chain antibody, a single domain antibody, a small molecule and a peptide that specifically binds to CD28;

said first moiety comprises or consists of a single domain antibody; and said first moiety comprises or consists of a camelid or shark antibody.

3. The agent of claim 2, wherein said first moiety is a single domain antibody comprising three CDRs wherein:

CDR1 comprises the amino acid sequence set forth in SEQ ID NO: 1 (INAMG),

CDR2 comprises the amino acid sequence as set forth in SEQ ID NO: 2 (AISGGGDTYYADSVKG), CDR3 comprises the amino acid sequence as set forth in SEQ ID NO: 3 (DLYGSDYWD);

CDR1 comprises the amino acid sequence set forth in SEQ ID NO: 4 (INAMA),

CDR2 comprises the amino acid sequence as set forth in SEQ ID NO: 5 (AITSSGSTNYANSVKG), CDR3 comprises the amino acid sequence as set forth in SEQ ID NO: 6 (DEYGSDYWI); or CDR1 comprises the amino acid sequence set forth in SEQ ID NO: 1 (INAMG), CDR2 comprises the amino acid sequence as set forth in SEQ ID NO: 7 (AITSGGSTNYADSVKG), CDR3 comprises the amino acid sequence as set forth in SEQQ ID NO: 8 (DLYGEDYWI).

4. The agent of claim 3, wherein said first moiety comprises a sequence selected from a group consisting of:

```
                                    (SEQ ID NO: 9)
a.    EVQLVESGGGLVQAGESLRLSCAASGSIASINAMGWYRQAPGS

QRELVAAISGGGDTYYADSVKGRFTISRDNAKTTVYLQMNSLR

PEDTAVYYCVVDLYGSDYWDWGQGTQVTVSS;

(SEQ ID NO: 10)
b.    EVQLVESGGGLVQAGGSLRLSCAASGSLFSINAMAWYRQAPGK

QRELVAAITSSGSTNYANSVKGRFTVSRDNAKNTMYLQMNSLK

PEDTAVYYCVVDEYGSDYWIWGQGTQVTVSS;
and (SEQ ID NO: 11)
c.    QVQLVESGGGLVQAGGSLRLSCAASGSIFSINAMGWYRQAPGK

QRERVAAITSGGSTNYADSVKGRFTISRDNAKNTVYLQMNNLE

PRDAGVYYCVVDLYGEDYWIWGQGTQVTVSS.
```

5. The agent of claim 1, wherein said first moiety comprises three heavy chain CDRs (CDR-H) and three light chain CDRs (CDR-L), wherein:

CDR-H1 comprises the amino acid sequence set forth in SEQ ID NO: 12 (GFTFSSYYMS), CDR-H2 comprises the amino acid sequence as set forth in SEQ ID NO: 13 (TISDGGDNTYYAGTVTG), CDR-H3 comprises the amino acid sequence as set forth in SEQ ID NO: 14 (IHWPYYFDS), CDR-L1 comprises the amino acid sequence as set forth in SEQ ID NO: 15 (RASSSVSYMN), CDR-L2 comprises the amino acid sequence as set forth in SEQ ID NO: 16 (ATSDLAS), and CDR-L3 comprises the amino acid sequence as set forth in SEQ ID NO: 17 (QQWSSHPPT).

6. The agent of claim 1, wherein at least one of:

said agent is not a CD28 agonist;

said agent is not a CD28 antagonist; and said increased stability of said first moiety comprises increasing stability in blood, reducing clearance of said first moiety from blood, reducing renal filtration, reducing lysosomal degradation or a combination thereof.

7. The agent of claim 1, wherein said second moiety is selected from:

polyethylene glycol (PEG) and is attached to a cysteine in said linker via a thiol linkage;

PEG and said PEG is conjugated within 10 amino acids of a C-terminus of said first moiety;

PEG and said PEG is conjugated to an amino acid of a peptide linker;

linear or branched PEG comprising a size from 2000-40, 000 Daltons (Da);

comprising or consisting of a human serum albumin (HSA) binding polypeptide;

comprising or consisting of an HSA binding single domain antibody.

8. The agent of claim 1, wherein said second moiety comprises or consists of a human serum albumin (HSA) polypeptide.

9. The agent of claim 7, wherein said second moiety is a single domain antibody comprising or consisting of the sequence:

```
                                    (SEQ ID NO: 19)
EVQLVESGGGLVQPGNSLRLSCAASGFTFSSFGMSWVRQAPGKGLEWVSS

ISGSGSDTLYADSVKGRFTISRDNAKTTLYLQMNSLRPEDTAVYYCTIGG

SLSRSSQGTLVTVSSAAA.
```

10. The agent of claim 1, wherein a C-terminus of said first moiety is linked to said linker and an N-terminus of said second moiety is linked to said linker.

11. The agent of claim 1, wherein said agent comprises or consist of:

an amino acid sequence selected from SEQ ID NO: 63 and 64;

an amino acid sequence of SEQ ID NO: 36 and comprises irreversible conjugating a PEG moiety to an amino acid residue within 10 amino acids of a C-terminus of said first moiety; or an amino acid sequence of SEQ ID NO: 36 and comprises reversible conjugating a PEG moiety to an amino acid residue within 10 amino acids of a C-terminus of said first moiety.

12. A nucleic acid molecule encoding the agent of claim 1.

13. An expression vector comprising the nucleic acid molecule of claim 12.

14. A method of generating an agent, the method comprising either:

obtaining a first moiety that binds mCD28 on a cell surface and inhibits proteolytic cleavage of said mCD28;

linking said first moiety to a second moiety by a linker to produce a linked agent, wherein a second moiety increases stability of said first moiety and testing binding of said linked agent to mCD28 on a surface of a cell and inhibition of proteolytic cleavage of said mCD28; and selecting a linked agent that binds mCD28 on a cell surface and inhibits proteolytic cleavage of said mCD28; or culturing a host cell comprising one or more vectors comprising a nucleic acid sequence encoding an agent, wherein the nucleic acid sequence is that of an agent that was selected by:

obtaining a first moiety that binds mCD28 on a cell surface and inhibits proteolytic cleavage of said mCD28;

linking said first moiety to a second moiety by a linker to produce a linked agent, wherein a second moiety increases stability of said first moiety and testing binding of said linked agent to mCD28 on a surface of a cell and inhibition of proteolytic cleavage of said mCD28; and selecting a linked agent that binds mCD28 on a cell surface and inhibits proteolytic cleavage of said mCD28;

thereby generating an agent.

15. The method of claim 14, further comprising:

assaying mCD28 downstream signaling in the presence of said linked agent and selecting at least one linked agent that neither substantially agonizes nor substantially antagonizes mCD28 signaling.

16. A pharmaceutical composition comprising an agent of claim 1, and a pharmaceutically acceptable carrier, excipient or adjuvant.

17. A method of decreasing soluble CD28 (sCD28) levels, treating and/or preventing cancer or improving PD-1 and/or PD-L1 based immunotherapy in a subject in need thereof, the method comprising administering to said subject a pharmaceutical composition of claim 16, thereby decreasing sCD28 in a subject.

18. The method of claim 17, wherein said subject suffers from cancer, said method does not degrade mCD28, decrease mCD28-mediated immune cell activation, or activate mCD28-mediated immune cell activation or both.

19. The method of claim 14, further comprising assaying stability of said linked agent in blood and selecting at least one linked agent comprising an increased stability as compared to said first moiety in blood.

20. The method of claim 15, further comprising assaying stability of said linked agent in blood and selecting at least one linked agent comprising an increased stability as compared to said first moiety in blood.

* * * * *